US012673027B2

(12) United States Patent　　　(10) Patent No.: US 12,673,027 B2
Dodd et al.　　　　　　　　　　　(45) Date of Patent: Jul. 7, 2026

(54) METHOD FOR THE PRODUCTION OF COMMERCIAL NANOPARTICLE AND MICROPARTICLE POWDERS

(71) Applicant: ICEUTICA PTY LTD., Iluka (AU)

(72) Inventors: Aaron Dodd, Centennial Park (AU); H William Bosch, Bryn Mawr, PA (US); Felix Meiser, Mount Claremont (AU); Marck Norret, Darlington (AU); Adrian Russell, Rivervale (AU)

(73) Assignee: iCeutica Pty Ltd., Iluka (AU)

( * ) Notice: Subject to any disclaimer, the term of this patent is extended or adjusted under 35 U.S.C. 154(b) by 0 days.

(21) Appl. No.: 17/960,703

(22) Filed: Oct. 5, 2022

(65) Prior Publication Data

US 2023/0133244 A1　　May 4, 2023

Related U.S. Application Data

(63) Continuation of application No. 16/880,931, filed on May 21, 2020, now abandoned, which is a
(Continued)

(30) Foreign Application Priority Data

Apr. 24, 2009　(AU) ................................. 2009901747

(51) Int. Cl.
A61K 9/16　　　　(2006.01)
A01N 25/10　　　　(2006.01)
(Continued)

(52) U.S. Cl.
CPC ............ A61K 9/1682 (2013.01); A01N 25/10 (2013.01); A01N 25/12 (2013.01); A01N 25/34 (2013.01);
(Continued)

(58) Field of Classification Search
CPC ....... B02C 23/00; B02C 17/00; B02C 17/002; B02C 19/0056
(Continued)

(56) References Cited

U.S. PATENT DOCUMENTS 3,172,546 A　　3/1965　Schreiner
4,133,814 A　　1/1979　Jones et al.
(Continued)

FOREIGN PATENT DOCUMENTS

EP　　　0670162　　　9/1995
EP　　　0699672　　　3/1996
(Continued)

OTHER PUBLICATIONS

Bahl et al. "Amorphization of Indomethacin by Co-Grinding with Neusiling US2: Amorphization Kinetics, Physical Stability and Mechanism," Pharmaceutical Research, (2006), vol. 23 (10), pp. 2317-2325.
(Continued)

*Primary Examiner* — Matthew Katcoff

(74) *Attorney, Agent, or Firm* — Fish & Richardson P.C.

(57) ABSTRACT

A method for using dry milling to prepare nanoparticle and microparticle powders of a biologically active material are described. The nanoparticle and microparticle powders have desirable powder handling characteristics such as good content uniformity that make them suitable for commercial manufacture of drug products.

1 Claim, 34 Drawing Sheets

Related U.S. Application Data continuation of application No. 15/387,541, filed on Dec. 21, 2016, now abandoned, which is a continuation of application No. 14/279,185, filed on May 15, 2014, now abandoned, which is a continuation of application No. 13/265,933, filed as application No. PCT/AU2010/000467 on Apr. 23, 2010, now abandoned.

(60) Provisional application No. 61/172,300, filed on Apr. 24, 2009.

(51) Int. Cl.

| | |
|---|---|
| *A01N 25/12* | (2006.01) |
| *A01N 25/34* | (2006.01) |
| *A01N 37/38* | (2006.01) |
| *A01N 47/36* | (2006.01) |
| *A01N 55/02* | (2006.01) |
| *A01N 57/20* | (2006.01) |
| *A23L 33/10* | (2016.01) |
| *A23P 10/20* | (2016.01) |
| *A23P 10/30* | (2016.01) |
| *A61J 3/02* | (2006.01) |
| *A61K 9/00* | (2006.01) |
| *A61K 9/14* | (2006.01) |
| *A61K 31/122* | (2006.01) |
| *A61K 31/137* | (2006.01) |
| *A61K 31/18* | (2006.01) |
| *A61K 31/192* | (2006.01) |
| *A61K 31/196* | (2006.01) |
| *A61K 31/198* | (2006.01) |
| *A61K 31/404* | (2006.01) |
| *A61K 31/405* | (2006.01) |
| *A61K 31/415* | (2006.01) |
| *A61K 31/421* | (2006.01) |
| *A61K 31/4709* | (2006.01) |
| *A61K 31/496* | (2006.01) |
| *A61K 31/497* | (2006.01) |
| *A61K 31/53* | (2006.01) |
| *A61K 31/5415* | (2006.01) |
| *A61K 31/565* | (2006.01) |
| *A61K 31/57* | (2006.01) |
| *A61K 33/04* | (2006.01) |
| *A61K 38/13* | (2006.01) |
| *B02C 17/20* | (2006.01) |
| *B02C 19/00* | (2006.01) |

(52) U.S. Cl.

CPC ............ *A01N 37/38* (2013.01); *A01N 47/36* (2013.01); *A01N 55/02* (2013.01); *A01N 57/20* (2013.01); *A23L 33/10* (2016.08); *A23P 10/20* (2016.08); *A23P 10/30* (2016.08); *A61J 3/02* (2013.01); *A61K 9/0075* (2013.01); *A61K 9/145* (2013.01); *A61K 9/146* (2013.01); *A61K 9/1617* (2013.01); *A61K 9/1623* (2013.01); *A61K 9/1635* (2013.01); *A61K 9/1652* (2013.01); *A61K 31/122* (2013.01); *A61K 31/137* (2013.01); *A61K 31/18* (2013.01); *A61K 31/192* (2013.01); *A61K 31/196* (2013.01); *A61K 31/198* (2013.01); *A61K 31/404* (2013.01); *A61K 31/405* (2013.01); *A61K 31/415* (2013.01); *A61K 31/421* (2013.01); *A61K 31/4709* (2013.01); *A61K 31/496* (2013.01); *A61K 31/497* (2013.01); *A61K 31/53* (2013.01); *A61K 31/5415* (2013.01); *A61K 31/565* (2013.01); *A61K*
*31/57* (2013.01); *A61K 33/04* (2013.01); *A61K 38/13* (2013.01); *B02C 17/20* (2013.01); *B02C 19/0056* (2013.01); *A23V 2002/00* (2013.01)

(58) Field of Classification Search
USPC .......................................... 241/2, 21, 22, 30
See application file for complete search history.

(56) References Cited

U.S. PATENT DOCUMENTS

| | | | |
|---|---|---|---|
| 4,200,361 | A | 4/1980 | Malvano et al. |
| 4,380,635 | A | 4/1983 | Peters |
| 4,418,068 | A | 11/1983 | Jones |
| 4,606,909 | A | 8/1986 | Bechgaard et al. |
| 4,607,517 | A | 8/1986 | Finzer et al. |
| 5,145,684 | A | 9/1992 | Liversidge et al. |
| 5,202,129 | A | 4/1993 | Samejima et al. |
| 5,298,262 | A | 3/1994 | Na et al. |
| 5,470,583 | A | 11/1995 | Na et al. |
| 5,478,705 | A | 12/1995 | Czekai et al. |
| 5,500,331 | A | 3/1996 | Czekai et al. |
| 5,510,118 | A | 4/1996 | Bosch et al. |
| 5,518,187 | A | 5/1996 | Bruno et al. |
| 5,534,270 | A | 7/1996 | De Castro |
| 5,591,456 | A | 1/1997 | Franson et al. |
| 6,165,506 | A | 12/2000 | Jain et al. |
| 6,316,029 | B1 | 11/2001 | Jain et al. |
| 6,428,814 | B1 | 8/2002 | Bosch et al. |
| 6,462,093 | B1 | 10/2002 | Miyamoto et al. |
| 6,634,576 | B2 | 10/2003 | Verhoff et al. |
| 6,811,767 | B1 | 11/2004 | Bosch et al. |
| 6,894,064 | B2 | 5/2005 | Arbuthnot et al. |
| 6,908,626 | B2 | 6/2005 | Cooper et al. |
| 7,101,576 | B2 | 9/2006 | Hovey et al. |
| 7,714,006 | B1 | 5/2010 | Scaife et al. |
| 7,750,165 | B2 | 7/2010 | Chattophadhyay et al. |
| 2002/0012675 | A1 | 1/2002 | Jain et al. |
| 2002/0047058 | A1 | 4/2002 | Verhoff et al. |
| 2003/0216457 | A1 | 11/2003 | Scaife et al. |
| 2004/0022846 | A1 | 2/2004 | Depui et al. |
| 2004/0037785 | A1 | 2/2004 | Staniforth et al. |
| 2004/0121003 | A1 | 6/2004 | Chickering, III et al. |
| 2004/0173696 | A1 | 9/2004 | Cunningham et al. |
| 2004/0229038 | A1 | 11/2004 | Cooper et al. |
| 2005/0013857 | A1 | 1/2005 | Fu et al. |
| 2005/0063913 | A1 | 3/2005 | Pruitt et al. |
| 2005/0163839 | A1 | 7/2005 | Dudhara et al. |
| 2005/0276844 | A1 | 12/2005 | Spireas |
| 2006/0154966 | A1 | 7/2006 | Karup et al. |
| 2007/0185177 | A1 | 8/2007 | Chattopadhyay et al. |
| 2008/0254128 | A1 | 10/2008 | Zarkadas et al. |
| 2008/0292584 | A1 | 11/2008 | Roberts |
| 2009/0028948 | A1 | 1/2009 | Payne et al. |
| 2010/0016597 | A1 | 1/2010 | Hirokawa et al. |
| 2010/0092563 | A1 | 4/2010 | Raffaele et al. |
| 2012/0160944 | A1 | 6/2012 | Dodd et al. |
| 2014/0326812 | A1 | 11/2014 | Dodd et al. |
| 2017/0165203 | A1 | 6/2017 | Dodd et al. |
| 2020/0390710 | A1 | 12/2020 | Dodd et al. |

FOREIGN PATENT DOCUMENTS

| | | |
|---|---|---|
| EP | 0600528 | 6/2000 |
| JP | H03-66613 A | 3/1991 |
| JP | 2011/005735 | 1/1999 |
| JP | H11-005735 | 1/1999 |
| JP | 2004/99442 | 4/2004 |
| JP | 2004-331500 | 11/2004 |
| JP | 2007/169226 | 5/2007 |
| JP | 2017081899 | 5/2017 |
| WO | WO 1997/02017 | 1/1997 |
| WO | WO 1997/06781 | 2/1997 |
| WO | WO 1998/35666 | 8/1998 |
| WO | WO 1999/047499 | 10/1998 |
| WO | WO 1999/09988 | 3/1999 |
| WO | WO 2000/32189 | 6/2000 |

(56) References Cited

FOREIGN PATENT DOCUMENTS

| | | |
|---|---|---|
| WO | WO 2001/003670 | 1/2001 |
| WO | WO 2002/000197 | 1/2002 |
| WO | WO 2002/045684 | 6/2002 |
| WO | WO 2002/056866 | 7/2002 |
| WO | WO 2002/094215 | 11/2002 |
| WO | WO 2003/000228 | 1/2003 |
| WO | WO 2004/019937 | 3/2004 |
| WO | WO 2004/058216 | 7/2004 |
| WO | WO 2004/060344 | 7/2004 |
| WO | WO 2005/000273 | 1/2005 |
| WO | WO 2005/002542 | 1/2005 |
| WO | WO 2005/016310 | 2/2005 |
| WO | WO 2005/020933 | 3/2005 |
| WO | WO 2005/032703 | 4/2005 |
| WO | WO 2006/009825 | 1/2006 |
| WO | WO 2006/031026 | 3/2006 |
| WO | WO 2006/041843 | 4/2006 |
| WO | WO 2006/009419 | 7/2006 |
| WO | WO 2006/069419 | 7/2006 |
| WO | WO 2006/116596 | 11/2006 |
| WO | WO 2006/133954 | 12/2006 |
| WO | WO 2007/001451 | 1/2007 |
| WO | WO 2007/070843 | 6/2007 |
| WO | WO 2007/070851 | 6/2007 |
| WO | WO 2007/070852 | 6/2007 |
| WO | WO 2007/117923 | 10/2007 |
| WO | WO 2007/150075 | 12/2007 |
| WO | WO 2008/000042 | 1/2008 |
| WO | WO 2008/013416 | 1/2008 |
| WO | WO 2008/118331 | 10/2008 |
| WO | WO 2009/027337 | 3/2009 |
| WO | WO 2010/017104 | 2/2010 |
| WO | WO 2010/121320 | 10/2010 |
| WO | WO 2010/121321 | 10/2010 |
| WO | WO 2010/121322 | 10/2010 |
| WO | WO 2010/121323 | 10/2010 |
| WO | WO 2010/121324 | 10/2010 |
| WO | WO 2010/121325 | 10/2010 |
| WO | WO 2010/121326 | 10/2010 |
| WO | WO 2010/121327 | 10/2010 |
| WO | WO 2010/121328 | 10/2010 |

OTHER PUBLICATIONS

Barzegar-Jalali et al. "Evaluation of in vitro—in vivo correlation and anticonvulsive effect of carbamazepine after cogrinding with microcrystalline cellulose" J Pharm Pharmaceut Science (2006), vol. 9 (3), pp. 307-316. See abstract, pp. 308-313.

Bowen, "Particle Size Disctribution Measurement from Millimeters to Nanometers and from Rods to Platelets," J Dispersion Sci Tech., 2002, 23(5):631-662.

Diaz et al., "Micronization. Its technological application in the manufacture of finished pharmaceutical forms," Rev Cubana Farm., 2001, 35(3):159-164.

FDA, Naproxen-Patient Information Sheet. Dec. 23, 2004, 1 page.

Fukami et al. "A nanoparticle processing in solid state dramatically increases the cell membrane permeation of a cholesterol lowering drug", Mol. Pharmaceutics, 6 (3):1029-1035, 2009.

Fusao Usui, "Dissolution Improvement of Poorly Water Soluble Drug RS-8359," Proceedings of Powrex Technical Meeting, 2000:G1-G7 (2000).

Grigorieva et al., "Mechanosynthesis of nanocomposites," Journal of Nanoparticle Research vol. 5, p. 439-453, 2003.

Gupta et al. "Formation of Physically Stable Amorphous Drugs by Milling with Neusilin," Journal of Pharmaceutical Sciences, (2003), vol. 92 (3), pp. 536-551.

Guterres et al., "Poly(D,L-lactide) nanocapsules containing non-steroidal anti-inflammatory drugs: gastrointestinal tolerance following intravenous and oral administration", Pharmaceutical Research, 12(10): 1545-1547, 1995.

International Preliminary Report on Patentability in International Application No. PCT/AU2010/000467, dated Jul. 29, 2011, 8 pages.

International Search Report in International Application No. PCT/AU2010/000467, dated Aug. 12, 2010, 4 pages.

Kondo, "Study related to design and development of high polymer prodrug by novel mechanochemical solid-stae polymerization", Journal of Pharmaceutical Society of Japan, 120(12):1337-1346, 2000.

McCormick et al., "The Fundamentals of Mechanochemical Processing", Journal of Metals, vol. 50(11):61-65, 1998.

Notice of Reasons for Rejection in corresponding Japanese Application No. JP 2012-506285, dated Nov. 25, 2014, pp. 1-12.

Nuguru, K., Giambattisto, D., and AI-Ghazawi, A. "Evaluation and Characterization of spray-dried Mannitol as an excipient for DC-formulations of Naproxen sodium." Merck. Sep. 2008, 2 pages.

Office Action in corresponding Application No. MX/a/2011/011216, dated Mar. 30, 2015, pp. 1-9.

Patel et al., "An overview of size reduction technologies in the field of pharmaceutical manufacturing," Asian Journal of Pharmaceutics, Oct.-Dec. 2008, pp. 216-220.

Schaffazick et al., "Freeze-drying polymeric colloidal suspensions: nanocapsules, nanospheres and nanodispersion. A comparative study" European Journal of Pharmaceuticals and Biopharmaceuticals, 56(3): 501-505, 2003.

Sharon Hertz, MD; NDA Approval letter, NDA No. 204592; reference ID 3392875; Deputy Director, Division of Anesthesia, Analgesia and Adduction Products, Office of Drug Evaluation II, Center for Drug Evaluation and Research; Oct. 18, 2013; 6 pages.

Tsuzuki and McCormick, "Mechanochemical Synthesis of Metal Sulphide Nanoparticles," Nanostructured Materials, vol. 12 p. 75-78, 1999.

Tsuzuki and McCormick, "Mechanochemical synthesis of nanoparticles," Journal of Materials Science, vol. 39, p. 5143-5146, 2004.

Tsuzuki et al., "Mechanochemical Synthesis of Gadolinium Oxide Nanoparticles," Nanostructured Materials, vol. 11, No. 1, p. 125-131, 1999.

Tsuzuki et al., "Synthesis of CaC03 nanoparticles by mechanochemical processing." Journal of Nanoparticle Research, vol. 2, p. 375-380, 2000.

Vogt et al., "Dissolution enhancement of fenofibrate by micronization, cogrinding and spray-drying: Comparison with commercial preparations," European Journal of Pharmaceutics and Biopharmaceutics, Elsevier Science Publishers B.Y., 68(2):283-288 Jan. 10, 2008.

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | Time (mins.) | D(0.5) μm | % <0.20 μm | % <0.30 μm | % <0.5 μm | % <1.0 μm | % <2.0 μm | Yield (%) | Variations |
|---|---|---|---|---|---|---|---|---|---|---|---|---|---|---|---|---|---|---|---|---|---|---|
| A | IND | 1.20 | 12 | | LAC | 8.80 | 88 | | | | | | | 30 | 0.223 | 45 | 61 | 71 | 77 | 89 | | |
| B | IND | 1.20 | 12 | | LAC | 8.70 | 87 | SPS | 0.1 | 1 | | | | 30 | 0.215 | 47 | 64 | 84 | 83 | 93 | | |
| C | IND | 1.20 | 12 | | LAC | 8.70 | 87 | SDS | 0.1 | 1 | | | | 30 | 0.189 | 53 | 73 | 88 | 95 | 99 | | |
| D | IND | 1.20 | 12 | | LAC | 8.70 | 87 | SOS | 0.1 | 1 | | | | 30 | 0.203 | 49 | 69 | 84 | 92 | 97 | | |
| E | IND | 1.20 | 12 | | LAC | 8.70 | 87 | B700 | 0.1 | 1 | | | | 30 | 0.167 | 60 | 80 | 93 | 97 | 99 | | |
| F | IND | 1.20 | 12 | | LAC | 8.70 | 87 | B76 | 0.1 | 1 | | | | 30 | 0.192 | 52 | 72 | 89 | 96 | 99 | | |
| G | IND | 1.20 | 12 | | LAC | 8.70 | 87 | SDC | 0.1 | 1 | | | | 30 | 0.191 | 52 | 67 | 77 | 83 | 93 | | |
| H | IND | 1.20 | 12 | | LAC | 8.70 | 87 | SNS | 0.1 | 1 | | | | 30 | 0.225 | 44 | 63 | 79 | 88 | 96 | | |
| I | IND | 1.20 | 12 | | LAC | 8.70 | 87 | LEC | 0.1 | 1 | | | | 30 | 0.230 | 44 | 61 | 75 | 85 | 95 | | |
| J | IND | 0.5 | 10 | | LAC | 4.50 | 90 | | | | | | | 20 | 0.237 | 44 | 57 | 65 | 73 | 85 | | |
| K | IND | 0.5 | 10 | | LAC | 4.45 | 89 | P40S | 0.05 | 1 | | | | 20 | 0.169 | 58 | 72 | 80 | 89 | 97 | | |
| L | IND | 0.5 | 10 | | LAC | 4.45 | 89 | DS | 0.05 | 1 | | | | 20 | 0.249 | 42 | 56 | 68 | 84 | 98 | | |
| M | IND | 0.5 | 10 | | LAC | 4.45 | 89 | AS | 0.05 | 1 | | | | 20 | 0.190 | 52 | 67 | 76 | 84 | 92 | | |
| N | IND | 1.0 | 20 | | LAC | 3.95 | 79 | SDS | 0.05 | 1 | | | | 30 | 0.435 | 24 | 38 | 53 | 67 | 83 | | |
| O | IND | 1.0 | 20 | | | | | SDS | 4.00 | 80 | | | | 30 | 2.612 | 0 | 0 | 0 | 6 | 34 | | |
| P | IND | 4.95 | 99 | | | | | | | | | | | 30 | 1094 | 0 | 0 | 0 | 0 | 2 | | |
| Q | IND | 1.0 | 20 | | LAC | 4.00 | 80 | SDS | 0.05 | 1 | | | | 30 | 5.128 | 0 | 0 | 0 | 0 | 8 | | |
| R | DIC | 1.0 | 20 | | LAC | 3.95 | 79 | SDS | | | | | | 30 | 0.153 | 66 | 84 | 95 | 98 | 99 | | |
| S | DIC | 1.0 | 20 | | | | | SDS | 4.00 | 80 | | | | 30 | 3.173 | 0 | 0 | 0 | 3 | 24 | | |

Figure 1A

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | Time (mins.) | D(0.5) μm | % <0.20 μm | % <0.30 μm | % < 0.5 μm | % > 1.0 μm | % > 2.0 μm | Yield (%) | Variations |
|---|---|---|---|---|---|---|---|---|---|---|---|---|---|---|---|---|---|---|---|---|---|---|
| T | DIC | 4.95 | 99 | | | | | SDS | 0.05 | 1 | | | | 30 | 117 | 0 | 0 | 0 | 1 | 4 | | |
| U | DIC | 1.00 | 20 | | LAC | 4.00 | 80 | | | | | | | 30 | 0.178 | 56 | 74 | 86 | 92 | 97 | | |
| V | DIC | 2.00 | 20 | | MAN | 8.00 | 80 | | | | | | | 30 | 0.2 | 50 | 69 | 84 | 91 | 97 | | |
| W | DIC | 2.00 | 20 | | MAN | 7.90 | 79 | SDS | 0.1 | 1 | | | | 30 | 0.201 | 50 | 69 | 83 | 91 | 97 | | |
| X | DIC | 2.00 | 20 | | MAN | 7.90 | 79 | SOS | 0.1 | 1 | | | | 30 | 0.195 | 51 | 71 | 85 | 92 | 97 | | |
| Y | NAA | 1.75 | 35 | | LAC | 3.2 | 65 | | | | | | | 20 | 2.9 | 18 | 23 | 25 | 26 | 38 | | |
| Z | NAA | 1.75 | 35 | | LAC | 3.25 | 64 | P40S | 0.05 | 1 | | | | 20 | 0.373 | 33 | 45 | 56 | 70 | 87 | | |
| AA | NAA | 1.75 | 35 | | LAC | 3.25 | 64 | SDS | 0.05 | 1 | | | | 20 | 0.293 | 38 | 50 | 60 | 65 | 75 | | |
| AB | NAA | 4.0 | 40 | | LAC | 5.9 | 59 | P40S | 0.1 | 1 | | | | 120 | 0.285 | 37 | 52 | 66 | 75 | 82 | | |
| AC | NAA | 4.0 | 40 | | LAC | 6.0 | 60 | | | | | | | 120 | 6.1 | 0 | 0 | 0 | 0 | 8 | | |
| AD | NAA | 1.40 | 35 | | MAN | 2.60 | 65 | | | | | | | 20 | 0.171 | 58 | 73 | 82 | 86 | 88 | | |
| AE | NAA | 1.40 | 35 | | MAN | 2.52 | 63 | SDS | 0.08 | 2 | | | | 20 | 0.131 | 76 | 90 | 95 | 96 | 98 | | |
| AF | NAA | 1.2 | 30 | | MAN | 2.8 | 70 | | | | | | | 20 | 0.208 | 48 | 64 | 75 | 79 | 84 | | |
| AG | NAA | 1.2 | 30 | | MAN | 2.76 | 69.0 | SDS | 0 | 1.0 | | | | 20 | 0.173 | 58 | 75 | 86 | 91 | 96 | | |
| AH | NAA | 1.2 | 30.0 | | LAC | 2.8 | 70.0 | | | | | | | 20 | 0.396 | 33 | 44 | 53 | 58 | 70 | | |
| AI | NAA | 1.2 | 30.0 | | TCD | 2.8 | 70.0 | | | | | | | 20 | 3.1 | 18 | 24 | 27 | 27 | 37 | | |
| AJ | NAA | 1.2 | 30.0 | | CAC | 2.8 | 70.0 | | | | | | | 20 | 28 | 3 | 4 | 5 | 6 | 10 | | |
| AK | NAA | 1 | 25.0 | | LAA | 3 | 75.0 | | | | | | | 20 | 1.07 | 31 | 41 | 46 | 49 | 67 | | |
| AL | NAA | 1 | 25.0 | | XYL | 3 | 75.0 | | | | | | | 20 | 0.18 | 57 | 75 | 87 | 92 | 95 | | |

Figure 1B

| Sample No. | Active material | | | | Primary Matrix | | | Surfactant #1 | | | Surfactant #2 | | | Time (mins.) | Particle Size | | | | | | Yield (%) | Variations |
|---|---|---|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | Name | Mass (g) | % w/w | | D(0.5) μm | % <0.20 μm | % <0.30 μm | % <0.5 μm | % <1.0 μm | % <2.0 μm | | |
| AM | NAA | 1 | 25.0 | | MAA | 3 | 75.0 | | | | | | | 20 | 0.153 | 66 | 85 | 96 | 98 | 99 | | |
| AN | NAA | 1 | 25.0 | | TCD | 3 | 75.0 | | | | | | | 20 | 0.331 | 35 | 48 | 57 | 62 | 72 | | |
| AO | HAL | 1 | 10.0 | | LAC | 9 | 90.0 | | | | | | | 40 | 2.123 | 0 | 0 | 0 | 0 | 5 | | |
| AP | HAL | 1 | 10.0 | | LAC | 8.9 | 89.0 | LEC | 0.1 | 1.0 | | | | 40 | 0.135 | 74 | 90 | 97 | 98 | 99 | | |
| AQ | MET | 1 | 10.0 | | LAC | 9 | 90.0 | | | | | | | 40 | 4.727 | 0 | 0 | 0 | 0 | 4 | | |
| AR | MET | 1 | 10.0 | | LAC | 8.9 | 89.0 | SDS | 0.1 | 1.0 | | | | 40 | 0.129 | 80 | 93 | 96 | 97 | 98 | | |
| AS | TRI | 1 | 10.0 | | LAC | 9 | 90.0 | | | | | | | 40 | 2.622 | 0 | 0 | 0 | 0 | 25 | | |
| AT | TRI | 1 | 10.0 | | LAC | 8.9 | 89.0 | B700 | 0.1 | 1.0 | | | | 40 | 0.128 | 82 | 96 | 98 | 98 | 99 | | |
| AU | SUL | 1 | 10.0 | | LAC | 9 | 90.0 | | | | | | | 40 | 0.388 | 27 | 42 | 56 | 69 | 86 | | |
| AV | SUL | 1 | 10.0 | | LAC | 8.9 | 89.0 | SDS | 0.1 | 1.0 | | | | 40 | 0.455 | 6 | 26 | 55 | 78 | 96 | | |
| AW | MAN | 1 | 10.0 | | LAC | 9 | 90.0 | | | | | | | 40 | 0.198 | 50 | 71 | 88 | 97 | 97 | | |
| AX | MAN | 1 | 10.0 | | LAC | 8.9 | 89.0 | B700 | 0.1 | 1.0 | | | | 40 | 0.17 | 60 | 82 | 96 | 100 | 100 | | |
| AY | MAN | 1 | 10.0 | | LAC | 8.9 | 89.0 | SDS | 0.1 | 1.0 | | | | 40 | 0.171 | 60 | 82 | 97 | 100 | 100 | | |
| AZ | MAN | 1 | 10.0 | | LAC | 8.9 | 89.0 | LEC | 0.1 | 1.0 | | | | 40 | 0.181 | 56 | 78 | 95 | 100 | 100 | | |
| BA | MAN | 2 | 20.0 | | LAC | 7.9 | 79.0 | SDS | 0.1 | 1.0 | | | | 40 | 0.212 | 47 | 68 | 86 | 96 | 98 | | |
| BB | MAN | 3 | 30.0 | | LAC | 6.9 | 69.0 | SDS | 0.1 | 1.0 | | | | 40 | 0.258 | 36 | 58 | 81 | 94 | 97 | | |
| BC | MTX | 1.5 | 30.0 | | LAC | 3.5 | 69.0 | P407 | 0.1 | 1.0 | | | | 60 | 0.16 | 63 | 77 | 84 | 89 | 93 | | 2 |
| BD | MTX | 1.5 | 30.0 | | LAC | 3.5 | 70.0 | | | | | | | 60 | 0.28 | 40 | 52 | 59 | 59 | 71 | | 2 |
| BE | MTX | 2.5 | 50.0 | | LAC | 2.35 | 47.0 | SDS | 0.8 | 2.0 | P407 | 0.1 | 2 | 60 | 0.148 | 67 | 83 | 92 | 98 | 99 | | 2 |

Figure 1C

| Sample No. | Active material Name | Active Mass (g) | Active %w/w | Active %v/v | Primary Matrix Name | Primary Mass (g) | Primary %w/w | Surfactant #1 Name | Surf #1 Mass (g) | Surf #1 %w/w | Surfactant #2 Name | Surf #2 Mass (g) | Surf #2 %w/w | Time (mins.) | D(0.5) μm | %<0.20 μm | %<0.30 μm | %>0.5 μm | %>1.0 μm | %>2.0 μm | Yield (%) | Variations |
|---|---|---|---|---|---|---|---|---|---|---|---|---|---|---|---|---|---|---|---|---|---|---|
| BF | NAA | 1 | 25 | 30 | MAN | 3 | 75 | | | | | | | 20 | 0.181 | 55 | 74 | 87 | 94 | 97 | | |
| BG | NAA | 1 | 25 | 30 | XYL | 3 | 75 | | | | | | | 20 | 0.177 | 56 | 74 | 85 | 91 | 95 | | |
| BH | NAS | 1.25 | 25 | 30 | TA | 3.75 | 75 | | | | | | | 20 | 0.311 | 37 | 49 | 59 | 64 | 75 | | |
| BI | NAS | 1.25 | 25 | 30 | TA | 3.75 | 74 | | | | | | | 30 | 0.303 | 36 | 50 | 62 | 77 | 89 | | |
| BJ | DIC | 3 | 30 | 31 | LAC | 6.9 | 69 | P40S | 0.1 | 1 | | | | 90 | 0.202 | 49 | 69 | 83 | 88 | 92 | 93 | 1 |
| BK | 2,4D | 1 | 20 | | LAC | 4 | 80 | SDS | 0.1 | 1 | | | | 30 | 1.205 | 17 | 23 | 29 | 43 | 72 | 91 | 1 |
| BL | 2,4D | 1 | 20 | | LAC | 3.95 | 79 | SDA | 0.05 | 1 | | | | 30 | 0.473 | 20 | 33 | 52 | 75 | 82 | 93 | 1 |
| BM | 2,4D | 1 | 20 | | LAC | 3.95 | 79 | T3785 | 0.05 | 1 | | | | 30 | 0.414 | 24 | 38 | 57 | 78 | 94 | 93 | 1 |
| BN | 2,4D | 1 | 20 | | LAC | 3.95 | 79 | D920 | 0.05 | 1 | | | | 30 | 0.402 | 26 | 40 | 57 | 78 | 91 | | |
| BO | 2,4D | 1 | 20 | | LAC | 3.95 | 79 | SDS | 0.05 | 1 | | | | 30 | 0.276 | 36 | 54 | 74 | 92 | 96 | 92 | 1 |
| BP | 2,4D | 1 | 20 | | LAC | 3.95 | 79 | B700 | 0.05 | 1 | | | | 30 | 0.269 | 38 | 54 | 69 | 86 | 95 | 91 | 1 |
| BQ | 2,4D | 1 | 20 | | LAC | 3.95 | 79 | K1251 | 0.05 | 1 | | | | 30 | 0.252 | 41 | 56 | 71 | 89 | 96 | 94 | 1 |
| BR | 2,4D | 1 | 20 | | LAC | 3.95 | 79 | T305 | 0.05 | 1 | | | | 30 | 0.231 | 44 | 59 | 73 | 87 | 96 | 59 | 1 |
| BS | GLY | 1 | 20 | | LAC | 3.95 | 79 | T2700 | 0.05 | 1 | | | | 30 | 0.976 | 25 | 35 | 43 | 50 | 64 | 84 | 4 |
| BT | GLY | 1 | 20 | | LAC | 3.9 | 78 | B700 | 0.05 | 1 | T2700 | 0.05 | 1 | 30 | 1.449 | 21 | 27 | 33 | 42 | 57 | 81 | 4 |
| BU | GLY | 1 | 20 | | LAC | 3.9 | 78 | B700 | 0.05 | 1 | K1251 | 0.05 | 1 | 30 | 0.311 | 37 | 49 | 58 | 66 | 79 | 82 | 4 |
| BV | GLY | 1 | 20 | | LAC | 3.9 | 78 | B700 | 0.05 | 1 | P188 | 0.05 | 1 | 30 | 1.085 | 26 | 34 | 41 | 49 | 66 | 86 | 4 |
| BW | GLY | 1 | 20 | | LAC | 3.9 | 78 | B700 | 0.05 | 1 | T2700 | 0.05 | 1 | 30 | 1.48 | 8 | 11 | 16 | 33 | 62 | | 4 |
| BX | GLY | 1 | 20 | | LAC | 3.9 | 78 | B700 | 0.05 | 1 | | | | 60 | 0.176 | 57 | 74 | 86 | 94 | 96 | 79 | 4 |

Figure 1D

| Sample No. | Active material Name | Active Mass (g) | Active % w/w | Active % v/v | Primary Matrix Name | PM Mass (g) | PM % w/w | Surfactant #1 Name | S1 Mass (g) | S1 % w/w | Surfactant #2 Name | S2 Mass (g) | S2 % w/w | Time (mins.) | D(0.5) μm | % >0.20 μm | % >0.30 μm | % > 0.5 μm | % > 1.0 μm | % > 2.0 μm | Yield (%) | Variations |
|---|---|---|---|---|---|---|---|---|---|---|---|---|---|---|---|---|---|---|---|---|---|---|
| BY | GLY | 1 | 20 | | LAC | 3.9 | 78 | B700 | 0.05 | 1 | K1251 | 0.05 | 1 | 60 | 0.658 | 0 | 0 | 21 | 93 | 100 | 81 | 4 |
| BZ | GLY | 1 | 20 | | LAC | 3.9 | 78 | B700 | 0.05 | 1 | T2700 | 0.05 | 1 | 60 | 0.159 | 63 | 78 | 88 | 94 | 95 | 79 | 4 |
| CA | GLY | 1 | 20 | | LAC | 3.9 | 78 | B700 | 0.05 | 1 | K1251 | 0.05 | 1 | 60 | 0.297 | 34 | 50 | 70 | 95 | 100 | 81 | 4 |
| CB | MEL | 0.5 | 10 | | LAC | 4.4 | 88 | CEL | 0.1 | 2 | | | | 25 | 1.128 | 31 | 39 | 42 | 48 | 68 | 68 | 1 |
| CC | MEL | 0.5 | 10 | | LAC | 4.3 | 87 | P188 | 0.2 | 3 | BC | 0 | 0 | 25 | 0.27 | 38 | 53 | 59 | 62 | 81 | 73 | 1 |
| CD | MEL | 0.5 | 10 | | LAC | 4.3 | 87 | P188 | 0.2 | 3 | CEL | 0 | 1 | 25 | 0.278 | 40 | 52 | 58 | 62 | 76 | 74 | 1 |
| CE | MEL | 0.5 | 10 | | LAC | 4.3 | 87 | P188 | 0.2 | 3 | DS | 0 | 1 | 25 | 0.12 | 82 | 96 | 100 | 100 | 100 | 88 | 1 |
| CF | MEL | 0.5 | 10 | | LAC | 4.4 | 89 | P188 | 0.1 | 1 | K25 | 0 | 1 | 25 | 0.249 | 42 | 55 | 59 | 61 | 74 | 69 | 1 |
| CG | MEL | 0.25 | 5 | | MAN | 4.6 | 92 | P188 | 0.2 | 3 | LEC | 0.02 | 0.5 | 25 | 0.123 | 81 | 96 | 100 | 100 | 100 | 58 | 1 |
| CH | MEL | 0.5 | 10 | | LAC | 4.3 | 87 | P188 | 0.2 | 3 | LEC | 0.02 | 0.5 | 25 | 0.144 | 71 | 88 | 94 | 94 | 97 | 68 | 1 |
| CI | MEL | 0.5 | 10 | | LAC | 4.3 | 87 | P188 | 0.2 | 3 | SDC | 0.02 | 0.5 | 25 | 0.184 | 54 | 70 | 79 | 81 | 87 | 63 | 1 |
| CJ | MEL | 0.5 | 10 | | LAC | 4.3 | 87 | P188 | 0.2 | 3 | T80 | 0 | 1 | 25 | 0.224 | 45 | 61 | 70 | 75 | 87 | 68 | 1 |
| CK | MEL | 0.25 | 5 | | LAC | 4.7 | 94 | P188 | 0.1 | 1 | | | | 25 | 0.158 | 63 | 81 | 90 | 90 | 93 | 48 | 1 |
| CL | MEL | 0.5 | 10 | | LAC | 4.4 | 87 | P188 | 0.2 | 3 | | | | 25 | 0.169 | 59 | 76 | 85 | 87 | 93 | 58 | 1 |
| CM | MEL | 0.25 | 5 | | LAC | 4.6 | 92 | P188 | 0.2 | 3 | | | | 25 | 0.221 | 46 | 60 | 68 | 69 | 75 | 68 | 1 |
| CN | MEL | 0.5 | 10 | | LAC | 4.3 | 85 | P188 | 0.3 | 5 | | | | 25 | 0.309 | 39 | 49 | 55 | 56 | 66 | 74 | 1 |
| CO | MEL | 0.5 | 9.5 | | MAN | 4.6 | 88 | P188 | 0.2 | 3 | | | | 25 | 0.251 | 43 | 55 | 61 | 62 | 68 | 55 | 1 |
| CP | MEL | 0.5 | 10 | | MAN | 4.5 | 89 | P3000 | 0.1 | 1 | | | | 25 | 1.343 | 29 | 36 | 39 | 43 | 63 | 61 | 1 |
| CQ | MEL | 0.5 | 10 | | MAN | 4.5 | 89 | SDC | 0.1 | 1 | | | | 25 | 1.699 | 25 | 31 | 32 | 37 | 56 | 77 | 1 |

Figure 1E

| Sample No. | Active material |  |  |  | Primary Matrix |  |  | Surfactant #1 |  |  | Surfactant #2 |  |  | Time (mins.) | Particle Size |  |  |  |  |  |  | Yield (%) | Variations |
|---|---|---|---|---|---|---|---|---|---|---|---|---|---|---|---|---|---|---|---|---|---|---|---|
|  | Name | Mass (g) | % w/w | % v/v | Name | Mass (g) | % w/w | Name | Mass (g) | % w/w | Name | Mass (g) | % w/w |  | D(0.5) μm | % <0.20 μm | % <0.30 μm | % >0.5 μm | % >1.0 μm | % >2.0 μm |  |  |  |
| CR | MEL | 0.5 | 10 |  | LAC | 4.4 | 88 | T80 | 0.1 | 2 |  |  |  | 25 | 1.279 | 28 | 35 | 38 | 44 | 65 |  | 68 | 1 |
| CS | MAN | 2.5 | 50 | 45 | LAC | 2.35 | 47 | SDS | 0.15 | 3 |  |  |  | 15 | 0.318 | 31 | 48 | 65 | 80 | 84 |  |  | 5 |
| CT | MAN | 2.5 | 50 | 45 | LAC | 2.45 | 49 | P188 | 0.05 | 1 |  |  |  | 15 | 0.33 | 30 | 46 | 64 | 77 | 82 |  |  | 5 |
| CU | MAN | 2.5 | 50 | 45 | LAC | 2.45 | 49 | P40S | 0.05 | 1 |  |  |  | 15 | 0.333 | 30 | 46 | 63 | 75 | 80 |  |  | 5 |
| CV | MAN | 2.5 | 50 | 45 | LAC | 2.45 | 49 | B700 | 0.05 | 1 |  |  |  | 15 | 0.337 | 29 | 46 | 63 | 76 | 81 |  |  | 5 |
| CW | MAN | 2.5 | 50 | 45 | LAC | 2.45 | 49 | P407 | 0.05 | 1 |  |  |  | 15 | 0.342 | 28 | 45 | 63 | 76 | 82 |  |  | 5 |
| CX | MAN | 2.5 | 50 | 45 | LAC | 2.45 | 49 | T1221 | 0.05 | 1 |  |  |  | 15 | 0.411 | 24 | 40 | 56 | 69 | 75 |  |  | 5 |
| CY | MAN | 2.5 | 50 | 45 | LAC | 2.45 | 49 | DS | 0.05 | 1 |  |  |  | 15 | 0.462 | 22 | 37 | 52 | 65 | 71 |  |  | 5 |
| CZ | MAN | 2.5 | 50 | 45 | LAC | 2.45 | 49 | SDS | 0.05 | 1 |  |  |  | 15 | 1.369 | 1 | 6 | 20 | 43 | 56 |  |  | 5 |
| DA | MAN | 2.5 | 50 | 45 | LAC | 2.45 | 49 | SDA | 0.05 | 1 |  |  |  | 15 | 1.766 | 0 | 2 | 14 | 38 | 52 |  |  | 5 |
| DB | MAN | 2.5 | 50 | 45 | LAC | 2.45 | 49 | CEL | 0.05 | 1 |  |  |  | 15 | 1.86 | 0 | 2 | 14 | 37 | 51 |  |  | 5 |
| DC | MAN | 2.5 | 50 | 45 | LAC | 2.5 | 50 |  |  |  |  |  |  | 15 | 2.578 | 0 | 1 | 11 | 31 | 45 |  |  | 5 |
| DD | CEL | 0.5 | 10 |  | LAC | 4.3 | 86 | SDS | 0.1 | 2 | P40S | 0.1 | 2 | 15 | 0.134 | 76 | 88 | 91 | 91 | 93 | 88 |  | 1 |
| DE | CEL | 0.5 | 10 |  | LAC | 4.3 | 86 | SDS | 0.1 | 2 | P407 | 0.1 | 2 | 15 | 0.14 | 75 | 83 | 83 | 83 | 86 | 90 |  | 1 |
| DF | CEL | 0.5 | 10 |  | LAC | 4.3 | 86 | SDS | 0.1 | 1 | LEC | 0.15 | 3 | 15 | 0.181 | 55 | 70 | 79 | 83 | 89 | 90 |  | 1 |
| DG | CEL | 0.5 | 10 |  | LAC | 4.3 | 86 | SDS | 0.1 | 1 | B700 | 0.15 | 3 | 15 | 1.903 | 28 | 37 | 44 | 46 | 51 | 90 |  | 1 |
| DH | CEL | 0.5 | 10 |  | LAC | 4.5 | 90 | SDS | 0.1 | 1 |  |  |  | 15 | 5.296 | 8 | 11 | 13 | 13 | 16 | 85 |  | 1 |
| DI | CEL | 0.5 | 10 |  | LAC | 4.3 | 86 | SDS | 0.1 | 1 | P3000 | 0.15 | 3 | 15 | 0.397 | 33 | 45 | 53 | 59 | 71 | 88 |  | 1 |
| DJ | CEL | 0.5 | 10 |  | LAC | 4.4 | 88 | SDS | 0.1 | 1 | P8000 | 0.05 | 1 | 15 | 0.234 | 44 | 58 | 69 | 77 | 87 | 87 |  | 1 |

Figure 1F

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | Time (mins.) | D(0.5) µm | % <0.20 µm | % <0.30 µm | % >0.5 µm | % >1.0 µm | % >2.0 µm | Yield (%) | Variations |
|---|---|---|---|---|---|---|---|---|---|---|---|---|---|---|---|---|---|---|---|---|---|---|
| DK | CEL | 0.5 | 10 | | LAC | 4.3 | 86 | DS | 0.1 | 2 | P40S | 0.1 | 2 | 15 | 0.319 | 35 | 48 | 61 | 69 | 74 | 88 | 1 |
| DL | CEL | 0.5 | 10 | | SOR | 4.5 | 90 | | | | | | | 15 | 16.031 | 0 | 0 | 0 | 0 | 0.8 | 46 | 1 |
| DM | CEL | 0.5 | 10 | | SOR | 4.45 | 89 | SDS | 0.1 | 1 | | | | 15 | 0.173 | 57 | 72 | 79 | 80 | 86 | 52 | 1 |
| DN | CYA | 0.5 | 10 | | LAC | 4.45 | 89 | SDS | 0.1 | 1 | | | | 20 | 0.159 | 65 | 84 | 95 | 100 | 100 | 79 | 5 |
| DO | CYA | 0.5 | 10 | | MAN | 4.45 | 89 | SDS | 0.1 | 1 | | | | 20 | 0.194 | 52 | 68 | 79 | 84 | 84 | 87 | 5 |
| DP | PRO | 0.5 | 10 | | LAC | 4.45 | 89 | SDS | 0.1 | 1 | | | | 20 | 0.229 | 43 | 63 | 83 | 97 | 98 | 87 | 5 |
| DQ | PRO | 0.5 | 10 | | MAN | 4.45 | 89 | SDS | 0.1 | 1 | | | | 20 | 0.553 | 15 | 27 | 45 | 77 | 94 | 89 | 5 |
| DR | PRO | 0.5 | 10 | | LAC | 4.45 | 89 | C40 | 0.1 | 1 | | | | 20 | 0.546 | 10 | 23 | 45 | 76 | 89 | 72 | 5 |
| DS | SAL | 0.51 | 10 | | LAC | 4.5 | 89.5 | LEC | 0.05 | 1 | | | | 20 | 0.128 | 84 | 98 | 100 | 100 | 100 | | |
| DT | SAL | 0.51 | 10 | | LAC | 4.5 | 89.5 | LEC | 0.05 | 1 | | | | 20 | 0.42 | 31 | 42 | 53 | 57 | 57 | | |
| DU | CIP | 0.76 | 15 | | MAL | 4.1 | 83 | T80 | 0.05 | 1 | DS | | | 20 | 0.22 | 40 | 74 | 85 | 85 | 92 | 96 | 6 |
| DV | CIP | 0.76 | 15 | | LAC | 4.2 | 85 | | | | | | | 20 | 25.909 | 1 | 2 | 3.1 | 4.8 | 7 | 89 | 6 |
| DW | CIP | 0.76 | 15 | | MAL | 4.3 | 85 | | | | | | | 20 | 0.238 | 43 | 56 | 58 | 58 | 61 | 93 | 6 |
| DX | CIP | 0.75 | 15 | | LAA | 4.3 | 85 | | | | | | | 20 | 0.205 | 49 | 62 | 65 | 65 | 71 | 97 | 6 |
| DY | CIP | 0.75 | 15 | | LAA | 4.2 | 84 | T80 | 0.06 | 1 | | | | 20 | 0.14 | 75 | 91 | 94 | 94 | 96 | 96 | 6 |
| DZ | CIP | 0.75 | 15 | | LAA | 4.2 | 84 | SOL | 0.05 | 1 | | | | 20 | 0.237 | 35 | 66 | 78 | 78 | 84 | 97 | 6 |
| EA | CIP | 0.75 | 15 | | LAA | 4.2 | 84 | CEL | 0.06 | 1 | | | | 20 | 0.23 | 37 | 69 | 81 | 81 | 87 | 87 | 6 |
| EB | CIP | 0.75 | 15 | | LAA | 4.2 | 84 | DS | 0.05 | 1 | | | | 20 | 0.216 | 42 | 74 | 83 | 83 | 91 | 96 | 6 |
| EC | CIP | 0.75 | 15 | | LAA | 4.2 | 84 | P8000 | 0.05 | 1 | | | | 20 | 0.243 | 33 | 64 | 75 | 75 | 82 | 97 | 6 |

Figure 1G

| Sample No. | Active material | | | | Primary Matrix | | | Surfactant #1 | | | Time (mins.) | Particle Size | | | | | | Yield (%) | Variations |
|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | | D(0.5) μm | % <0.20 μm | % <0.30 μm | % >0.5 μm | % >1.0 μm | % >2.0 μm | | |
| A | IND | 1.20 | 12 | | LAC | 8.80 | 88 | | | | 30 | 0.753 | 25 | 34 | 44 | 55 | 70 | | |
| B | IND | 1.20 | 12 | | LAC | 8.70 | 87 | SDS | 0.1 | 1 | 30 | 0.677 | 14 | 26 | 41 | 65 | 91 | | |
| C | IND | 1.20 | 12 | | LAC | 8.70 | 87 | B700 | 0.1 | 1 | 30 | 0.621 | 13 | 25 | 43 | 68 | 91 | | |
| D | MEL | 1.2 | 20.0 | | MAN | 4.62 | 77 | SDS | 0.18 | 3.0 | 10 | 0.277 | 37 | 53 | 66 | 74 | 86 | 83 | |
| E | MEL | 1.2 | 20.0 | | MAN | 4.8 | 80 | | | | 15 | 2.493 | 10 | 12 | 12 | 15 | 39 | 33 | |
| F | DIC | 3 | 30 | 30 | MAN | 6.7 | 67 | SDS | 0.3 | 3 | 90 | 0.157 | 63 | 79 | 86 | 88 | 93 | | |

Figure 2A

| Sample No. | Active material | | | Primary Matrix | | | 2nd Matrix | | | Time (mins.) | Particle Size | | | | | | Yield (%) | Variations |
|---|---|---|---|---|---|---|---|---|---|---|---|---|---|---|---|---|---|---|
| | Name | Mass (g) | % w/w | Name | Mass (g) | % w/w | Name | Mass (g) | % w/w | | D(0.5) μm | % <0.20 μm | % <0.30 μm | % >0.5 μm | % >1.0 μm | % >2.0 μm | | |
| A | NAA | 1.2 | 30.0 | LAC | 2 | 50.0 | TCD | 0.8 | 20.0 | 20 | 0.188 | 48 | 64 | 75 | 81 | 92 | | |
| B | NAA | 1.2 | 30.0 | LAC | 2 | 50.0 | CAC | 0.8 | 20.0 | 20 | 0.213 | 47 | 63 | 76 | 84 | 91 | | |
| C | NAA | 1 | 25.0 | LAA | 2.2 | 55.0 | XYL | 0.8 | 20.0 | 20 | 0.2 | 50 | 65 | 75 | 79 | 89 | | |
| D | NAA | 1 | 25.0 | LAA | 2.2 | 55.0 | MAA | 0.8 | 20.0 | 20 | 0.223 | 46 | 60 | 70 | 76 | 87 | | |
| E | NAA | 1 | 25.0 | LAA | 2.2 | 55.0 | TCD | 0.8 | 20.0 | 20 | 0.215 | 47 | 62 | 70 | 73 | 83 | | |

| Sample No. | Active material | | | | Primary Matrix | | | Surfactant #1 | | | 2nd Matrix | | | Time (mins.) | Particle Size | | | | | | Yield (%) | Variations |
|---|---|---|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | Name | Mass (g) | % w/w | | D(0.5) μm | % <0.20 μm | % <0.30 μm | % >0.5 μm | % >1.0 μm | % >2.0 μm | | |
| A | MEL | 20 | 20.0 | | LAC | 77 | 77.0 | SDS | 3 | 3.0 | | | | 15 | 0.24 | 39 | 64 | 87 | 97 | 100 | 90 | |
| B | MEL | 20 | 20.0 | | LAC | 80 | 80.0 | | | | | | | 15 | 0.166 | 59 | 74 | 82 | 87 | 90 | 0.7 | |
| C | IND | 13 | 13.0 | | LAC | 87 | 87.0 | | | | | | | 30 | 3.255 | 0 | 0 | 0 | 4 | 27 | 1 | |
| D | IND | 13 | 13.0 | | LAC | 65.5 | 65.5 | | | | TA | 22 | 21.5 | 30 | 0.272 | 34 | 55 | 76 | 87 | 93 | 0 | |
| E | IND | 13 | 13.0 | | LAC | 86 | 86.0 | SDS | 1 | 1.0 | | | | 30 | 0.836 | 22 | 31 | 39 | 56 | 83 | 76 | |
| F | IND | 13 | 13.0 | | LAC | 64.5 | 64.5 | SDS | 1 | 1.0 | TA | 22 | 21.5 | 30 | 0.629 | 15 | 28 | 43 | 67 | 91 | 85 | |
| G | MEL | 25 | 25 | 25 | LAC | 72 | 72 | SDS | 3 | 3 | | | | 15 | 0.283 | 33 | 53 | 73 | 84 | 92 | | |

Figure 5A

| Sample No. | Active material | | | Primary Matrix | | | Surfactant #1 | | | Surfactant #2 | | | Time (mins.) | Particle Size | | | | | | Yield (%) | Variations |
|---|---|---|---|---|---|---|---|---|---|---|---|---|---|---|---|---|---|---|---|---|---|
| | Name | Mass (g) | % w/w | Name | Mass (g) | % w/w | Name | Mass (g) | % w/w | Name | Mass (g) | % w/w | | D(0.5) μm | % >0.20 μm | % >0.30 μm | % >0.5 μm | % >1.0 μm | % >2.0 μm | | |
| A | NAA | 17.5 | 35.0 | MAN | 32 | 64.0 | SDS | 0.5 | 1.0 | | | | 80 | 0.249 | 42 | 56 | 64 | 67 | 74 | | |
| B | NAA | 17.5 | 35.0 | MAN | 31.5 | 63.0 | SDS | 0.5 | 1.0 | P40S | 0.5 | 1 | 80 | 0.261 | 39 | 55 | 67 | 77 | 88 | | |
| C | NAA | 17.5 | 35.0 | MAN | 31.5 | 63.0 | SDS | 0.5 | 1.0 | P3000 | 0.5 | 1 | 80 | 0.188 | 53 | 70 | 81 | 88 | 95 | | |
| D | IND | 6 | 12.0 | LAC | 43.5 | 87.0 | SDS | 0.5 | 1.0 | | | | 40 | 0.231 | 43 | 61 | 78 | 91 | 97 | | |
| E | IND | 6 | 12.0 | LAC | 43 | 86.0 | SDS | 0.5 | 1.0 | P407 | 0.5 | 1 | 40 | 0.152 | 66 | 85 | 95 | 97 | 98 | | |
| F | IND | 6 | 12.0 | LAC | 43 | 86.0 | SDS | 0.5 | 1.0 | P40S | 0.5 | 1 | 40 | 0.155 | 65 | 85 | 96 | 98 | 98 | | |

| Sample No. | Active material Name | Active Mass (g) | Active W/W % | Active % v/v | Primary Matrix Name | Primary Mass (g) | Primary W/W % | Surfactant #1 Name | Surf#1 Mass (g) | Surf#1 W/W % | Surfactant #2 Name | Surf#2 Mass (g) | Surf#2 W/W % | 2nd Matrix Name | 2nd Matrix Mass (g) | 2nd Matrix W/W % | Time (mins.) | D(0.5) µm | % <0.20 µm | % <0.30 µm | % < 0.5 µm | % < 1.0 µm | % < 2.0 µm | No. Ave. nm | Yield (%) | Variations |
|---|---|---|---|---|---|---|---|---|---|---|---|---|---|---|---|---|---|---|---|---|---|---|---|---|---|---|
| A | NAA | 70 | 35 | | LAC | 128 | 64 | SDS | 2 | 1 | | | | | | | 60 | 0.345 | 35 | 47 | 56 | 61 | 73 | | 98 | O |
| B | NAA | 70 | 35 | | MAN | 128 | 64 | SDS | 2 | 1 | | | | | | | 50 | 0.73 | 31 | 41 | 48 | 51 | 58 | | | C |
| C | NAA | 60 | 30.0 | | MAN | 138 | 69.0 | SDS | 2 | 1.0 | | | | | | | 50 | 0.181 | 55 | 73 | 86 | 92 | 96 | | 92 | C |
| D | NAA | 60 | 30.3 | | MAN | 138 | 69.7 | | | | | | | | | | 50 | 0.319 | 35 | 48 | 59 | 64 | 75 | | 23 | C |
| E | DIC | 52.5 | 15.0 | | LAC | 294 | 84.0 | SDS | 3.5 | 1.0 | | | | | | | 40 | 0.16 | 64 | 84 | 97 | 99 | 99 | | 64 | E |
| F | DIC | 52.5 | 13.0 | | LAC | 224 | 66.0 | SDS | 3.5 | 1.0 | | | | | | | 40 | 0.16 | 63 | 83 | 95 | 98 | 99 | | 87 | E |
| G | NAA | 60 | 30 | 35 | LAC | 138 | 69 | SDS | 2 | 1 | | | | TA | 70 | 20 | 40 | 0.232 | 44 | 59 | 70 | 78 | 90 | | 79 | E |
| H | 2,4D | 40 | 20 | | LAC | 160 | 80 | SDA | 2 | 1 | | | | | | | 30 | 0.212 | 47 | 69 | 90 | 100 | 100 | | 95 | |
| I | 2,4D | 40 | 20 | | LAC | 158 | 79 | K1251 | 2 | 1 | | | | | | | 30 | 0.189 | 53 | 72 | 87 | 95 | 97 | | 97 | |
| J | 2,4D | 40 | 20 | | LAC | 158 | 79 | D920 | 2 | 1 | | | | | | | 30 | 0.2 | 50 | 71 | 89 | 97 | 97 | | 97 | |
| K | 2,4D | 40 | 20 | | LAC | 158 | 79 | SDA | 3 | 1 | PVP | 3 | 1 | | | | 30 | 0.204 | 49 | 69 | 86 | 94 | 96 | | 94 | |
| L | 2,4D | 60 | 20 | | LAC | 234 | 78 | D920 | 4 | 1 | PVP | 3 | 1 | | | | 30 | 0.281 | 30 | 54 | 82 | 97 | 98 | | 93 | |
| M | 2,4D | 60 | 20 | | LAC | 234 | 78 | K1251 | 3 | 1 | PVP | 3 | 1 | | | | 40 | 0.183 | 55 | 75 | 91 | 98 | 100 | | 90 | |
| N | 2,4D | 60 | 20 | | LAC | 234 | 78 | B700 | 2 | 1 | T2700 | 2 | 1 | | | | 40 | 0.208 | 48 | 68 | 88 | 99 | 100 | | 92 | |
| O | GLY | 40 | 20 | | LAC | 158 | 79 | B700 | 2 | 1 | | | | | | | 90 | 0.297 | 38 | 50 | 61 | 74 | 87 | | 18 | |
| P | GLY | 40 | 20 | | LAC | 156 | 78 | B700 | 3 | 1 | T2700 | 3 | 1 | | | | 45 | 0.188 | 53 | 71 | 85 | 93 | 96 | | 79 | D |
| Q | GLY | 60 | 20 | | LAC | 234 | 78 | B700 | 3 | 1 | T2700 | 3 | 1 | | | | 30 | 4.798 | 0 | 0 | 0 | 0.2 | 9.9 | | | D |
| R | GLY | 60 | 20 | | LAC | 234 | 78 | B700 | 3 | 1 | | | | | | | 50 | 0.204 | 49 | 66 | 79 | 89 | 94 | | | D |

Figure 6A

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | 2nd Name | 2nd Mass (g) | 2nd % w/w | Time (mins.) | D(0.5) μm | % >0.20 μm | % >0.30 μm | % >0.5 μm | % >1.0 μm | % >2.0 μm | No. Ave. nm | Yield (%) | Variations |
|---|---|---|---|---|---|---|---|---|---|---|---|---|---|---|---|---|---|---|---|---|---|---|---|---|---|---|
| S | GLY | 60 | 20 | | LAC | 234 | 78 | B700 | 3 | 1 | T2700 | 3 | 1 | | | | 70 | 0.17 | 58 | 75 | 88 | 95 | 97 | | 94.7 | D |
| T | MEL | 35 | 10 | | LAC | 311.5 | 89 | LEC | 3.5 | 1 | | | | | | | 40 | 0.127 | 80 | 94 | 98 | 98 | 99 | | 81 | |
| U | MEL | 35 | 10 | | MAN | 311.5 | 89 | LEC | 3.5 | 1 | | | | | | | 20 | 0.199 | 50 | 67 | 76 | 82 | 91 | | 59 | 1 |
| V | MEL | 35 | 10 | | LAC | 309.8 | 89 | P188 | 3.5 | 1 | DS | 1.77 | 1 | | | | 20 | 0.13 | 77 | 94 | 100 | 100 | 100 | | 90 | 1 |
| W | MEL | 17.5 | 5 | | MAN | 323.8 | 93 | P188 | 7 | 2 | LEC | 1.75 | 0.5 | | | | 25 | 0.124 | 80 | 96 | 100 | 100 | 100 | | 67 | 1 |
| X | MEL | 17.5 | 5 | | LAC | 320.3 | 92 | P188 | 10.5 | 3 | LEC | 1.75 | 0.5 | | | | 40 | 0.129 | 78 | 94 | 99 | 99 | 99 | | 94 | 1 |
| Y | MEL | 17.5 | 5 | | MAN | 320.3 | 92 | P188 | 10.5 | 3 | LEC | 1.75 | 0.5 | | | | 25 | 0.14 | 72 | 88 | 93 | 94 | 98 | | 97 | 1 |
| Z | MEL | 35 | 10 | | LAC | 302.8 | 87 | P188 | 10.5 | 3 | LEC | 1.75 | 0.5 | | | | 30 | 0.168 | 59 | 75 | 83 | 87 | 94 | | 52 | 1 |
| AA | MEL | 35 | 10 | | LAC | 311.5 | 89 | P188 | 3.5 | 1 | | | | | | | 40 | 0.118 | 87 | 99 | 100 | 100 | 100 | | 87 | 1 |
| AB | MEL | 35 | 10 | | LAC | 311.5 | 89 | P188 | 3.5 | 1 | | | | | | | 30 | 0.164 | 60 | 77 | 87 | 93 | 97 | | 32 | 1 |
| AC | MEL | 35 | 10 | | MAN | 315.0 | 90 | | | | | | | | | | 20 | 0.143 | 71 | 89 | 95 | 96 | 98 | | 79 | 1 |
| AD | MEL | 35 | 10 | | LAC | 315.0 | 90 | | | | | | | | | | 25 | 0.26 | 39 | 55 | 66 | 73 | 85 | | 56 | 1 |
| AE | CRM | 60 | 20 | | MAN | 138 | 69 | LEC | 1 | 2 | | | | | | | 60 | 0.152 | 64 | 78 | 84 | 87 | 89 | | 79 | 7 |
| AF | CIL | 30 | 10 | | LAC | 267 | 89 | SDS | 3 | 1 | | | | | | | 20 | 0.162 | 64 | 86 | 99 | 100 | 100 | | 84 | 7 |
| AG | PRO | 30 | 10 | | LAC | 267 | 89 | SDS | 3 | 1 | | | | | | | 30 | 0.62 | 12 | 24 | 42 | 67 | 89 | | 74 | 5,D |
| AH | PRO | 30 | 10 | | LAC | 270 | 90 | | | | | | | | | | 30 | 0.91 | 9 | 18 | 33 | 52 | 61 | | 66 | 5,D |
| AI | CIP | 30.0 | 15 | | LAA | 168.0 | 84 | T80 | 2.00 | 1 | | | | | | | 20 | 0.139 | 76 | 91 | 94 | 94 | 95 | 88 | 94 | E |
| AJ | CIP | 30.1 | 15 | | LAA | 170.0 | 85 | | | | | | | | | | 20 | 0.171 | 60 | 75 | 79 | 79 | 82 | | 36.7 | E |
| AK | CIP | 30.0 | 15 | | LAA | 168.0 | 84 | CEL | 2.00 | 1 | | | | | | | 20 | 0.277 | 41 | 51 | 54 | 54 | 56 | | 72 | E |

Figure 6B

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | 2nd Name | Mass (g) | % w/w | Time (mins.) | D(0.5) μm | % <0.20 μm | % <0.30 μm | % <0.5 μm | % <1.0 μm | % <2.0 μm | No. Ave. nm | Yield (%) | Variations |
|---|---|---|---|---|---|---|---|---|---|---|---|---|---|---|---|---|---|---|---|---|---|---|---|---|---|---|
| AL | GLY | 60.0 | 20 | | LAC | 240.0 | 80 | | | | | | | | | | 70 | 50.4 | 0 | 0 | 0 | 0.9 | 4.4 | 1282 | 26 | 3,P |
| AM | CEL | 20.0 | 10 | | LAC | 176.1 | 88 | SDS | 2.00 | 1 | P40S | 2 | 1 | | | | 10 | 0.205 | 49 | 66 | 79 | 86 | 92 | 81 | 86 | 1,D |
| AN | CEL | 20.0 | 10 | | LAC | 180.1 | 90 | | | | | | | | | | 10 | 4.775 | 0 | 0 | 0 | 0 | 6.4 | 2560 | 57 | 1,D |
| AO | CEL | 20.0 | 10 | | LAC | 176.0 | 88 | SDS | 2.00 | 1 | P8000 | 2 | 1 | | | | 10 | 0.353 | 34 | 46 | 56 | 64 | 77 | 80 | 86 | 1,D |
| AP | MAN | 150.1 | 50 | 45 | LAC | 147.1 | 49 | T3785 | 3.00 | 3 | | | | | | | 5 | 0.22 | 46 | 60 | 72 | 84 | 87 | 89 | 90 | 8,D |
| AQ | MAN | 150.1 | 50 | 45 | LAC | 150.0 | 50 | | | | | | | | | | 5 | 0.292 | 35 | 51 | 67 | 81 | 85 | 109 | 56 | 8,D |
| AR | MAN | 150.0 | 50 | 45 | LAC | 147.0 | 49 | DS | 3.02 | 3 | | | | | | | 5 | 0.274 | 38 | 53 | 67 | 80 | 84 | | 76 | 8,D |
| AS | NAA | 105.1 | 35 | 39 | MAN | 195.0 | 65 | MCC | 15.00 | | | | | | | | 80 | 0.189 | 53 | 70 | 82 | 87 | 91 | 80 | 81 | |
| AT | NAA | 105.0 | 35 | | MAN | 180.1 | 60 | | | 5 | | | | | | | 80 | 0.261 | 40 | 54 | 65 | 69 | 75 | 81 | 66 | D |
| AU | NAA | 105.0 | 35 | | MAN | 180.0 | 60 | PML | 15.10 | 5 | | | | | | | 80 | 0.243 | 42 | 58 | 69 | 76 | 85 | 83 | 51 | D |

Figure 6C

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | 2nd Matrix Name | 2nd Matrix Mass (g) | 2nd Matrix % w/w | Disintegrant Name | Disintegrant Mass (g) | Disintegrant % w/w | Time (mins.) | D(0.5) μm | % <0.20 μm | % <0.30 μm | % > 0.5 μm | % > 1.0 μm | % > 2.0 μm | Yield (%) | Variations |
|---|---|---|---|---|---|---|---|---|---|---|---|---|---|---|---|---|---|---|---|---|---|---|---|---|---|---|---|---|
| A | MTX | 1.5 | 30.0 | | LAC | 3.5 | 69.0 | P407 | 0.1 | 1.0 | | | | | | | | | | 60 | 0.16 | 63 | 77 | 84 | 89 | 93 | | 2 |
| B | MTX | 1.5 | 30.0 | | LAC | 3.5 | 70.0 | | | | | | | | | | | | | 60 | 0.28 | 40 | 52 | 59 | 59 | 71 | | 2 |
| C | MTX | 17.2 | 43.0 | | LAC | 22 | 56.0 | SDS | 0.4 | 1.0 | | | | | | | | | | 60 | 0.142 | 70 | 83 | 88 | 91 | 94 | | 2 |
| D | MTX | 20 | 50.0 | | LAC | 10.4 | 26.0 | SDS | 0.8 | 2.0 | P407 | 0.8 | 2 | SB | 8 | 20.0 | | | | 60 | 0.137 | 73 | 89 | 95 | 100 | 100 | | 9 |
| E | MTX | 2.5 | 50.0 | | LAC | 2.35 | 47.0 | SDS | 0.8 | 2.0 | P407 | 0.1 | 2 | | | | | | | 60 | 0.148 | 67 | 83 | 92 | 98 | 99 | | 2 |
| F | MTX | 17.2 | 43.0 | | MAN | 22.4 | 56.0 | SDS | 0.4 | 1.0 | | | | | | | | | | 60 | 0.254 | 42 | 55 | 64 | 67 | 72 | | 2 |
| G | MTX | 1 | 20 | | LAC | 4 | 80 | | | | | | | | | | | | | 60 | 13.45 | 0 | 0 | 0 | 0 | 0 | 92 | 2 |
| H | MTX | 1 | 20 | | LAC | 3.9 | 78 | SDS | 0.05 | 1 | P407 | 0.05 | 1 | PVP | 0.05 | 1 | | | | 60 | 0.13 | 76 | 91 | 96 | 98 | 98 | 97 | 2 |
| I | MTX | 1.25 | 25 | | LAC | 2.85 | 68 | SDS | 0.05 | 1 | P407 | 0.05 | 1 | | | | PRI | 0.25 | 5 | 50 | 0.201 | 50 | 67 | 80 | 84 | 84 | 85 | 2 |
| J | MTX | 60 | 30 | 33 | LAC | 137 | 67 | SDS | 3 | 1.5 | P407 | 3 | 1.5 | | | | | | | 5 | 3.943 | 20 | 27 | 30 | 31 | 38 | | 2 |
| K | MTX | 60 | 30 | 33 | LAC | 137 | 67 | SDS | 3 | 1.5 | P407 | 3 | 1.5 | | | | | | | 10 | 0.223 | 46 | 61 | 72 | 77 | 83 | | 2 |
| L | MTX | 60 | 30 | 33 | LAC | 137 | 67 | SDS | 3 | 1.5 | P407 | 3 | 1.5 | | | | | | | 16 | 0.153 | 64 | 79 | 86 | 93 | 96 | | 2 |
| M | MTX | 60 | 30 | 33 | LAC | 137 | 67 | | | | P407 | 3 | 1.5 | | | | PRI | 8.04 | 5 | 21 | 0.142 | 67 | 85 | 92 | 95 | 96 | | 2 |
| N | 7M | 151 | 94 | | | | | | | | PVP | 1.61 | 1 | | | | | | | 2 | | | | | | | 97 | 2 |
| O | MTX | 60 | 30 | 33 | LAC | 137 | 67 | SDS | 3 | 1.5 | P407 | 3 | 1.5 | | | | | | | 20 | 0.8 | 32 | 42 | 48 | 51 | 63 | 70 | 2,E |

Figure 7A

| Sample No. | Active material Name | Active material Mass (g) | Active material w/w % | Active material v/v % | Primary Matrix Name | Primary Matrix Mass (g) | Primary Matrix w/w % | Surfactant #1 Name | Surfactant #1 Mass (g) | Surfactant #1 w/w % | Surfactant #2 Name | Surfactant #2 Mass (g) | Surfactant #2 w/w % | 2nd Matrix Name | 2nd Matrix Mass (g) | 2nd Matrix w/w % | Time (mins.) | D(0.5) µm | % <0.20 µm | % <0.30 µm | % >0.5 µm | % >1.0 µm | % >2.0 µm | Yield (%) | Variations |
|---|---|---|---|---|---|---|---|---|---|---|---|---|---|---|---|---|---|---|---|---|---|---|---|---|---|
| A | MEL | 48 | 10 | | LAC | 417.6 | 87 | SDS | 14.4 | 3 | | | | | | | 3 | 0.15 | 66 | 83 | 90 | 91 | 94 | 97 | 1 |
| B | MEL | 24 | 5 | | LAC | 439.2 | 91.5 | P188 | 14.4 | 3 | LEC | 2.4 | 0.5 | | | | 8 | 0.159 | 63 | 81 | 91 | 94 | 98 | 97 | 1 |
| C | MEL | 24 | 5 | | MAN | 439.2 | 91.5 | P188 | 14.4 | 3 | LEC | 2.4 | 0.5 | | | | 8 | 0.144 | 70 | 88 | 94 | 95 | 98 | 92 | 1 |
| D | IND | 62.4 | 13 | | LAC | 312 | 65 | SDS | 4.8 | 1 | | | | TA | 100.8 | 21 | 4 | 0.197 | 51 | 68 | 81 | 88 | 94 | 91 | |
| E | IND | 62.4 | 13 | | LAC | 312 | 66 | | | | | | | TA | 100.8 | 21 | 4 | 0.19 | 53 | 71 | 85 | 92 | 97 | 74 | |
| F | IND | 62.4 | 13 | | LAC | 312 | 65 | SDS | 4.8 | 1 | | | | TA | 100.8 | 21 | 4 | 0.194 | 52 | 71 | 86 | 93 | 97 | 84 | |
| G | IND | 48 | 10 | | SUC | 427.2 | 89 | SDS | 4.8 | 1 | | | | | | | 5 | 0.213 | 47 | 64 | 76 | 84 | 92 | 93 | |
| H | IND | 48 | 10 | | SUC | 427.2 | 89 | SDS | 4.8 | 1 | | | | | | | 6 | 0.192 | 52 | 72 | 87 | 93 | 96 | 94 | |
| I | MTX | 144 | 30 | 33 | LAC | 321.6 | 67 | SDS | 7.2 | 1.5 | P407 | 7.2 | 1.5 | | | | 4 | 0.243 | 44 | 58 | 68 | 74 | 84 | 93 | 2 |
| J | ANT | 50 | 10 | | LAC | 445 | 89 | SDS | 5 | 1 | | | | | | | 4 | 0.288 | 32 | 51 | 73 | 86 | 91 | 90 | 5 |
| K | DIC | 72 | 15 | | LAC | 403.2 | 84 | SDS | 4.8 | 1 | | | | | | | 3 | 0.186 | 54 | 74 | 89 | 95 | 98 | 94 | |
| L | NAA | 168 | 35 | 39 | MAN | 302.4 | 63 | SDS | 4.8 | 1 | | | | | | | 6 | 0.226 | 44 | 63 | 80 | 88 | 93 | 94 | |
| M | NAA | 168 | 35 | 39 | MAN | 297.6 | 62 | SDS | 4.8 | 1 | PVP | 4.8 | 1 | P3000 | 4.8 | 1 | 7 | 0.287 | 31 | 52 | 73 | 85 | 93 | 98 | |
| N | COP | 48 | 10 | | LFG | 427.2 | 89 | SDS | 4.8 | 1 | PVP | 4.8 | 1 | | | | 7 | 4.319 | 0 | 0 | 0 | 3 | 16 | 93 | 10 |
| O | COP | 96 | 20 | | LFG | 374.4 | 78 | LEC | 9.6 | 2 | | | | | | | 18 | 2.375 | 0 | 0 | 0 | 9 | 39 | 80 | 10 |
| P | CON | 144 | 30 | | LFG | 326.4 | 68 | LEC | 9.6 | 2 | | | | | | | 1.5 | 4.027 | 0 | 0 | 0 | 7 | 23 | 83 | 10 |

Figure 8A

| Sample No. | Active material | | | Primary Matrix | | | Surfactant #1 | | | Surfactant #2 | | | 2nd Matrix | | | Time (mins.) | Particle Size | | | | | | | Yield (%) | Variations |
|---|---|---|---|---|---|---|---|---|---|---|---|---|---|---|---|---|---|---|---|---|---|---|---|---|---|
| | Name | Mass (g) | % w/w | Name | Mass (g) | % w/w | Name | Mass (g) | % w/w | Name | Mass (g) | % w/w | Name | Mass (g) | % w/w | | D(0.5) μm | % >0.20 μm | % >0.30 μm | % >0.5 μm | % >1.0 μm | % >2.0 μm | No.Ave.(nm) | | |
| A | MEL | 40 | 5 | MAN | 732 | 91.5 | P188 | 24 | 3 | LEC | 4 | 0.5 | | | | 40 | 0.116 | 84 | 97 | 100 | 100 | 100 | | 96 | 1,I |
| B | MEL | 40 | 5 | MAN | 732 | 91.5 | P188 | 24 | 3 | LEC | 4 | 0.5 | | | | 45 | 0.122 | 82 | 97 | 100 | 100 | 100 | | 95 | 1,I |
| C | MEL | 40 | 5 | MAN | 732 | 91.5 | P188 | 24 | 3 | LEC | 4 | 0.5 | | | | 40 | 0.124 | 80 | 96 | 100 | 100 | 100 | | 97 | 1,I |
| D | MEL | 52.5 | 5 | LAC | 960.8 | 91.5 | P188 | 31.5 | 3 | LEC | 5.25 | 0.5 | | | | 50 | 0.156 | 64 | 81 | 89 | 90 | 93 | | 88 | 1,H |
| E | MEL | 40.0 | 5 | MAN | 732.0 | 91.5 | P188 | 24 | 3 | LEC | 4 | 0.5 | | | | 40 | 0.142 | 71 | 88 | 93 | 93 | 95 | | 96 | 1,I |
| F | SAL | 100.0 | 10 | LAC | 890.0 | 89 | LEC | 10.00 | | | | | | | | 15 | 0.137 | 72 | 85 | 89 | 90 | 92 | 75 | 92 | L |
| G | SAL | 100.0 | 10 | LAC | 900.0 | 90 | | | | | | | | | | 15 | 4.954 | 0 | 0 | 2 | 11 | 24 | | 95 | L |
| H | IND | 130.0 | 13 | LAC | 870.0 | 87 | SDS | 10.00 | 1 | | | | | | | 36 | 0.18 | 56 | 74 | 89 | 96 | 98 | 80 | 65 | |
| I | IND | 130.1 | 13 | LAC | 860.1 | 86 | | | | | | | | | | 36 | 0.192 | 52 | 73 | 90 | 95 | 97 | 83 | 85 | |
| J | IND | 130.1 | 13 | LAA | 870.0 | 87 | | | | | | | | | | 36 | 0.186 | 54 | 72 | 86 | 93 | 97 | 80 | 51 | |
| K | DIC | 150.1 | 15 | LAA | 850.3 | 85 | | | | | | | | | | 36 | 0.242 | 41 | 60 | 79 | 92 | 99 | 87 | 27 | |
| L | MEL | 105.0 | 10 | LAC | 913.5 | 87 | SDS | 31.50 | 3 | | | | | | | 20 | 0.137 | 74 | 90 | 95 | 95 | 96 | 79 | 94 | G |
| M | MEL | 105.1 | 10 | LAC | 945 | 90.0 | | | | | | | TA | 215 | 21.5 | 20 | | | | | | | | | 1,G |
| N | IND | 130.0 | 13 | LAA | 860 | 86 | SDS | 10 | 1 | | | | | | | 36 | 0.161 | 62 | 79 | 90 | 93 | 95 | | 80 | 11,N |
| O | IND | 130.0 | 13 | LAA | 645 | 64.5 | SDS | 10 | 1 | | | | | | | 36 | 0.160 | 62 | 79 | 90 | 94 | 96 | | 87 | 11,N |
| P | DIC | 150 | 15 | LAA | 840 | 84 | SDS | 10 | 1 | | | | | | | 36 | 0.152 | 66 | 84 | 95 | 98 | 99 | | 80 | 11,N |
| Q | MEL | 75 | 7.1 | LAC | 943.5 | 90.0 | SDS | 31.5 | 3 | | | | | | | 30 | 0.129 | 78 | 94 | | 100 | | | 89 | 1,M |
| R | MEL | 71.6 | 6.8 | LAC | 946.9 | 90.2 | SDS | 31.5 | 3 | | | | | | | 30 | 0.312 | 72 | 89 | 94 | 94 | 96 | | 92 | 1,F |
| S | IND | 120 | 12 | LAC | 435 | 43.5 | SDS | 10 | 1 | | | | TA | 435 | 43.5 | 44 | 0.168 | 60 | 79 | 92 | 98 | 100 | | 80 | 11,K |

Figure 9A

| Sample No. | Active material Name | Active material Mass (g) | Active material w/w % | Primary Matrix Name | Primary Matrix Mass (g) | Primary Matrix w/w % | Surfactant #1 Name | Surfactant #1 Mass (g) | Surfactant #1 w/w % | Surfactant #2 Name | Surfactant #2 Mass (g) | Surfactant #2 w/w % | 2nd Matrix Name | 2nd Matrix Mass (g) | 2nd Matrix w/w % | Time (mins.) | D(0.5) µm | %<0.20 µm | %<0.30 µm | %<0.5 µm | %<1.0 µm | %<2.0 µm | No.Ave.(nm) | Yield (%) | Variations |
|---|---|---|---|---|---|---|---|---|---|---|---|---|---|---|---|---|---|---|---|---|---|---|---|---|---|
| T | IND | 130 | 13 | LAC | 645 | 64.5 | SDS | 10 | 1 | | | | TA | 215 | 21.5 | 36 | 0.160 | 63 | 79 | 93 | 97 | 99 | | | 11 |
| U | IND | 130 | 13 | LAC | 645 | 64.5 | SDS | 10 | 1 | | | | TA | 215 | 21.5 | 36 | 0.179 | 56 | 72 | 89 | 95 | 97 | | | 11 |
| V | IND | 130 | 13 | LAC | 645 | 64.5 | SDS | 10 | 1 | | | | TA | 215 | 21.5 | 40 | 0.182 | 55 | 70 | 83 | 87 | 92 | | | 11 |
| W | DIC | 150 | 15 | LAC | 840 | 84 | SDS | 10 | 1 | | | | | | | 36 | 0.183 | 55 | 72 | 91 | 96 | 97 | | | 11 |
| X | DIC | 150 | 15 | LAC | 840 | 84 | SDS | 10 | 1 | | | | | | | 36 | 0.186 | 54 | 74 | 94 | 98 | 99 | | | 11 |
| Y | DIC | 150 | 15 | LAC | 840 | 84 | SDS | 10 | 1 | | | | | | | 36 | 0.203 | 49 | 69 | 92 | 97 | 98 | | | 11 |
| Z | NAA | 334 | 35.1 | MAN | 599 | 62.9 | SDS | 9.55 | 1.0 | PVP | 9.55 | 1.0 | | | | 60 | 0.399 | 33 | 44 | 53 | 59 | 69 | | | |
| AA | NAA | 334 | 35.1 | MAN | 599 | 62.9 | SDS | 9.55 | 1.0 | PVP | 9.55 | 1.0 | | | | 60 | 0.337 | 34 | 47 | 58 | 65 | 71 | | | |
| AB | NAA | 334 | 35.1 | MAN | 599 | 62.9 | SDS | 9.55 | 1.0 | PVP | 9.55 | 1.0 | | | | 60 | 0.300 | 37 | 50 | 61 | 69 | 76 | | | |
| AC | NAA | 334 | 35.1 | MAN | 599 | 62.9 | SDS | 9.55 | 1.0 | PVP | 9.55 | 1.0 | | | | 60 | 0.360 | 34 | 46 | 56 | 61 | 69 | | | |
| AD | NAA | 334 | 35.1 | MAN | 599 | 62.9 | SDS | 9.55 | 1.0 | PVP | 9.55 | 1.0 | | | | 60 | 0.366 | 33 | 45 | 55 | 61 | 69 | | | |
| AE | NAA | 334 | 35.1 | MAN | 599 | 62.9 | SDS | 9.55 | 1.0 | PVP | 9.55 | 1.0 | | | | 60 | 0.301 | 36 | 50 | 62 | 69 | 75 | | | |
| AF | NAA | 334 | 35.1 | MAN | 599 | 62.9 | SDS | 9.55 | 1.0 | PVP | 9.55 | 1.0 | | | | 60 | 0.298 | 37 | 50 | 62 | 68 | 74 | | | |
| AG | NAA | 334 | 35.1 | MAN | 599 | 62.9 | SDS | 9.55 | 1.0 | PVP | 9.55 | 1.0 | | | | 60 | 0.195 | 51 | 65 | 74 | 78 | 83 | | | |
| AH | NAA | 334 | 35.1 | MAN | 599 | 62.9 | SDS | 9.55 | 1.0 | PVP | 9.55 | 1.0 | | | | 60 | 0.294 | 37 | 51 | 62 | 68 | 76 | | | |
| AI | MEL | 105 | 11 | LAC | 864 | 86.4 | SDS | 31.5 | 3 | | | | | | | 20 | 0.189 | 53 | 72 | 84 | 88 | 94 | | | F |
| AJ | MEL | 105 | 11 | LAC | 864 | 86.4 | SDS | 31.5 | 3 | | | | | | | 25 | 0.153 | 65 | 84 | 94 | 95 | 98 | | | F |
| AK | MEL | 105 | 11 | LAC | 864 | 86.4 | SDS | 31.5 | 3 | | | | | | | 30 | 0.138 | 74 | 91 | 96 | 96 | 97 | | | F |
| AL | MEL | 105 | 11 | LAC | 864 | 86.4 | SDS | 31.5 | 3 | | | | | | | 35 | 0.126 | 79 | 96 | 100 | 100 | 100 | | 90 | F |

Figure 9B

| Sample No. | Active material | | | | Primary Matrix | | | Surfactant #1 | | | Time (mins.) | Particle Size | | | | | | Yield (%) | Variations |
|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | | D(0.5) μm | % <0.20 μm | % <0.30 μm | % < 0.5 μm | % < 1.0 μm | % < 2.0 μm | | |
| A | DIC | 2.50 | 10 | | MAN | 22.5 | 89 | SDS | 0.25 | 1 | 30 | 0.237 | 40 | 63 | 83 | 93 | 97 | | |
| B | NAA | 70 | 35 | | LAC | 128 | 64 | SDS | 2 | 1 | 60 | 0.224 | 72 | 81 | 92 | 81 | 92 | | |
| C | NAA | 70 | 35 | | MAN | 128 | 64 | SDS | 2 | 1 | 60 | 0.177 | 57 | 74 | 86 | 90 | 93 | | |
| D | NAA | 80 | 40 | 40 | LAC | 118 | 60 | | | | 45 | 2.039 | 19 | 26 | 31 | 36 | 49 | | |
| E | DIC | 1650 | 15 | | LAC | 9240 | 84 | SDS | 110 | 1 | 20 | 0.24 | 42 | 58 | 74 | 86 | 94 | 91 | |
| F | DIC | 3750 | 15 | | LAC | 21000 | 84 | SDS | 250 | 1 | 25 | 0.214 | 49 | 68 | 82 | 93 | 97 | 97 | |

Figure 10A

| Sample No. | Active material Name | Active Mass (g) | Active %w/w | Primary Matrix Name | Primary Mass (g) | Primary %w/w | Surfactant #1 Name | Surfactant Mass (g) | Surfactant %w/w | 2nd Matrix Name | 2nd Mass (g) | 2nd %w/w | 3rd Matrix Name | 3rd Mass (g) | 3rd %w/w | Time (mins.) | D(0.5) μm | % > 1.0 μm | % > 2.0 μm | % > 5.0 μm | % > 10.0 μm | % < 20.0 μm | Yield (%) | Variations |
|---|---|---|---|---|---|---|---|---|---|---|---|---|---|---|---|---|---|---|---|---|---|---|---|---|
| A | COF | 0.5 | 10 | LAC | 4.45 | 89 | LEC | 0.05 | 1 | | | | | | | 300 | 5.766 | 1 | 10 | 43 | 78 | 99 | 68 | 10 |
| B | COF | 1.0 | 20 | LAC | 3.95 | 79 | LEC | 0.05 | 1 | | | | | | | 300 | 4.493 | 1 | 12 | 56 | 89 | 100 | 81 | 10 |
| C | COF | 0.5 | 10 | SUC | 4.45 | 89 | LEC | 0.05 | 1 | | | | | | | 300 | 5.718 | 1 | 9 | 43 | 81 | 100 | 63 | 10 |
| D | COF | 1.0 | 20 | SUC | 3.95 | 79 | LEC | 0.05 | 1 | | | | | | | 300 | 4.094 | 1 | 12 | 63 | 95 | 100 | 79 | 10 |
| E | COF | 1.5 | 30 | SUC | 3.45 | 69 | LEC | 0.05 | 1 | | | | | | | 300 | 3.629 | 1 | 15 | 71 | 97 | 100 | 85 | 10 |
| F | COF | 2.5 | 50 | SUC | 2.45 | 49 | LEC | 0.05 | 1 | | | | | | | 300 | 3.51 | 2 | 18 | 72 | 97 | 100 | 89 | 10 |
| G | COF | 4.95 | 99 | | | | LEC | 0.05 | 1 | | | | | | | 30 | 10.91 | 2 | 12 | 31 | 47 | 77 | 0 | 10 |
| H | COF | 1.0 | 20 | LAC | 1.95 | 39 | LEC | 0.05 | 1 | SUC | 1.0 | 20 | SMP | 1.00 | 20 | 300 | 4.249 | 1 | 14 | 59 | 90 | 99 | 78 | 10 |
| I | CON | 1.0 | 20 | SUC | 2.95 | 59 | LEC | 0.05 | 1 | FCM | 1 | 20 | | | | 300 | 3.241 | 4 | 24 | 74 | 97 | 100 | 90 | 10 |
| J | CON | 1.0 | 20 | SUC | 3.85 | 77 | LEC | 0.15 | 3 | | | | | | | 20.5 | 3.093 | 8 | 28 | 76 | 97 | 100 | 87 | 10 |
| K | COP | 1.5 | 30 | SUC | 3.35 | 67 | LEC | 0.15 | 3 | | | | | | | 20.5 | 2.672 | 6 | 32 | 85 | 99 | 100 | 84 | 10 |
| L | COP | 0.5 | 10 | LAC | 4.45 | 89 | SDS | 0.05 | 1 | | | | | | | 120 | 0.833 | 53 | 71 | 91 | 96 | 99 | 21 | 10 |
| M | COP | 0.5 | 10 | SUC | 4.45 | 89 | SDS | 0.05 | 1 | | | | | | | 120 | 1.552 | 37 | 59 | 87 | 95 | 97 | 50 | 10 |
| N | COP | 0.5 | 10 | LFG | 4.45 | 89 | LEC | 0.05 | 1 | | | | | | | 150 | 0.299 | 62 | 70 | 83 | 87 | 90 | 41 | 10 |
| O | COP | 0.5 | 10 | LFG | 4.45 | 89 | LEC | 0.05 | 1 | | | | | | | 150 | 0.96 | 51 | 66 | 88 | 95 | 98 | 60 | 10 |
| P | COP | 0.75 | 15 | SUC | 4.2 | 84 | LEC | 0.05 | 1 | | | | | | | 180 | 1.071 | 49 | 66 | 90 | 97 | 99 | 74 | 10 |
| Q | COP | 1.0 | 20 | SUC | 3.95 | 79 | LEC | 0.05 | 1 | | | | | | | 180 | 1.433 | 39 | 62 | 91 | 100 | 100 | 69 | 10 |
| R | COP | 0.5 | 10 | WP | 4.45 | 89 | SDS | 0.05 | 1 | | | | | | | 60 | 1.671 | 24 | 60 | 94 | 100 | 100 | 17 | 10 |
| S | COP | 0.5 | 10 | WP | 4.50 | 90 | | | | | | | | | | 60 | 1.944 | 18 | 52 | 91 | 99 | 100 | 44 | 10 |

Figure 11A

| Sample No. | Active material | | | Primary Matrix | | | Surfactant #1 | | | Time (mins.) | Particle Size | | | | | | Yield (%) | Variations |
|---|---|---|---|---|---|---|---|---|---|---|---|---|---|---|---|---|---|---|
| | Name | Mass (g) | % w/w | Name | Mass (g) | % w/w | Name | Mass (g) | % w/w | | D(0.5) μm | % < 1.0 μm | % < 2.0 μm | % < 5.0 μm | % < 10.0 μm | % < 20.0 μm | | |
| T | GIN | 0.5 | 10 | LAC | 4.45 | 89 | LEC | 0.05 | 1 | 30 | 11.52 | 0 | 0 | 10 | 42 | 80 | 93 | 5 |
| U | GIN | 0.5 | 10 | SUC | 4.45 | 89 | LEC | 0.05 | 1 | 30 | 10.08 | 0 | 0 | 13 | 50 | 86 | 72 | 5 |
| V | GIN | 1 | 20 | LAC | 3.95 | 79 | LEC | 0.05 | 1 | 30 | 11.58 | 0 | 0 | 12 | 42 | 78 | 90 | 5 |
| W | GIN | 1 | 20 | SUC | 3.95 | 79 | LEC | 0.05 | 1 | 30 | 10.88 | 0 | 0 | 13 | 45 | 80 | 96 | 5 |
| X | RAS | 3 | 30 | LAC | 6.9 | 69 | LEC | 0.1 | 1 | 60 | 6 | 4 | 11 | 41 | 74 | 94 | 95 | 5 |
| Y | RAS | 1 | 10 | SUC | 8.9 | 89 | LEC | 0.1 | 1 | 60 | 5.84 | 4 | 11 | 42 | 76 | 95 | 94 | 5 |
| Z | RAS | 5 | 50 | SUC | 4.9 | 49 | LEC | 0.1 | 1 | 60 | 5.995 | 3 | 11 | 42 | 71 | 88 | 98 | 5 |
| AA | RAS | 7.5 | 75 | SUC | 2.4 | 24 | LEC | 0.1 | 1 | 60 | 6.374 | 2 | 9 | 39 | 69 | 87 | 99 | 5 |
| AB | RAS | 9.9 | 99 | | | | LEC | 0.1 | 1 | 60 | 7.405 | 1 | 5 | 31 | 63 | 85 | 100 | 5 |
| AC | RAS | 3 | 30 | SUC | 6.7 | 67 | LEC | 0.3 | 3 | 60 | 4.917 | 3 | 15 | 51 | 80 | 96 | 99 | 5 |

Figure 11B

| Sample No. | Active material | | | Primary Matrix | | | Surfactant #1 | | | Time (mins.) | Particle Size | | | | | | Yield (%) | Variations |
|---|---|---|---|---|---|---|---|---|---|---|---|---|---|---|---|---|---|---|
| | Name | Mass (g) | % w/w | Name | Mass (g) | % w/w | Name | Mass (g) | % w/w | | D(0.5) μm | % < 1.0 μm | % < 2.0 μm | % < 5.0 μm | % < 10.0 μm | % < 20.0 μm | | |
| AD | FEN | 1 | 20 | SUC | 3.91 | 78 | LEC | 0.10 | 2.0 | 60 | 7.367 | 3 | 9 | 34 | 62 | 83 | 95 | 5 |
| AE | LIN | 1 | 20 | SUC | 3.90 | 78 | LEC | 0.11 | 2.0 | 60 | 3.141 | 20 | 37 | 64 | 81 | 94 | 99 | 5 |
| AG | GOJ | 1 | 20 | SUC | 3.91 | 78 | LEC | 0.11 | 2.0 | 60 | 9.573 | 2 | 6 | 26 | 52 | 73 | 88 | 5 |
| AH | GTE | 1 | 20 | SUC | 3.91 | 78 | LEC | 0.10 | 2.0 | 60 | 3.241 | 14 | 30 | 70 | 90 | 95 | 93 | 5 |
| AI | CLO | 1 | 20 | SUC | 3.90 | 78 | LEC | 0.1 | 2.0 | 60 | 3.862 | 4 | 16 | 66 | 94 | 100 | 98 | 5 |
| AJ | APR | 1 | 20 | SUC | 3.89 | 78 | LEC | 0.1 | 2.0 | 60 | 2.995 | 16 | 35 | 71 | 89 | 95 | 96 | 5 |
| AK | PEA | 1 | 20 | SUC | 3.90 | 78 | LEC | 0.1 | 2.0 | 60 | 7.009 | 1 | 4 | 31 | 71 | 96 | 94 | 5 |
| AL | BEA | 1 | 20 | SUC | 3.91 | 78 | LEC | 0.11 | 2.0 | 60 | 10.59 | 1 | 2 | 16 | 47 | 82 | 95 | 5 |
| AM | RAS | 3 | 30 | SUC | 6.80 | 78 | LEC | 0.2 | 2.0 | 60 | 5.143 | 5 | 16 | 49 | 80 | 96 | 96 | 5 |
| AN | RAS | 3 | 30 | SUC | 6.51 | 78 | LEC | 0.5 | 5.0 | 60 | 5.403 | 3 | 13 | 46 | 76 | 94 | 97 | 5 |
| AO | LAV | 1 | 20 | SC | 3.93 | 78 | SDS | 0.1 | 2.0 | 60 | 4.632 | 5 | 17 | 54 | 83 | 95 | 94 | 5 |
| AP | LAV | 1 | 20 | SC | 3.91 | 78 | B700 | 0.1 | 2.0 | 60 | 4.782 | 6 | 16 | 52 | 84 | 99 | 92 | 5 |
| AQ | GOJ | 5.1 | 100 | | | | | | | 60 | 61.37 | 1 | 3 | 8 | 14 | 24 | | 5 |
| AR | MST | 1 | 20 | SUC | 3.90 | 78 | LEC | 0.1 | 2.0 | 60 | 4.656 | 5 | 19 | 53 | 75 | 92 | 93 | 5 |
| AS | CNG | 1 | 20 | SUC | 3.90 | 78 | LEC | 0.1 | 2.0 | 60 | 3.135 | 14 | 34 | 66 | 83 | 92 | 93 | 5 |
| AT | CNQ | 1 | 20 | SUC | 3.91 | 78 | LEC | 0.1 | 2.0 | 60 | 5.082 | 4 | 16 | 49 | 72 | 89 | 93 | 5 |
| AU | TUR | 1 | 20 | SUC | 3.90 | 78 | LEC | 0.11 | 2.0 | 60 | 14.88 | 1 | 3 | 15 | 35 | 62 | 96 | 5 |
| AV | TUR | 1 | 20 | LAC | 3.91 | 78 | LEC | 0.11 | 2.0 | 60 | 14.66 | 1 | 3 | 16 | 35 | 63 | 96 | 5 |

Figure 11C

| Sample No. | Active material Name | Active material Mass (g) | Active material w/w % | Primary Matrix Name | Primary Matrix Mass (g) | Primary Matrix w/w % | Surfactant #1 Name | Surfactant #1 Mass (g) | Surfactant #1 w/w % | 2nd Matrix Name | 2nd Matrix Mass (g) | 2nd Matrix w/w % | 3rd Matrix Name | 3rd Matrix Mass (g) | 3rd Matrix w/w % | Time (mins.) | D(0.5) µm | % < 1.0 µm | % < 2.0 µm | % < 5.0 µm | % < 10.0 µm | % < 20.0 µm | Yield (%) | Variations |
|---|---|---|---|---|---|---|---|---|---|---|---|---|---|---|---|---|---|---|---|---|---|---|---|---|
| A | COF | 105 | 30 | SUC | 241.5 | 69 | LEC | 3.5 | 1 | | | | | | | 60 | 7.736 | 2 | 11 | 32 | 63 | 94 | | 10 |
| B | COF | 336.5 | 99 | | | | LEC | 3.5 | 1 | | | | | | | 60 | 7.531 | 2 | 12 | 38 | 58 | 78 | 94 | 10 |
| C | CON | 60 | 30 | SUC | 134 | 67 | LEC | 6 | 3 | | | | | | | 10 | 4.701 | 3 | 14 | 53 | 84 | 97 | 75 | 10,B |
| D | CON | 40 | 20 | SUC | 84 | 42 | LEC | 6 | 3 | FCM | 50 | 25 | LFG | 20 | 10 | 5 | 3.873 | 5 | 21 | 62 | 88 | 98 | 83 | 10,B |
| E | COP | 35 | 10 | LFG | 311.5 | 89 | SDS | 3.5 | 1 | | | | | | | 45 | 4.246 | 3 | 17 | 59 | 91 | 100 | 74 | 10 |
| F | COP | 35 | 10 | SUC | 311.5 | 89 | LEC | 3.5 | 1 | | | | | | | 300 | 1.417 | 39 | 63 | 90 | 96 | 99 | 84 | 10 |

Figure 12A

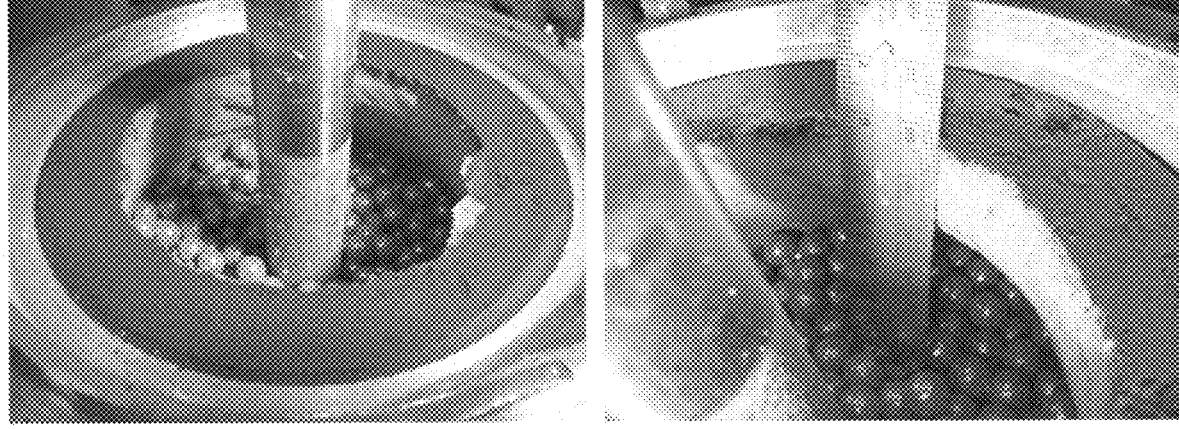
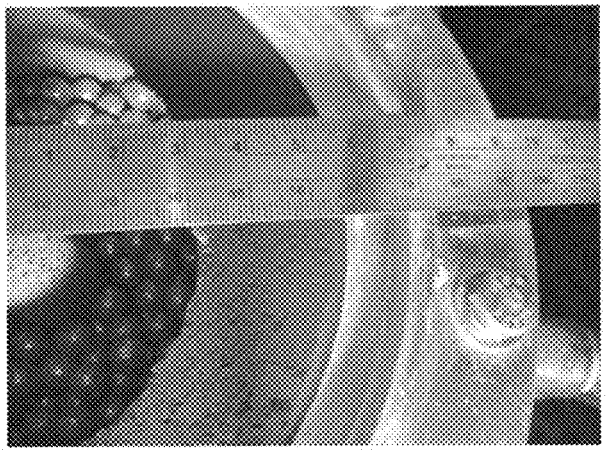
Figure 12B

| Sample No. | Active material |  |  |  | Primary Matrix |  |  | Surfactant #1 |  |  | Surfactant #2 |  |  | Surfactant #3 |  |  | Disintegrant |  |  | Time (mins.) | Particle Size |  |  |  |  |  | Yield (%) | Variations |
|---|---|---|---|---|---|---|---|---|---|---|---|---|---|---|---|---|---|---|---|---|---|---|---|---|---|---|---|---|
|  | Name | Mass (g) | % w/w | % v/v | Name | Mass (g) | % w/w | Name | Mass (g) | % w/w | Name | Mass (g) | % w/w | Name | Mass (g) | % w/w | Name | Mass (g) | % w/w |  | D(0.5) μm | % <0.20 μm | % <0.30 μm | % >0.5 μm | % >1.0 μm | % >2.0 μm |  |  |
| A | NAA | 105 | 35 | 39 | MAN | 189 | 63 | SDS | 3 | 1 | P3000 | 3 | 1 |  |  |  |  |  |  | 80 | 0.19 | 53 | 71 | 84 | 91 | 95 | 90 |  |
| B | NAA | 105 | 35 | 39 | MAN | 189 | 63 | SDS | 3 | 1 | P407 | 3.1 | 1 |  |  |  |  |  |  | 40 | 0.89 | 26 | 36 | 45 | 51 | 57 |  |  |
| C | NAA | 105 | 35 | 39 | MAN | 189 | 63 | SDS | 3 | 1 | P407 | 3.1 | 1 |  |  |  |  |  |  | 60 | 0.31 | 36 | 49 | 61 | 69 | 76 |  |  |
| D | NAA | 105 | 35 | 39 | MAN | 189 | 63 | SDS | 3 | 1 | P407 | 3.1 | 1 |  |  |  |  |  |  | 80 | 0.19 | 52 | 70 | 84 | 90 | 93 | 82 |  |
| E | NAA | 105.1 | 35 | 39 | MAN | 192 | 64 | SDS | 3 | 1 |  |  |  |  |  |  |  |  |  | 80 | 0.24 | 43 | 59 | 72 | 78 | 81 | 84.6 |  |
| F | NAA | 105 | 35 | 39 | MAN | 171 | 57 | SDS | 3 | 1 | P3000 | 3 | 1 | PVP | 3 | 1 | PML | 15 | 5 | 80 | 0.27 | 39 | 54 | 67 | 74 | 78 | 89.2 | 12 |
| G | NAA | 105 | 35 | 39 | MAN | 171 | 57 | SDS | 3 | 1 | P407 | 3 | 1 | PVP | 3.02 | 1 | PML | 15.1 | 5 | 80 |  |  |  |  |  |  | 88.2 |  |
| H | NAA | 105.2 | 35 | 39 | MAN | 174 | 58 | SDS | 3 | 1 | PVP | 3 | 1 |  |  |  | PML | 15.0 | 5 | 80 |  |  |  |  |  |  | 87.1 |  |
| I | NAA | 105 | 35 | 39 | MAN | 189 | 63 | SDS | 3 | 1 | P3000 | 3 | 1 | PVP | 3.01 | 1 |  |  |  | 80 | 0.25 | 27 | 67 | 91 | 100 | 100 | 88 |  |
| J | NAA | 105.7 | 35 | 39 | MAN | 186 | 62 | SDS | 3 | 1 | P3000 | 3 | 1 |  |  |  |  |  |  | 80 | 0.24 | 29 | 68 | 90 | 99 | 100 | 89.7 |  |
| K | NAA | 105.1 | 35.0 | 39 | MAN | 195 | 65.0 |  |  |  |  |  |  |  |  |  |  |  |  | 80 | 0.19 | 53 | 70 | 82 | 87 | 91 | 81 |  |
| L | NAA | 105 | 35.0 |  | MAN | 180 | 60.0 |  |  |  |  |  |  |  |  |  | MCC | 15 | 5 | 80 | 0.26 | 40 | 54 | 65 | 69 | 75 | 66 | 12,D |
| M | NAA | 105 | 35.0 |  | MAN | 180 | 60.0 |  |  |  |  |  |  |  |  |  | PML | 15 | 5 | 80 | 0.24 | 42 | 58 | 69 | 76 | 85 | 51 | 12,D |

Figure 13A

| Sample No. | Active material Name | Mass (g) | % w/w | Primary Matrix Name | Mass (g) | % w/w | Surfactant #1 Name | Mass (g) | % w/w | Surfactant #2 Name | Mass (g) | % w/w | Time (mins.) | D(0.5) µm | % <0.20 µm | % <0.30 µm | % < 0.5 µm | % < 1.0 µm | % < 2.0 µm | Yield (%) | Variations |
|---|---|---|---|---|---|---|---|---|---|---|---|---|---|---|---|---|---|---|---|---|---|
| A | NAA | 1.5 | 30 | LAC | 3.2 | 64 | SDS | 0.05 | 1 | MCC | 0.25 | 5 | 40 | 2.6 | 29 | 41 | 47 | 61 | 77 | 86 | |
| B | 14A | | | | | | | | | | | | | 0.2 | 68 | 79 | 84 | 94 | 99 | | 12 |
| C | NAA | 1.5 | 30 | LAC | 3.45 | 69 | SDS | 0.05 | 1 | | | | 40 | 0.2 | 79 | 95 | 98 | 100 | 100 | 95 | |
| D | 14C | 2.5 | 95 | MCC | 0.13 | 5 | | | | | | | 1 | 0.2 | 80 | 94 | 97 | 100 | 100 | | 12 |
| E | 14C | 2.5 | 91 | MCC | 0.25 | 9 | | | | | | | 1 | 1.3 | 34 | 49 | 52 | 56 | 60 | 88 | |
| F | 14C | | | | | | | | | | | | | 0.8 | 36 | 52 | 56 | 62 | 72 | 83 | |
| G | 14E | | | | | | | | | | | | | 0.2 | 79 | 92 | 96 | 99 | 100 | | 12 |
| H | 14F | | | | | | | | | | | | | 0.2 | 79 | 93 | 97 | 99 | 100 | | 12 |
| I | NAA | 1.5 | 30 | LAC | 2.95 | 59 | SDS | 0.05 | 1 | MCC | 0.5 | 10 | 40 | 6.4 | 12 | 19 | 25 | 43 | 64 | 96 | |
| J | NAA | 1.5 | 30 | LAC | 2.45 | 49 | SDS | 0.05 | 1 | MCC | 1 | 20 | 40 | 8.6 | 0 | 0 | 7 | 31 | 56 | 95 | |
| K | 14I | | | | | | | | | | | | | 1.7 | 32 | 44 | 53 | 77 | 94 | | 12 |
| L | 14J | | | | | | | | | | | | | 4.1 | 0 | 0 | 12 | 61 | 92 | | 12 |

Figure 14A

| Sample No. | Active material Name | Active material Mass (g) | Active material % w/w | Primary Matrix Name | Primary Matrix Mass (g) | Primary Matrix % w/w | Surfactant #1 Name | Surfactant #1 Mass (g) | Surfactant #1 % w/w | 2nd Matrix Name | 2nd Matrix Mass (g) | 2nd Matrix % w/w | Time (mins.) | D(0.5) μm | % <0.20 μm | % <0.30 μm | % > 0.5 μm | % > 1.0 μm | % > 2.0 μm | Variations |
|---|---|---|---|---|---|---|---|---|---|---|---|---|---|---|---|---|---|---|---|---|
| A | G | 71.6 | 6.8 | LAC | 946.9 | 90.2 | S | 31.5 | 3.3 | | | | 20 | 0.116 | 86 | 96 | 96 | 96 | 96 | G |
| B | G | 71.6 | 6.8 | LAC | 946.9 | 90.2 | S | 31.5 | 3.3 | | | | 37 | 0.251 | 79 | 96 | 100 | 100 | 100 | 1,F |
| C | H | 71.6 | 6.8 | LAC | 946.9 | 90.2 | S | 31.5 | 3.3 | | | | 30 | 0.312 | 72 | 89 | 94 | 94 | 96 | 1,F |
| D | | | | LAC | 315.6 | 96.8 | S | 10.5 | 3.2 | | | | 30 | | | | | | | D |
| E | G | 0.68 | 6.8 | D | 9.32 | 93.2 | S | | | | | | | | | | | | | |
| F | H | 0.68 | 6.8 | D | 9.32 | 93.2 | S | | | | | | | | | | | | | |
| G | Mel | | | | | | | | | | | | | 8.791 | 0 | 0 | 0 | 1.8 | 7.11 | 1 |
| H | Mel | | | | | | | | | | | | | 2.824 | 0 | 0 | 0 | 2 | 26 | 1 |
| I | N | 112.4 | 13.0 | LAC | 741.0 | 74.1 | S | 11.0 | 1.1 | TA | 247.0 | 24.7 | | 1.075 | 12 | 18 | 27 | 47 | 76 | |
| J | IND | 130.0 | 13.0 | I | 752.4 | 87.0 | | | | | | | | | | | | | | |
| K | IND | 130.0 | 13.0 | LAC | 645.0 | 64.5 | S | 10.0 | 1.0 | TA | 215.0 | 21.5 | | 0.21 | 48 | 62 | 71 | 78 | 93 | |
| L | IND | 130.0 | 13.0 | LAC | 645.0 | 64.5 | S | 10.0 | 1.0 | TA | 215.0 | 21.5 | | 1.075 | 12 | 18 | 27 | 47 | 76 | |
| M | IND | | | | | | | | | | | | | | | | | | | |
| N | | | | | | | | | | | | | 20 | 5.253 | 0 | 0 | 0 | 1 | 60 | A |
| O | MEL | 20.0 | 20.0 | LAC | 77.0 | 77.0 | S | 3.0 | 3.0 | | | | 15 | 0.255 | 36 | 60 | 83 | 95 | | |
| P | MEL | 15.0 | 15.0 | LAC | 82.0 | 82.0 | S | 3.0 | 3.0 | | | | 30 | 0.2 | 45 | 67 | 86 | 96 | | |
| Q | MEL | 10.0 | 10.0 | LAC | 87.0 | 87.0 | S | 3.0 | 3.0 | | | | 60 | 0 | 28 | 47 | 73 | 92 | | |
| R | SAL | 3.0 | 1.0 | LAC | 294 | 98 | LEC | 3.0 | 1.0 | | | | 30 | | | | | | | |
| S | SAL | 3.0 | 1.0 | LAC | 294.1 | 98 | T80 | 3.3 | 1.0 | | | | 20 | | | | | | | |
| T | SAL | 3.0 | 1.0 | LAC | 294 | 98 | LEC | 3.0 | 1.0 | | | | | | | | | | | |

Figure 15

| Sample Number | Powder Adherence ~ Residual mass (mg) | | | | | Powder Flow - Angle of Repose (θ°) | | Dry powder particle size | | | | | | |
|---|---|---|---|---|---|---|---|---|---|---|---|---|---|---|
| | mean | %RSD | mean | %RSD | mean | mean | %RSD | d (0.1) | d (0.5) | d (0.9) | D [4, 3] | % < 2.0 µm | % > 10.0 µm | % < 20.0 µm |
| B | 2.3 | 84.56 | 9.1 | 7.9 | 3 | | | 0.9 | 11.0 | 70.1 | 23.2 | 17.8 | 52.7 | 67.2 |
| C | 1.3 | 31.22 | 3.8 | 86.6 | 4 | | | 0.8 | 10.2 | 67.6 | 21.6 | 18.6 | 50.6 | 70.1 |
| E | 3.4 | 34.43 | 18.4 | 23.7 | 28 | | | | | | | | | |
| F | 3.9 | 54.84 | 10.5 | 37.6 | 42 | | | | | | | | | |
| G | 7.7 | 33.35 | 6.1 | 26.8 | 381 | | | 1.2 | 6.2 | 19.9 | 9.5 | 15.4 | 30.2 | 90.1 |
| H | 18 | 86.2 | 69.7 | 97.4 | 54 | | | | | | | | | |
| J | 5.5 | 54.38 | 13.4 | 13.2 | 7 | 43 | 15.7 | 1.3 | 13.6 | 103.2 | 39.9 | 14.7 | 56.3 | 58.1 |
| K | 3.3 | 61.94 | 8.2 | 16 | 5 | 35 | 15.8 | 1.3 | 11.4 | 58.0 | 21.1 | 13.8 | 53.5 | 65.5 |
| L | 11.7 | 61.85 | 4.3 | 23.6 | 56 | 26 | 4.8 | 0.6 | 1.5 | 3.3 | 1.7 | 66.1 | 0.0 | 100.0 |
| M | 10.9 | 52.93 | 38.3 | 66.9 | 83 | 43 | 5.1 | 0.5 | 2.0 | 5.3 | 2.5 | 50.8 | 0.6 | 100.0 |
| O | | | | | | | | 0.7 | 6.5 | 57.3 | 21.1 | 25.0 | 40.6 | 73.4 |
| P | | | | | | | | 0.7 | 5.9 | 49.6 | 18.7 | 27.0 | 38.2 | 76.0 |
| Q | | | | | | | | 0.8 | 6.8 | 50.9 | 20.9 | 24.2 | 41.2 | 74.4 |
| S | | | | | | | | 1.3 | 8.4 | 42.2 | 15.5 | 13.7 | 44.1 | 74.2 |
| T | | | | | | | | 1.3 | 12.5 | 61.7 | 23.1 | 14.0 | 55.1 | 61.4 |

Figure 16

| Sample Number | Average Bulk Density (g/mL) | Average Tap Density (g/mL) | Basic Flow Energy (BFE) (mJ) | Specific Energy (SE) (mJ/g) | PD15 (mBar) | CPS18 (%) |
|---|---|---|---|---|---|---|
| B | 0.42 | 0.77 | | | | |
| C | 0.43 | 0.80 | | | | |
| E | 0.40 | 0.85 | | | | |
| F | 0.43 | 0.91 | | | | |
| G | 0.45 | 0.89 | | | | |
| H | 0.26 | 0.51 | | | | |
| J | 0.47 | 0.71 | 445 | 9 | 21 | 24 |
| K | 0.47 | 0.73 | 370 | 7 | 6 | 17 |
| L | 0.23 | 0.34 | 692 | 15 | 47 | 27 |
| N | 0.19 | 0.3 | 654 | 16 | 14 | 37 |

METHOD FOR THE PRODUCTION OF COMMERCIAL NANOPARTICLE AND MICROPARTICLE POWDERS

RELATED APPLICATIONS

This application is a continuation of U.S. application Ser. No. 16/880,931, filed on May 21, 2020, (now abandoned) which is a continuation of U.S. application Ser. No. 15/387, 541, filed on Dec. 21, 2016, (now abandoned) which is a continuation of U.S. application Ser. No. 14/279,185, filed on May 15, 2014, (now abandoned) which is a continuation of U.S. application Ser. No. 13/265,933, filed on Mar. 9, 2012, (now abandoned) which is a U.S. national stage under 35 USC § 371 of International Application Number PCT/ AU2010/000467, filed on 23 Apr. 2010, which claims priority to AU Application No. 2009901747, filed on 24 Apr. 2009 and U.S. Application No. 61/172,300, filed on 24 Apr. 2009, the entire contents of which applications is hereby incorporated by reference.

FIELD OF THE INVENTION

The present invention relates to methods for producing nanoparticle and microparticle powders of a biologically active material using dry milling processes, as well as compositions comprising such materials, medicaments produced using said biologically active materials in particulate form and/or compositions, and to methods of treatment of an animal, including man, using a therapeutically effective amount of said biologically active materials administered by way of said medicaments. Compositions of the present invention have unexpectedly improved powder handling properties relative to compositions made by conventional techniques, making them advantageous for use in commercial applications.

BACKGROUND

Poor bioavailability is a significant problem encountered in the development of compositions in the therapeutic, cosmetic, agricultural and food industries, particularly those materials containing a biologically active material that is poorly soluble in water at physiological pH. An active material's bioavailability is the degree to which the active material becomes available to the target tissue in the body or other medium after systemic administration through, for example, oral or intravenous means. Many factors affect bioavailability, including the form of dosage and the solubility and dissolution rate of the active material.

In therapeutic applications, poorly and slowly water-soluble materials tend to be eliminated from the gastrointestinal tract before being absorbed into the circulation. In addition, poorly soluble active agents tend to be disfavored or even unsafe for intravenous administration due to the risk of particles of agent blocking blood flow through capillaries.

It is known that the rate of dissolution of a particulate drug will increase with increasing surface area. One way of increasing surface area is decreasing particle size. Consequently, methods of making finely divided or sized drugs have been studied with a view to controlling the size and size range of drug particles for pharmaceutical compositions.

For example, dry milling techniques have been used to reduce particle size and hence influence drug absorption. However, in conventional dry milling the limit of fineness is reached generally in the region of about 100 microns (100, 000 nm), at which point material cakes on the milling chamber and prevents any further diminution of particle size. Alternatively, wet grinding may be employed to reduce particle size, but flocculation restricts the lower particle size limit to approximately 10 microns (10,000 nm). The wet milling process, however, is prone to contamination, thereby leading to a bias in the pharmaceutical art against wet milling. Another alternative milling technique, commercial airjet milling, has provided particles ranging in average size from as low as about 1 to about 50 microns (1,000-50,000 nm).

There are several approaches currently used to formulate poorly soluble active agents. One approach is to prepare the active agent as a soluble salt. Where this approach cannot be employed, alternate (usually physical) approaches are employed to improve the solubility of the active agent. Alternate approaches generally subject the active agent to physical conditions that change the agent's physical and or chemical properties to improve its solubility. These include process technologies such as micronization, modification of crystal or polymorphic structure, development of oil based solutions, use of co-solvents, surface stabilizers or complexing agents, micro-emulsions, super-critical fluid and production of solid dispersions or solutions. More than one of these processes may be used in combination to improve formulation of a particular therapeutic material. Many of these approaches commonly convert a drug into an amorphous state, which generally leads to a higher dissolution rate. However, formulation approaches that result in the production of amorphous material are not common in commercial formulations due to concerns relating to stability and the potential for material to re-crystallize.

These techniques for preparing such pharmaceutical compositions tend to be complex. By way of example, a principal technical difficulty encountered with emulsion polymerization is the removal of contaminants, such as unreacted monomers or initiators (which may have undesirable levels of toxicity), at the end of the manufacturing process.

Another method of providing reduced particle size is the formation of pharmaceutical drug microcapsules, which techniques include micronizing, polymerisation and co-dispersion. However, these techniques suffer from a number of disadvantages including at least the inability to produce sufficiently small particles such as those obtained by milling, and the presence of co-solvents and/or contaminants such as toxic monomers which are difficult to remove, leading to expensive manufacturing processes.

Over the last decade, intense scientific investigation has been carried out to improve the solubility of active agents by converting the agents to ultra fine powders by methods such as milling and grinding. These techniques may be used to increase the dissolution rate of a particulate solid by increasing the overall surface area and decreasing the mean particle size.

U.S. Pat. No. 6,634,576 discloses examples of wet-milling a solid substrate, such as a pharmaceutically active compound, to produce a "synergetic co-mixture".

International Patent Application PCT/AU2005/001977 (Nanoparticle Composition(s) and Method for Synthesis Thereof) describes, inter alia, a method comprising the step of contacting a precursor compound with a co-reactant under mechanochemical synthesis conditions wherein a solid-state chemical reaction between the precursor compound and the co-reactant produces therapeutically active nanoparticles dispersed in a carrier matrix. Mechanochemical synthesis, as discussed in International Patent Application PCT/AU2005/ 001977, refers to the use of mechanical energy to activate, initiate or promote a chemical reaction, a crystal structure transformation or a phase change in a material or a mixture of materials, for example by agitating a reaction mixture in the presence of a milling media to transfer mechanical energy to the reaction mixture, and includes without limitation "mechanochemical activation", "mechanochemical processing", "reactive milling", and related processes.

International Patent Application PCT/AU2007/000910 (Methods for the preparation of biologically active compounds in nanoparticulate form) describes, inter alia, a method for dry milling raloxifene with lactose and NaCl which produced nanoparticulate raloxifene without significant aggregation problems.

Critical to the successful commercialization of such technology is the ability to easily and cheaply process the materials into final formulations such as tablets or hard gelatin capsules. Many of the technologies discussed above require the particles to be produced in a liquid suspension such that expensive and complicated further processing is needed to make common dry formulations such as tablets.

Some technologies such as micronization do produce material in a dry form, but the particles have inherently high cohesiveness and high static charge. This leads to poor product flow and high aggregation properties. The product fails to flow smoothly into containers (such as capsules) and aggregates significantly when poured. It also adheres significantly to process equipment and containers, thus resulting in a significant loss of product. One solution adopted by the prior art is to bind the material to a carrier product or to dissolve the material in a solution to improve product handling, but these steps add to the overall expense of any process.

Fukami et al (Fukami et al. A nanoparticle processing in solid state dramatically increases the cell membrane permeation of a cholesterol lowering drug, Probucol. *Mol. Pharmaceutics*, accepted Apr. 1, 2009) describe a process for manufacturing nanoparticles of probucol which has a number of limitations. Firstly, the nanoparticles produced by the Fukami process are sticky and difficult to handle. Secondly, to overcome this problem the particles had to be dispersed in water and spray coated onto a carrier particle. The spray coating process, which uses significant amounts of energy, is expensive and adds to the overall cost of the manufacturing.

The present invention provides methods for overcoming the problems identified by the prior art by providing a milling process that produces nanoparticles or microparticles of a biologically active material with powder handling characteristics superior to powders made by conventional size reduction processes.

One limitation of many of the prior art processes is that they are not suitable for commercial scale.

The present invention provides methods for overcoming the problems identified by the prior art by providing a milling process that produces small particles easily and economically even at high volume commercial scale.

One example of a therapeutic area where this technology could be applied in is the area of acute pain management. Many pain medications such as meloxicam (marketed as Mobic® by pharmaceutical company Boehringer Ingelheim) provides pain relief for chronic pain, but must be taken on a daily basis to maintain an effective therapeutic level.

Meloxicam is a poorly water soluble drug which is only slowly absorbed by the body (Tmax is 4-5 hours), so a method such as the present invention which provides for improved dissolution, will likely provide much faster absorption resulting in a more rapid onset of the therapeutic effect. Meloxicam also has a long half life (15-20 hours) that means it only need be taken once a day. By using a method such as the present invention, which provides faster absorption, a drug such as meloxicam, could be transformed from a chronic pain drug to an acute pain drug. For meloxicam this would provide a medication that could provide therapeutic relief for acute pain, with the advantage of sustained pain relief over 24 hours.

Meloxicam also has sub-optimal bioavailability at 89% for an oral capsule, compared with an IV dosage form. A component of this sub optimal bioavailability is also likely due to the poor water solubility of this drug. If the low solubility does contribute to this sub optimal bioavailability, the improvement of the dissolution of this drug with a method such as the present invention could provide scope to produce a dosage form with a lower active dose whilst still providing the effective therapeutic dose.

Although the background to the present invention is discussed in the context of improving the powder handling characteristics of biologically active materials that are poorly or slowly water soluble, the applications of the methods of the present invention are not limited to such, as is evident from the following description of the invention.

Further, although the background to the present invention is largely discussed in the context of improving the powder handling characteristics of therapeutic or pharmaceutical compounds, the applications of the methods of the present invention are clearly not limited to such. For example, as is evident from the following description, applications of the methods of the present invention include but are not limited to: nutraceutical and nutritional compounds, complementary medicinal compounds, veterinary therapeutic applications and agricultural chemical applications, such as pesticide, fungicide or herbicide.

Furthermore an application of the current invention would be to materials which contain a biologically active compound such as, but not limited to a therapeutic or pharmaceutical compound, a nutraceutical or nutrient, a complementary medicinal product such as active components in plant or other naturally occurring material, a veterinary therapeutic compound or an agricultural compound such as a pesticide, fungicide or herbicide. Specific examples would be the spice turmeric that contains the active compound curcumin, or flax seed that contains the nutrient ALA an omega 3 fatty acid. As these specific examples indicate this invention could be applied to, but not limited to, a range of natural products such as seeds, cocoa and cocoa solids, coffee, herbs, spices, other plant materials or food materials that contain a biologically active compound. The application of this invention to these types of materials would enable greater availability of the active compound in the materials when used in the relevant application. For example where material subject to this invention is orally ingested the active would be more bioavailable.

SUMMARY OF THE INVENTION

In one aspect, the present invention is directed to the unexpected discovery of a dry milling process for producing small particles of a material, wherein the powders made by the dry milling process of the present invention have powder handling characteristics that are superior to those of powders made by conventional size reduction processes. In a preferred form of the invention, the material is a biologically active material. In one surprising aspect this can be done at commercial scale. In one surprising aspect the particle size produced by the process is equal to or less than 10,000 nm. In one surprising aspect the particle size produced by the process is equal to or less than 5,000 nm. In one surprising aspect the particle size produced by the process is equal to or less than 2000 nm. In another surprising aspect the particle size produced by the process is equal to or less than 1000 nm. In another surprising aspect the crystallinity of the active material is unchanged or not substantially changed.

Thus in a first aspect, the invention comprises a method for producing nanoparticle and/or microparticle biologically active material with powder handling characteristics superior to powders made by conventional size reduction processes wherein the said method comprises the steps of dry milling a solid biologically active material and a millable grinding matrix in a mill comprising a plurality of milling bodies, for a time period sufficient to produce particles of the biologically active material dispersed in an at least partially milled grinding material. Preferably the biologically active material has a particle size less than 10,000 nm Preferably, the powder handling characteristics of the biologically active material produced by this invention are superior to the powder handling characteristics of a biologically active material with the same, similar or larger particle size manufactured using a conventional process. Preferably, the biologically active material subject to this invention has superior product flow characteristic compared to the product flow characteristic of a biologically active material with the same, similar or larger particle size manufactured using a conventional process. Preferably, the the biologically active material subject to this invention has a lower static charge compared to the static charge of a biologically active material with the same, similar or larger particle size manufactured using a conventional process. Preferably, the biologically active material subject to this invention has a lower cohesiveness profile compared to the cohesiveness profile of a biologically active material with the same, similar or larger particle size manufactured using a conventional process. Preferably, the biologically active material subject to this invention has a lower propensity for aggregation compared to the propensity for aggregation of a biologically active material with the same, similar or larger particle size manufactured using a conventional process. Preferably, the biologically active material subject to this invention has a lower propensity for adherence to other materials compared to the propensity for adherence of a biologically active material with the same, similar or larger particle size manufactured using a conventional process. Preferably, the biologically active material subject to this invention has increased uniformity compared to a biologically active material with the same, similar or larger particle size manufactured using a conventional process. Preferably, the biologically active material subject to this invention has reduced levels of dust compared to a biologically active material with the same, similar or larger particle size manufactured using a conventional process. Preferably, the biologically active material subject to this invention has improved rheology compared to a biologically active material with the same, similar or larger particle size manufactured using a conventional process. Preferably, the biologically active material subject to this invention has reduced segregation compared to a biologically active material with the same, similar or larger particle size manufactured using a conventional process. Preferably, the biologically active material subject to this invention has increased bulk density or tapped bulk density compared to a biologically active material with the same, similar or larger particle size manufactured using a conventional process. Preferably, the biologically active material subject to this invention has superior powder flow as defined by the Hausner ratio or Carr's index compared to a biologically active material with the same, similar or larger particle size manufactured using a conventional process. Preferably, the biologically active material subject to this invention has lower compressibility compared to a biologically active material with the same, similar or larger particle size manufactured using a conventional process. Preferably, the biologically active material subject to this invention has increased permiability compared to a biologically active material with the same, similar or larger particle size manufactured using a conventional process. Preferably, the biologically active material subject to this invention has a higher minimum ignition energy compared to a biologically active material with the same, similar or larger particle size manufactured using a conventional process. Preferably, the biologically active material subject to this invention has higher hopper flow rates compared to a biologically active material with the same, similar or larger particle size manufactured using a conventional process. Preferably, the biologically active material subject to this invention has smaller critical orifice diameter compared to a biologically active material with the same, similar or larger particle size manufactured using a conventional process. Preferably, the biologically active material subject to this invention has smaller angle of repose compared to a biologically active material with the same, similar or larger particle size manufactured using a conventional process. Preferably, the biologically active material subject to this invention has smaller dynamic angle of repose compared to a biologically active material with the same, similar or larger particle size manufactured using a conventional process.

In a second aspect, the invention comprises a method for producing a blend containing nanoparticle and/or microparticles of biologically active material with powder handling characteristics superior to a blend made by conventional methods, wherein the said method comprises the steps of dry milling a solid biologically active material and a millable grinding matrix in a mill comprising a plurality of milling bodies, for a time period sufficient to produce particles of the biologically active material dispersed in an at least partially milled grinding material. In one embodiment, the blend has a median particle size, determined on a particle volume basis, equal or greater than a size selected from the group consisting of: 20,000 nm, 15,000 nm, 10,000 nm, 8000 nm, 6000 nm, 5000 nm, 4000 nm, 3000 nm and 2000 nm. In another embodiment, the blend has a median particle size, determined on a particle volume basis equal or less than 50 micron. In another embodiment, the blend has a volume weighted mean (D4,3) equal or greater than a size selected from the group consisting of: 40,000 nm, 30,000 nm, 20,000 nm, 15,000 nm, 10,000 nm, 8000 nm, 6000 nm and 5000 nm. In another embodiment, the blend has a volume weighted mean (D4,3) equal or less than 70 micron. In another embodiment, the percentage of particles in the blend, on a particle volume basis, is selected from the group consisting of: greater than 2 micron (%>2 micron) is selected from the group 50%, 60%, 70%, 80%, 85%, 90% and 95%; greater than 10 micron (%>10 micron) is selected from the group 10%, 20%, 30%, 40%, 50%, 60%, 70%, 80%, 85%, 90% and 95%; equal to or less than 20 micron (%<20 micron) is selected from the group 10%, 20%, 30%, 40%, 50%, 60%, 70%, 80%, 90%, 95% and 100%.

In another preferred embodiment, the average particle size of the biologically active material, determined on a particle number basis, is equal to or less than a size selected from the group consisting of, 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size is equal to or greater than 25 nm.

In another preferred embodiment, the particles of the biologically active material have a median particle size, determined on a particle volume basis, equal or less than a size selected from the group consisting of 20,000 nm, 15,000 nm, 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size of the biologically active material is equal to or greater than 25 nm. Preferably, the percentage of particles, on a particle volume basis, is selected from the group consisting of: 50%, 60%, 70%, 80%, 90%, 95% and 100% less than 20,000 nm (%<20,000 nm). Preferably, the percentage of particles, on a particle volume basis, is selected from the group consisting of: 50%, 60%, 70%, 80%, 90%, 95% and 100% less than 10,000 nm (%<10,000 nm). Preferably, the percentage of particles, on a particle volume basis, is selected from the group consisting of: 50%, 60%, 70%, 80%, 90%, 95% and 100% less than 5000 nm (%<5000 nm). Preferably, the percentage of particles, on a particle volume basis, is selected from the group consisting of: 50%, 60%, 70%, 80%, 90%, 95% and 100% less than 2000 nm (%<2000 nm). Preferably, the percentage of particles, on a particle volume basis, is selected from the group consisting of: 50%, 60%, 70%, 80%, 90%, 95% and 100% less than 1000 nm (%<1000 nm). Preferably, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). Preferably, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). Preferably, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). Preferably, the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm, wherein x is greater than or equal to 90.

In another preferred embodiment, the crystallinity profile of the biologically active material is selected from the group consisting of: at least 50% of the biologically active material is crystalline, at least 60% of the biologically active material is crystalline, at least 70% of the biologically active material is crystalline, at least 75% of the biologically active material is crystalline, at least 85% of the biologically active material is crystalline, at least 90% of the biologically active material is crystalline, at least 95% of the biologically active material is crystalline and at least 98% of the biologically active material is crystalline. More preferably, the crystallinity profile of the biologically active material is substantially equal to the crystallinity profile of the biologically active material before the material was subjected to the method as described herein.

In another preferred embodiment, the amorphous content of the biologically active material is selected from the group consisting of: less than 50% of the biologically active material is amorphous, less than 40% of the biologically active material is amorphous, less than 30% of the biologically active material is amorphous, less than 25% of the biologically active material is amorphous, less than 15% of the biologically active material is amorphous, less than 10% of the biologically active material is amorphous, less than 5% of the biologically active material is amorphous and less than 2% of the biologically active material is amorphous. Preferably, the biologically active material has no significant increase in amorphous content after subjecting the material to the method as described herein.

In another preferred embodiment, the milling time period is a range selected from the group consisting of: between 10 minutes and 2 hours, between 10 minutes and 90 minutes, between 10 minutes and 1 hour, between 10 minutes and 45 minutes, between 10 minutes and 30 minutes, between 5 minutes and 30 minutes, between 5 minutes and 20 minutes, between 2 minutes and 10 minutes, between 2 minutes and 5 minutes, between 1 minutes and 20 minutes, between 1 minute and 10 minutes, and between 1 minute and 5 minutes.

In another preferred embodiment, the milling medium is selected from the group consisting of: ceramics, glasses, polymers, ferromagnetics and metals. Preferably, the milling medium is steel balls having a diameter selected from the group consisting of: between 1 and 20 mm, between 2 and 15 mm and between 3 and 10 mm. In another preferred embodiment, the milling medium is zirconium oxide balls having a diameter selected from the group consisting of: between 1 and 20 mm, between 2 and 15 mm and between 3 and 10 mm. Preferably, the dry milling apparatus is a mill selected from the group consisting of: attritor mills (horizontal or vertical), nutating mills, tower mills, pearl mills, planetary mills, vibratory mills, eccentric vibratory mills, gravity-dependent-type ball mills, rod mills, roller mills and crusher mills. Preferably, the milling medium within the milling apparatus is mechanically agitated by 1, 2 or 3 rotating shafts. Preferably, the method is configured to produce the biologically active material in a continuous fashion.

Preferably, the total combined amount of biologically active material and grinding matrix in the mill at any given time is equal to or greater than a mass selected from the group consisting of: 200 grams, 500 grams, 1 kg, 2 kg, 5 kg, 10 kg, 20 kg, 30 kg, 50 kg, 75 kg, 100 kg, 150 kg, 200 kg. Preferably, the total combined amount of biologically active material and grinding matrix is less than 2000 kg.

In another preferred embodiment, the biologically active material is selected from the group consisting of: fungicides, pesticides, herbicides, seed treatments, cosmeceuticals, cosmetics, complementary medicines, natural products, vitamins, nutrients, nutraceuticals, pharmaceutical actives, biologics, amino acids, proteins, peptides, nucleotides, nucleic acids, additives, foods and food ingredients and analogs, homologs and first order derivatives thereof. Preferably, the biologically active material is selected from the group consisting of: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines. Preferably, the biologically active material is selected from the group consisting of: indomethacin, diclofenac, naproxen, meloxicam, metaxalone, cyclosporin A, progesterone and estradiol or any salt or derivative thereof.

In another preferred embodiment, the grinding matrix is a single material or is a mixture of two or more materials in any proportion. Preferably, the single material or a mixture of two or more materials is selected from the group consisting of: mannitol, sorbitol, Isomalt, xylitol, maltitol, lactitol, erythritol, arabitol, ribitol, glucose, fructose, mannose, galactose, anhydrous lactose, lactose monohydrate, sucrose, maltose, trehalose, maltodextrins, dextrin, Inulin, dextrates, polydextrose, starch, wheat flour, corn flour, rice flour, rice starch, tapioca flour, tapioca starch, potato flour, potato starch, other flours and starches, milk powder, skim milk powders, other milk solids and derivatives, soy flour, soy meal or other soy products, cellulose, microcrystalline cellulose, microcrystalline cellulose based co blended materials, pregelatinized (or partially) starch, HPMC, CMC, HPC, citric acid, tartaric acid, malic acid, maleic acid fumaric acid, ascorbic acid, succinic acid, sodium citrate, sodium tartrate, sodium malate, sodium ascorbate, potassium citrate, potassium tartrate, potassium malate, potassium ascorbate, sodium carbonate, potassium carbonate, magnesium carbonate, sodium bicarbonate, potassium bicarbonate and calcium carbonate. dibasic calcium phosphate, tribasic calcium phosphate, sodium sulfate, sodium chloride, sodium metabisulphite, sodium thiosulfate, ammonium chloride, Glauber's salt, ammonium carbonate, sodium bisulfate, magnesium sulfate, potash alum, potassium chloride, sodium hydrogen sulfate, sodium hydroxide, crystalline hydroxides, hydrogen carbonates, ammonium chloride, methylamine hydrochloride, ammonium bromide, silica, thermal silica, alumina, titanium dioxide, talc, chalk, mica, kaolin, bentonite, hectorite, magnesium trisilicate, clay based materials or aluminium silicates, sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Sodium Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines. Preferably, the concentration of the single (or first) material is selected from the group consisting of: 5-99% w/w, 10-95% w/w, 15-85% w/w, of 20-80% w/w, 25-75% w/w, 30-60% w/w, 40-50% w/w. Preferably, the concentration of the second or subsequent material is selected from the group consisting of: 5-50% w/w, 5-40% w/w, 5-30% w/w, of 5-20% w/w, 10-40% w/w, 10-30% w/w, 10-20% w/w, 20-40% w/w, or 20-30% w/w or if the second or subsequent material is a surfactant or water soluble polymer the concentration is selected from 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

Preferably, the grinding matrix is selected from the group consisting of:

(a) lactose monohydrate or lactose monohydrate combined with at least one material selected from the group consisting of: xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(b) lactose anhydrous or lactose anhydrous combined with at least one material selected from the group consisting of: lactose monohydrate; xylitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(c) mannitol or mannitol combined with at least one material selected from the group consisting of: lactose monohydrate; xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid;

Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(d) Sucrose or sucrose combined with at least one material selected from the group consisting of: lactose monohydrate; lactose anhydrous; mannitol; microcrystalline cellulose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(e) Glucose or glucose combined with at least one material selected from the group consisting of: lactose monohydrate; lactose anhydrous; mannitol; microcrystalline cellulose; sucrose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(f) Sodium chloride or sodium chloride combined with at least one material selected from the group consisting of: lactose monohydrate; lactose anhydrous; mannitol; microcrystalline cellulose; sucrose; glucose; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(g) xylitol or xylitol combined with at least one material selected from the group consisting of: lactose monohydrate; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(h) Tartaric acid or tartaric acid combined with at least one material selected from the group consisting of: lactose monohydrate; lactose anhydrous; mannitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(i) microcrystalline cellulose or microcrystalline cellulose combined with at least one material selected from the group consisting of: lactose monohydrate; xylitol; lactose anhydrous; mannitol; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowal-kylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(j) Kaolin combined with at least one material selected from the group consisting of: lactose monohydrate; xylitol; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowal-kylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(k) Talc combined with at least one material selected from the group consisting of: lactose monohydrate; xylitol; lactose anhydrous; mannitol; microcrystalline cellulose; sucrose; glucose; sodium chloride; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

Preferably, the grinding matrix is selected from the group consisting of: a material considered to be Generally Regarded as Safe (GRAS) for pharmaceutical products; a material considered acceptable for use in an agricultural formulation; and a material considered acceptable for use in a veterinary formulation.

In another preferred embodiment, a milling aid or combination of milling aids is used. Preferably, the milling aid is selected from the group consisting of: colloidal silica, a surfactant, a polymer, a stearic acid and derivatives thereof. Preferably, the surfactant is selected from the group consisting of: polyoxyethylene alkyl ethers, polyoxyethylene stearates, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, Sorbitan fatty acid esters, Sucrose fatty acid esters, alkyl glucopyranosides, alkyl maltopyranosides, glycerol fatty acid esters, Alkyl Benzene Sulphonic Acids, Alkyl Ether Carboxylic Acids, Alkyl and aryl Phosphate esters, Alkyl and aryl Sulphate esters, Alkyl and aryl Sulphonic acids, Alkyl Phenol Phosphates esters, Alkyl Phenol Sulphates esters, Alkyl and Aryl Phosphates, Alkyl Polysaccharides, Alkylamine Ethoxylates, Alkyl-Naphthalene Sulphonates formaldehyde condensates, Sulfo-succinates, lignosulfonates, Ceto-Oleyl Alcohol Ethoxy-lates, Condensed Naphthalene Sulphonates, Dialkyl and Alkyl Naphthalene Sulphonates, Di-alkyl Sulphosuccinates, Ethoxylated nonylphenols, Ethylene Glycol Esters, Fatty Alcohol Alkoxylates, Hydrogenated tallowalkylamines, Mono-alkyl Sulphosuccinamates, Nonyl Phenol Ethoxy-lates, Sodium Oleyl N-methyl Taurate, Tallowalkylamines, linear and branched dodecylbenzene sulfonic acids Preferably, the surfactant is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyc-eryl oleate, benzalkonium chloride, CTAB, CTAC, Cetrim-ide, cetylpyridinium chloride, cetylpyridinium bromide, benzethonium chloride, PEG 40 stearate, PEG 100 stearate, poloxamer 188, poloxamer 407, poloxamer 338, polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydroge-nated castor oil, polyoxyl 60 hydrogenated castor oil, poly-oxyl 100 hydrogenated castor oil, polyoxyl 200 hydroge-nated castor oil, cetostearyl alcohol, macrogel 15 hydroxystearate, sorbitan monopalmitate, sorbitan monos-tearate, sorbitan trioleate, Sucrose Palmitate, Sucrose Stear-ate, Sucrose Distearate, Sucrose laurate, Glycocholic acid, sodium Glycholate, Cholic Acid, Sodium Cholate, Sodium Deoxycholate, Deoxycholic acid, Sodium taurocholate, tau-rocholic acid, Sodium taurodeoxycholate, taurodeoxycholic acid, soy lecithin, phosphatidylcholine, phosphatidyletha-nolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulpho-nate, erythritol distearate, Naphthalene Sulfonate Formalde-hyde Condensate, nonylphenol ethoxylate (poe-30), Tristyrylphenol Ethoxylate, Polyoxyethylene (15) tallowal-kylamines, sodium alkyl naphthalene sulfonate, sodium alkyl naphthalene sulfonate condensate, sodium alkylben-zene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphe-nol Ethoxylate Sulfate, Bis(2-hydroxyethyl)tallowalkylam-ines.

Preferably the polymer is selected from the list of: poly-vinylpyrrolidones (PVP), polyvinylalcohol, Acrylic acid based polymers and copolymers of acrylic acid Preferably, the milling aid has a concentration selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

In another preferred embodiment of the invention, a facilitating agent is used or combination of facilitating agents is used. Preferably, the facilitating agent is selected from the group consisting of: surfactants, polymers, binding agents, filling agents, lubricating agents, sweeteners, fla-vouring agents, preservatives, buffers, wetting agents, disintegrants, effervescent agents, agents that may form part of a medicament, including a solid dosage form or a dry powder inhalation formulation and other material required for specific drug delivery. Preferably, the facilitating agent is added during dry milling. Preferably, the facilitating agent is added to the dry milling at a time selected from the group consisting of: with 1-5% of the total milling time remaining, with 1-10% of the total milling time remaining, with 1-20% of the total milling time remaining, with 1-30% of the total milling time remaining, with 2-5% of the total milling time remaining, with 2-10% of the total milling time remaining, with 5-20% of the total milling time remaining and with 5-20% of the total milling time remaining. Preferably, the disintegrant is selected from the group consisting of: cross-linked PVP, cross linked carmellose and sodium starch glycolate. Preferably, the facilitating agent is added to the milled biologically active material and grinding matrix and further processed in a mechanofusion process. Mechanofu-sion milling causes mechanical energy to be applied to powders or mixtures of particles in the micrometre and nanometre range.

The reasons for including facilitating agents include, but are not limited to providing better dispersibility, control of agglomeration, the release or retention of the active particles from the delivery matrix. Examples of facilitating agents include, but are not limited to crosslinked PVP (crospovi-done), cross linked carmellose (croscarmellose), sodium starch glycolate, Povidone (PVP), Povidone K12, Povidone K17, Povidone K25, Povidone K29/32 and Povidone K30, stearic acid, magnesium stearate, calcium stearate, sodium stearyl fumarate, sodium stearyl lactylate, zinc stearate, sodium stearate or lithium stearate, other solid state fatty acids such as oleic acid, lauric acid, palmitic acid, erucic acid, behenic acid, or derivatives (such as esters and salts), Amino acids such as leucine, isoleucine, lysine, valine, methionine, phenylalanine, aspartame or acesulfame K. In a preferred aspect of manufacturing this formulation the facili-tating agent is added to the milled mixture of biologically active material and co-grinding matrix and further processed in another milling device such as Mechnofusion, Cyclomix-ing, or impact milling such as ball milling, jet milling, or milling using a high pressure homogeniser, or combinations thereof. In a highly preferred aspect the facilitating agent is added to the milling of the mixture of biologically active material and co-grinding matrix as some time before the end of the milling process.

In another preferred embodiment, indomethacin is milled with lactose monohydrate and alkyl sulfates. Preferably indomethacin is milled with lactose monohydrate and sodium lauryl sulfate. Preferably indomethacin is milled with lactose monohydrate and sodium octadecyl sulfate. In another preferred embodiment, Indomethacin is milled with lactose monohydrate, alkyl sulfates and another surfactant or polymers. Preferably indomethacin is milled with lactose monohydrate, sodium lauryl sulfate and polyether sulfates. Preferably indomethacin is milled with lactose monohy-drate, sodium lauryl sulfate and polyethylene glycol 40 stearate. Preferably indomethacin is milled with lactose monohydrate, sodium lauryl sulfate and polyethylene glycol 100 stearate. Preferably indomethacin is milled with lactose monohydrate, sodium lauryl sulfate and a poloxamer. Pref-erably indomethacin is milled with lactose monohydrate, sodium lauryl sulfate and poloxamer 407. Preferably indo-methacin is milled with lactose monohydrate, sodium lauryl sulfate and poloxamer 338. Preferably indomethacin is milled with lactose monohydrate, sodium lauryl sulfate and poloxamer 188. Preferably indomethacin is milled with lactose monohydrate, sodium lauryl sulfate and a solid polyethylene glycol. Preferably indomethacin is milled with lactose monohydrate, sodium lauryl sulfate and polyethylene glycol 6000. Preferably indomethacin is milled with lactose monohydrate, sodium lauryl sulfate and polyethylene glycol 3000. In another preferred embodiment, Indomethacin is milled with lactose monohydrate and polyether sulfates. Preferably indomethacin is milled with lactose monohydrate and polyethylene glycol 40 stearate. Preferably indomethacin is milled with lactose monohydrate and polyethylene glycol 100 stearate In another preferred embodiment indomethacin is milled with lactose monohydrate and polyvinyl-pyrrolidine. Preferably indomethacin is milled with lactose monohydrate and polyvinyl-pyrrolidone with an approximate molecular weight of 30,000-40,000. In another preferred embodiment, indomethacin is milled with lactose monohydrate and alkyl sulfonates. Preferably indomethacin is milled with lactose monohydrate and docusate sodium. In another preferred embodiment, indomethacin is milled with lactose monohydrate and a surfactant. Preferably indomethacin is milled with lactose monohydrate and lecithin. Preferably indomethacin is milled with lactose monohydrate and sodium n-lauroyl sarcosine. Preferably indomethacin is milled with lactose monohydrate and polyoxyethylene alkyl ether surfactants. Preferably indomethacin is milled with lactose monohydrate and PEG 6000. In another preferred formulation indomethacin is milled with lactose monohydrate and silica. Preferably indomethacin is milled with lactose monohydrate and Aerosil R972 fumed silica. In another preferred embodiment, indomethacin is milled with with lactose monohydrate, tartaric acid and sodium lauryl sulfate. In another preferred embodiment, indomethacin is milled with with lactose monohydrate, sodium bicarbonate and sodium lauryl sulfate. In another preferred embodiment, indomethacin is milled with lactose monohydrate, potassium bicarbonate and sodium lauryl sulfate. In another preferred embodiment, indomethacin is milled with mannitol and alkyl sulfates. Preferably indomethacin is milled with mannitol and sodium lauryl sulfate. Preferably indomethacin is milled with mannitol and sodium octadecyl sulfate. In another preferred embodiment, Indomethacin is milled with mannitol, alkyl sulfates and another surfactant or polymers. Preferably indomethacin is milled with mannitol, sodium lauryl sulfate and polyether sulfates. Preferably indomethacin is milled with mannitol, sodium lauryl sulfate and polyethylene glycol 40 stearate. Preferably indomethacin is milled with mannitol, sodium lauryl sulfate and polyethylene glycol 100 stearate. Preferably indomethacin is milled with mannitol, sodium lauryl sulfate and a poloxamer. Preferably indomethacin is milled with mannitol, sodium lauryl sulfate and poloxamer 407. Preferably indomethacin is milled with mannitol, sodium lauryl sulfate and poloxamer 338. Preferably indomethacin is milled with mannitol, sodium lauryl sulfate and poloxamer 188. Preferably indomethacin is milled with mannitol, sodium lauryl sulfate and a solid polyethylene glycol. Preferably indomethacin is milled with mannitol, sodium lauryl sulfate and polyethylene glycol 6000. Preferably indomethacin is milled with mannitol, sodium lauryl sulfate and polyethylene glycol 3000. In another preferred embodiment, Indomethacin is milled with mannitol and polyether sulfates. Preferably indomethacin is milled with mannitol and polyethylene glycol 40 stearate. Preferably indomethacin is milled with mannitol and polyethylene glycol 100 stearate In another preferred embodiment indomethacin is milled with mannitol and polyvinyl-pyrrolidine. Preferably indomethacin is milled with mannitol and polyvinyl-pyrrolidone with an approximate molecular weight of 30,000-40,000. In another preferred embodiment, indomethacin is milled with mannitol and alkyl sulfonates. Preferably indomethacin is milled with mannitol and docusate sodium. In another preferred embodiment, indomethacin is milled with mannitol and a surfactant. Preferably indomethacin is milled with mannitol and lecithin. Preferably indomethacin is milled with mannitol and sodium n-lauroyl sarcosine. Preferably indomethacin is milled with mannitol and polyoxyethylene alkyl ether surfactants. Preferably indomethacin is milled with mannitol and PEG 6000. In another preferred formulation indomethacin is milled with mannitol and silica. Preferably indomethacin is milled with mannitol and Aerosil R972 fumed silica. In another preferred embodiment, indomethacin is milled with with mannitol, tartaric acid and sodium lauryl sulfate. In another preferred embodiment, indomethacin is milled with with mannitol, sodium bicarbonate and sodium lauryl sulfate. In another preferred embodiment, indomethacin is milled with mannitol, potassium bicarbonate and sodium lauryl sulfate.

In another preferred embodiment, naproxen is milled with lactose monohydrate and alkyl sulfates. Preferably naproxen is milled with lactose monohydrate and sodium lauryl sulfate. Preferably naproxen is milled with lactose monohydrate and sodium octadecyl sulfate. In another preferred embodiment, Naproxen is milled with lactose monohydrate, alkyl sulfates and another surfactant or polymers. Preferably naproxen is milled with lactose monohydrate, sodium lauryl sulfate and polyether sulfates. Preferably naproxen is milled with lactose monohydrate, sodium lauryl sulfate and polyethylene glycol 40 stearate. Preferably naproxen is milled with lactose monohydrate, sodium lauryl sulfate and polyethylene glycol 100 stearate. Preferably naproxen is milled with lactose monohydrate, sodium lauryl sulfate and a poloxamer. Preferably naproxen is milled with lactose monohydrate, sodium lauryl sulfate and poloxamer 407. Preferably naproxen is milled with lactose monohydrate, sodium lauryl sulfate and poloxamer 338. Preferably naproxen is milled with lactose monohydrate, sodium lauryl sulfate and poloxamer 188. Preferably naproxen is milled with lactose monohydrate, sodium lauryl sulfate and a solid polyethylene glycol. Preferably naproxen is milled with lactose monohydrate, sodium lauryl sulfate and polyethylene glycol 6000. Preferably naproxen is milled with lactose monohydrate, sodium lauryl sulfate and polyethylene glycol 3000. In another preferred embodiment, Naproxen is milled with lactose monohydrate and polyether sulfates. Preferably naproxen is milled with lactose monohydrate and polyethylene glycol 40 stearate. Preferably naproxen is milled with lactose monohydrate and polyethylene glycol 100 stearate In another preferred embodiment naproxen is milled with lactose monohydrate and polyvinyl-pyrrolidine. Preferably naproxen is milled with lactose monohydrate and polyvinyl-pyrrolidone with an approximate molecular weight of 30,000-40,000. In another preferred embodiment, naproxen is milled with lactose monohydrate and alkyl sulfonates. Preferably naproxen is milled with lactose monohydrate and docusate sodium. In another preferred embodiment, naproxen is milled with lactose monohydrate and a surfactant. Preferably naproxen is milled with lactose monohydrate and lecithin. Preferably naproxen is milled with lactose monohydrate and sodium n-lauroyl sarcosine. Preferably naproxen is milled with lactose monohydrate and polyoxyethylene alkyl ether surfactants. Preferably naproxen is milled with lactose monohydrate and PEG 6000. In another preferred formulation naproxen is milled with lactose monohydrate and silica. Preferably naproxen is milled with lactose monohydrate and Aerosil R972 fumed silica. In another preferred embodiment, naproxen is milled with with lactose monohydrate, tartaric acid and sodium lauryl sulfate. In another preferred embodiment, naproxen is milled with with lactose monohydrate, sodium bicarbonate and sodium lauryl sulfate. In another preferred embodiment, naproxen is milled with lactose monohydrate, potassium bicarbonate and sodium lauryl sulfate. In another preferred embodiment, naproxen is milled with mannitol and alkyl sulfates. Preferably naproxen is milled with mannitol and sodium lauryl sulfate. Preferably naproxen is milled with mannitol and sodium octadecyl sulfate. In another preferred embodiment, Naproxen is milled with mannitol, alkyl sulfates and another surfactant or polymers. Preferably naproxen is milled with mannitol, sodium lauryl sulfate and polyether sulfates. Preferably naproxen is milled with mannitol, sodium lauryl sulfate and polyethylene glycol 40 stearate. Preferably naproxen is milled with mannitol, sodium lauryl sulfate and polyethylene glycol 100 stearate. Preferably naproxen is milled with mannitol, sodium lauryl sulfate and a poloxamer. Preferably naproxen is milled with mannitol, sodium lauryl sulfate and poloxamer 407. Preferably naproxen is milled with mannitol, sodium lauryl sulfate and poloxamer 338. Preferably naproxen is milled with mannitol, sodium lauryl sulfate and poloxamer 188. Preferably naproxen is milled with mannitol, sodium lauryl sulfate and a solid polyethylene glycol. Preferably naproxen is milled with mannitol, sodium lauryl sulfate and polyethylene glycol 6000. Preferably naproxen is milled with mannitol, sodium lauryl sulfate and polyethylene glycol 3000. In another preferred embodiment, Naproxen is milled with mannitol and polyether sulfates. Preferably naproxen is milled with mannitol and polyethylene glycol 40 stearate. Preferably naproxen is milled with mannitol and polyethylene glycol 100 stearate In another preferred embodiment naproxen is milled with mannitol and polyvinyl-pyrrolidine. Preferably naproxen is milled with mannitol and polyvinyl-pyrrolidone with an approximate molecular weight of 30,000-40,000. In another preferred embodiment, naproxen is milled with mannitol and alkyl sulfonates. Preferably naproxen is milled with mannitol and docusate sodium. In another preferred embodiment, naproxen is milled with mannitol and a surfactant. Preferably naproxen is milled with mannitol and lecithin. Preferably naproxen is milled with mannitol and sodium n-lauroyl sarcosine. Preferably naproxen is milled with mannitol and polyoxyethylene alkyl ether surfactants. Preferably naproxen is milled with mannitol and PEG 6000. In another preferred formulation naproxen is milled with mannitol and silica. Preferably naproxen is milled with mannitol and Aerosil R972 fumed silica. In another preferred embodiment, naproxen is milled with with mannitol, tartaric acid and sodium lauryl sulfate. In another preferred embodiment, naproxen is milled with with mannitol, sodium bicarbonate and sodium lauryl sulfate. In another preferred embodiment, naproxen is milled with mannitol, potassium bicarbonate and sodium lauryl sulfate.

In another preferred embodiment, diclofenac is milled with lactose monohydrate and alkyl sulfates. Preferably diclofenac is milled with lactose monohydrate and sodium lauryl sulfate. Preferably diclofenac is milled with lactose monohydrate and sodium octadecyl sulfate. In another preferred embodiment, Diclofenac is milled with lactose monohydrate, alkyl sulfates and another surfactant or polymers. Preferably diclofenac is milled with lactose monohydrate, sodium lauryl sulfate and polyether sulfates. Preferably diclofenac is milled with lactose monohydrate, sodium lauryl sulfate and polyethylene glycol 40 stearate. Preferably diclofenac is milled with lactose monohydrate, sodium lauryl sulfate and polyethylene glycol 100 stearate. Preferably diclofenac is milled with lactose monohydrate, sodium lauryl sulfate and a poloxamer. Preferably diclofenac is milled with lactose monohydrate, sodium lauryl sulfate and poloxamer 407. Preferably diclofenac is milled with lactose monohydrate, sodium lauryl sulfate and poloxamer 338. Preferably diclofenac is milled with lactose monohydrate, sodium lauryl sulfate and poloxamer 188. Preferably diclofenac is milled with lactose monohydrate, sodium lauryl sulfate and a solid polyethylene glycol. Preferably diclofenac is milled with lactose monohydrate, sodium lauryl sulfate and polyethylene glycol 6000. Preferably diclofenac is milled with lactose monohydrate, sodium lauryl sulfate and polyethylene glycol 3000. In another preferred embodiment, Diclofenac is milled with lactose monohydrate and polyether sulfates. Preferably diclofenac is milled with lactose monohydrate and polyethylene glycol 40 stearate. Preferably diclofenac is milled with lactose monohydrate and polyethylene glycol 100 stearate In another preferred embodiment diclofenac is milled with lactose monohydrate and polyvinyl-pyrrolidine. Preferably diclofenac is milled with lactose monohydrate and polyvinyl-pyrrolidone with an approximate molecular weight of 30,000-40,000. In another preferred embodiment, diclofenac is milled with lactose monohydrate and alkyl sulfonates. Preferably diclofenac is milled with lactose monohydrate and docusate sodium. In another preferred embodiment, diclofenac is milled with lactose monohydrate and a surfactant. Preferably diclofenac is milled with lactose monohydrate and lecithin. Preferably diclofenac is milled with lactose monohydrate and sodium n-lauroyl sarcosine. Preferably diclofenac is milled with lactose monohydrate and polyoxyethylene alkyl ether surfactants. Preferably diclofenac is milled with lactose monohydrate and PEG 6000. In another preferred formulation diclofenac is milled with lactose monohydrate and silica. Preferably diclofenac is milled with lactose monohydrate and Aerosil R972 fumed silica. In another preferred embodiment, diclofenac is milled with with lactose monohydrate, tartaric acid and sodium lauryl sulfate. In another preferred embodiment, diclofenac is milled with with lactose monohydrate, sodium bicarbonate and sodium lauryl sulfate. In another preferred embodiment, diclofenac is milled with lactose monohydrate, potassium bicarbonate and sodium lauryl sulfate. In another preferred embodiment, diclofenac is milled with mannitol and alkyl sulfates. Preferably diclofenac is milled with mannitol and sodium lauryl sulfate. Preferably diclofenac is milled with mannitol and sodium octadecyl sulfate. In another preferred embodiment, Diclofenac is milled with mannitol, alkyl sulfates and another surfactant or polymers. Preferably diclofenac is milled with mannitol, sodium lauryl sulfate and polyether sulfates. Preferably diclofenac is milled with mannitol, sodium lauryl sulfate and polyethylene glycol 40 stearate. Preferably diclofenac is milled with mannitol, sodium lauryl sulfate and polyethylene glycol 100 stearate. Preferably diclofenac is milled with mannitol, sodium lauryl sulfate and a poloxamer. Preferably diclofenac is milled with mannitol, sodium lauryl sulfate and poloxamer 407. Preferably diclofenac is milled with mannitol, sodium lauryl sulfate and poloxamer 338. Preferably diclofenac is milled with mannitol, sodium lauryl sulfate and poloxamer 188. Preferably diclofenac is milled with mannitol, sodium lauryl sulfate and a solid polyethylene glycol. Preferably diclofenac is milled with mannitol, sodium lauryl sulfate and polyethylene glycol 6000. Preferably diclofenac is milled with mannitol, sodium lauryl sulfate and polyethylene glycol 3000. In another preferred embodiment, Diclofenac is milled with mannitol and polyether sulfates. Preferably diclofenac is milled with mannitol and polyethylene glycol 40 stearate Preferably diclofenac is milled with mannitol and polyethylene glycol 100 stearate In another preferred embodiment diclofenac is milled with mannitol and polyvinyl-pyrrolidine. Preferably diclofenac is milled with mannitol and polyvinyl-pyrrolidone with an approximate molecular weight of 30,000-40,000. In another preferred embodiment, diclofenac is milled with mannitol and alkyl sulfonates. Preferably diclofenac is milled with mannitol and docusate sodium. In another preferred embodiment, diclofenac is milled with mannitol and a surfactant. Preferably diclofenac is milled with mannitol and lecithin. Preferably diclofenac is milled with mannitol and sodium n-lauroyl sarcosine. Preferably diclofenac is milled with mannitol and polyoxyethylene alkyl ether surfactants. Preferably diclofenac is milled with mannitol and PEG 6000. In another preferred formulation diclofenac is milled with mannitol and silica. Preferably diclofenac is milled with mannitol and Aerosil R972 fumed silica. In another preferred embodiment, diclofenac is milled with with mannitol, tartaric acid and sodium lauryl sulfate. In another preferred embodiment, diclofenac is milled with with mannitol, sodium bicarbonate and sodium lauryl sulfate. In another preferred embodiment, diclofenac is milled with mannitol, potassium bicarbonate and sodium lauryl sulfate.

In another preferred embodiment, meloxicam is milled with lactose monohydrate and alkyl sulfates. Preferably meloxicam is milled with lactose monohydrate and sodium lauryl sulfate. Preferably meloxicam is milled with lactose monohydrate and sodium octadecyl sulfate. In another preferred embodiment, Meloxicam is milled with lactose monohydrate, alkyl sulfates and another surfactant or polymers. Preferably meloxicam is milled with lactose monohydrate, sodium lauryl sulfate and polyether sulfates. Preferably meloxicam is milled with lactose monohydrate, sodium lauryl sulfate and polyethylene glycol 40 stearate. Preferably meloxicam is milled with lactose monohydrate, sodium lauryl sulfate and polyethylene glycol 100 stearate. Preferably meloxicam is milled with lactose monohydrate, sodium lauryl sulfate and a poloxamer. Preferably meloxicam is milled with lactose monohydrate, sodium lauryl sulfate and poloxamer 407. Preferably meloxicam is milled with lactose monohydrate, sodium lauryl sulfate and poloxamer 338. Preferably meloxicam is milled with lactose monohydrate, sodium lauryl sulfate and poloxamer 188. Preferably meloxicam is milled with lactose monohydrate, sodium lauryl sulfate and a solidpolyethylene glycol. Preferably meloxicam is milled with lactose monohydrate, sodium lauryl sulfate and polyethylene glycol 6000. Preferably meloxicam is milled with lactose monohydrate, sodium lauryl sulfate and polyethylene glycol 3000. In another preferred embodiment, Meloxicam is milled with lactose monohydrate and polyether sulfates. Preferably meloxicam is milled with lactose monohydrate and polyethylene glycol 40 stearate. Preferably meloxicam is milled with lactose monohydrate and polyethylene glycol 100 stearate In another preferred embodiment meloxicam is milled with lactose monohydrate and polyvinyl-pyrrolidine. Preferably meloxicam is milled with lactose monohydrate and polyvinyl-pyrrolidone with an approximate molecular weight of 30,000-40,000. In another preferred embodiment, meloxicam is milled with lactose monohydrate and alkyl sulfonates. Preferably meloxicam is milled with lactose monohydrate and docusate sodium. In another preferred embodiment, meloxicam is milled with lactose monohydrate and a surfactant. Preferably meloxicam is milled with lactose monohydrate and lecithin. Preferably meloxicam is milled with lactose monohydrate and sodium n-lauroyl sarcosine. Preferably meloxicam is milled with lactose monohydrate and polyoxyethylene alkyl ether surfactants. Preferably meloxicam is milled with lactose monohydrate and PEG 6000. In another preferred formulation meloxicam is milled with lactose monohydrate and silica. Preferably meloxicam is milled with lactose monohydrate and Aerosil R972 fumed silica. In another preferred embodiment, meloxicam is milled with with lactose monohydrate, tartaric acid and sodium lauryl sulfate. In another preferred embodiment, meloxicam is milled with with lactose monohydrate, sodium bicarbonate and sodium lauryl sulfate. In another preferred embodiment, meloxicam is milled with lactose monohydrate, potassium bicarbonate and sodium lauryl sulfate. In another preferred embodiment, meloxicam is milled with mannitol and alkyl sulfates. Preferably meloxicam is milled with mannitol and sodium lauryl sulfate. Preferably meloxicam is milled with mannitol and sodium octadecyl sulfate. In another preferred embodiment, Meloxicam is milled with mannitol, alkyl sulfates and another surfactant or polymers. Preferably meloxicam is milled with mannitol, sodium lauryl sulfate and polyether sulfates. Preferably meloxicam is milled with mannitol, sodium lauryl sulfate and polyethylene glycol 40 stearate. Preferably meloxicam is milled with mannitol, sodium lauryl sulfate and polyethylene glycol 100 stearate. Preferably meloxicam is milled with mannitol, sodium lauryl sulfate and a poloxamer. Preferably meloxicam is milled with mannitol, sodium lauryl sulfate and poloxamer 407. Preferably meloxicam is milled with mannitol, sodium lauryl sulfate and poloxamer 338. Preferably meloxicam is milled with mannitol, sodium lauryl sulfate and poloxamer 188. Preferably meloxicam is milled with mannitol, sodium lauryl sulfate and a solid polyethylene glycol. Preferably meloxicam is milled with mannitol, sodium lauryl sulfate and polyethylene glycol 6000. Preferably meloxicam is milled with mannitol, sodium lauryl sulfate and polyethylene glycol 3000. In another preferred embodiment, Meloxicam is milled with mannitol and polyether sulfates. Preferably meloxicam is milled with mannitol and polyethylene glycol 40 stearate. Preferably meloxicam is milled with mannitol and polyethylene glycol 100 stearate In another preferred embodiment meloxicam is milled with mannitol and polyvinyl-pyrrolidine. Preferably meloxicam is milled with mannitol and polyvinyl-pyrrolidone with an approximate molecular weight of 30,000-40,000. In another preferred embodiment, meloxicam is milled with mannitol and alkyl sulfonates. Preferably meloxicam is milled with mannitol and docusate sodium. In another preferred embodiment, meloxicam is milled with mannitol and a surfactant. Preferably meloxicam is milled with mannitol and lecithin. Preferably meloxicam is milled with mannitol and sodium n-lauroyl sarcosine. Preferably meloxicam is milled with mannitol and polyoxyethylene alkyl ether surfactants. Preferably meloxicam is milled with mannitol and PEG 6000. In another preferred formulation meloxicam is milled with mannitol and silica. Preferably meloxicam is milled with mannitol and Aerosil R972 fumed silica. In another preferred embodiment, meloxicam is milled with with mannitol, tartaric acid and sodium lauryl sulfate. In another preferred embodiment, meloxicam is milled with with mannitol, sodium bicarbonate and sodium lauryl sulfate. In another preferred embodiment, meloxicam is milled with mannitol, potassium bicarbonate and sodium lauryl sulfate.

In another preferred embodiment, metaxalone is milled with lactose monohydrate and alkyl sulfates. Preferably metaxalone is milled with lactose monohydrate and sodium lauryl sulfate. Preferably metaxalone is milled with lactose monohydrate and sodium octadecyl sulfate. In another preferred embodiment, Metaxalone is milled with lactose monohydrate, alkyl sulfates and another surfactant or polymers. Preferably metaxalone is milled with lactose monohydrate, sodium lauryl sulfate and polyether sulfates. Preferably metaxalone is milled with lactose monohydrate, sodium lauryl sulfate and polyethylene glycol 40 stearate. Preferably metaxalone is milled with lactose monohydrate, sodium lauryl sulfate and polyethylene glycol 100 stearate. Preferably metaxalone is milled with lactose monohydrate, sodium lauryl sulfate and a poloxamer. Preferably metaxalone is milled with lactose monohydrate, sodium lauryl sulfate and poloxamer 407. Preferably metaxalone is milled with lactose monohydrate, sodium lauryl sulfate and poloxamer 338. Preferably metaxalone is milled with lactose monohydrate, sodium lauryl sulfate and poloxamer 188. Preferably metaxalone is milled with lactose monohydrate, sodium lauryl sulfate and a solid polyethylene glycol. Preferably metaxalone is milled with lactose monohydrate, sodium lauryl sulfate and polyethylene glycol 6000. Preferably metaxalone is milled with lactose monohydrate, sodium lauryl sulfate and polyethylene glycol 3000. In another preferred embodiment, Metaxalone is milled with lactose monohydrate and polyether sulfates. Preferably metaxalone is milled with lactose monohydrate and polyethylene glycol 40 stearate. Preferably metaxalone is milled with lactose monohydrate and polyethylene glycol 100 stearate. In another preferred embodiment metaxalone is milled with lactose monohydrate and polyvinyl-pyrrolidine. Preferably metaxalone is milled with lactose monohydrate and polyvinyl-pyrrolidone with an approximate molecular weight of 30,000-40,000. In another preferred embodiment, metaxalone is milled with lactose monohydrate and alkyl sulfonates. Preferably metaxalone is milled with lactose monohydrate and docusate sodium. In another preferred embodiment, metaxalone is milled with lactose monohydrate and a surfactant. Preferably metaxalone is milled with lactose monohydrate and lecithin. Preferably metaxalone is milled with lactose monohydrate and sodium n-lauroyl sarcosine. Preferably metaxalone is milled with lactose monohydrate and polyoxyethylene alkyl ether surfactants. Preferably metaxalone is milled with lactose monohydrate and PEG 6000. In another preferred formulation metaxalone is milled with lactose monohydrate and silica. Preferably metaxalone is milled with lactose monohydrate and Aerosil R972 fumed silica. In another preferred embodiment, metaxalone is milled with with lactose monohydrate, tartaric acid and sodium lauryl sulfate. In another preferred embodiment, metaxalone is milled with with lactose monohydrate, sodium bicarbonate and sodium lauryl sulfate. In another preferred embodiment, metaxalone is milled with with lactose monohydrate, sodium bicarbonate, poloxamer 407 and sodium lauryl sulfate. In another preferred embodiment, metaxalone is milled with lactose monohydrate, potassium bicarbonate and sodium lauryl sulfate. In another preferred embodiment, metaxalone is milled with with lactose monohydrate, potassium bicarbonate, poloxamer 407 and sodium lauryl sulfate.

In another preferred embodiment, metaxalone is milled with mannitol and alkyl sulfates. Preferably metaxalone is milled with mannitol and sodium lauryl sulfate. Preferably metaxalone is milled with mannitol and sodium octadecyl sulfate. In another preferred embodiment, Metaxalone is milled with mannitol, alkyl sulfates and another surfactant or polymers. Preferably metaxalone is milled with mannitol, sodium lauryl sulfate and polyether sulfates. Preferably metaxalone is milled with mannitol, sodium lauryl sulfate and polyethylene glycol 40 stearate. Preferably metaxalone is milled with mannitol, sodium lauryl sulfate and polyethylene glycol 100 stearate. Preferably metaxalone is milled with mannitol, sodium lauryl sulfate and a poloxamer. Preferably metaxalone is milled with mannitol, sodium lauryl sulfate and poloxamer 407. Preferably metaxalone is milled with mannitol, sodium lauryl sulfate and poloxamer 338. Preferably metaxalone is milled with mannitol, sodium lauryl sulfate and poloxamer 188. Preferably metaxalone is milled with mannitol, sodium lauryl sulfate and a solid polyethylene glycol. Preferably metaxalone is milled with mannitol, sodium lauryl sulfate and polyethylene glycol 6000. Preferably metaxalone is milled with mannitol, sodium lauryl sulfate and polyethylene glycol 3000. In another preferred embodiment, Metaxalone is milled with mannitol and polyether sulfates. Preferably metaxalone is milled with mannitol and polyethylene glycol 40 stearate Preferably metaxalone is milled with mannitol and polyethylene glycol 100 stearate In another preferred embodiment metaxalone is milled with mannitol and polyvinyl-pyrrolidine. Preferably metaxalone is milled with mannitol and polyvinyl-pyrrolidone with an approximate molecular weight of 30,000-40,000. In another preferred embodiment, metaxalone is milled with mannitol and alkyl sulfonates. Preferably metaxalone is milled with mannitol and docusate sodium. In another preferred embodiment, metaxalone is milled with mannitol and a surfactant. Preferably metaxalone is milled with mannitol and lecithin. Preferably metaxalone is milled with mannitol and sodium n-lauroyl sarcosine. Preferably metaxalone is milled with mannitol and polyoxyethylene alkyl ether surfactants. Preferably metaxalone is milled with mannitol and PEG 6000. In another preferred formulation metaxalone is milled with mannitol and silica. Preferably metaxalone is milled with mannitol and Aerosil R972 fumed silica. In another preferred embodiment, metaxalone is milled with with mannitol, tartaric acid and sodium lauryl sulfate. In another preferred embodiment, metaxalone is milled with with mannitol, sodium bicarbonate and sodium lauryl sulfate. In another preferred embodiment, metaxalone is milled with mannitol, potassium bicarbonate and sodium lauryl sulfate. In another preferred embodiment, metaxalone is milled with mannitol, sodium bicarbonate and sodium lauryl sulphate and Polxamer 407. In another preferred embodiment, metaxalone is milled with mannitol, potassium bicarbonate and sodium lauryl sulphate and Polxamer 407.

In another preferred embodiment, the particles have a volume weighted mean (D4,3), determined on a particle volume basis, equal or greater than a size selected from the group consisting of: 5000 nm, 10,000 nm, 15,000 nm, 20,000 nm, 25,000 nm, 35,000 nm, 40,000 nm and 50,000 nm.

In another preferred embodiment, the powder handling characteristic is a characteristic selected from the group consisting of: flow property, static charge, aggregation property, content uniformity, content uniformity after segregation, adherence property, cohesivity, dust level, powder rheology, segregation property, bulk density, tapped bulk density, powder flow, angle of repose, compressibility, permeability and minimum ignition property. In another preferred embodiment, the content uniformity and/or content uniformity after segregation of the biologically active material throughout the blend varies from the average content by a percentage less than or equal to a percentage selected from the group consisting of: 0.1%, 0.2%, 0.3%, 0.4%, 0.5% 0.75%, 1.0%, 1.5%, 2.0%, 3.0%, 4.0% and 5.0%. In another preferred embodiment the static property is selected from the group consisting of: less than 10 nC/g, less than 5 nC/g, less than 3 nC/g, less than 2 nC/g, less than 1.5 nC/g, less than 1.25 nC/g, less than 1 nC/g less than 0.75 nC/g, less than 0.5 nC/g, less than 0.25 nC/g and less than 0.1 nC/g. In another preferred embodiment, the biologically active material and/or blend containing biologically active material has a lower propensity for adherence to other materials such as but not limited to stainless steel, glass, plastic, polyethylene and polypropylene compared to the propensity for adherence of a biologically active material and/or blend with the same, similar or larger biologically active material particle size manufactured using a conventional process.

In a third aspect the invention comprises a biologically active material produced by the method described herein and composition comprising the biologically active material as described herein. Preferably, the average particle size of the biologically active material, determined on a particle number basis, is equal to or less than a size selected from the group 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size of the biologically active material is equal to or greater than 25 nm. Preferably, the particles of the biologically active material have a median particle size, determined on a particle volume basis, equal or less than a size selected from the group consisting of: 20,000 nm, 15,000 nm, 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size of the biologically active material is equal to or greater than 25 nm. Preferably, the percentage of particles, on a particle volume basis, is selected from the group consisting of: 50%, 60%, 70%, 80%, 90%, 95% and 100% less than 20,000 nm (%<20,000 nm). Preferably, the percentage of particles, on a particle volume basis, is selected from the group consisting of: 50%, 60%, 70%, 80%, 90%, 95% and 100% less than 10,000 nm (%<10,000 nm). Preferably, the percentage of particles, on a particle volume basis, is selected from the group consisting of: 50%, 60%, 70%, 80%, 90%, 95% and 100% less than 5000 nm (%<5000 nm). Preferably, the percentage of particles, on a particle volume basis, is selected from the group consisting of: 50%, 60%, 70%, 80%, 90%, 95% and 100% less than 2000 nm (%<2000 nm). Preferably, the percentage of particles, on a particle volume basis, is selected from the group consisting of: 50%, 60%, 70%, 80%, 90%, 95% and 100% less than 1000 nm (%<1000 nm). Preferably, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). Preferably, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). Preferably, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). Preferably, the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to 90 Preferably, the crystallinity profile of the biologically active material is selected from the group consisting of: at least 50% of the biologically active material is crystalline, at least 60% of the biologically active material is crystalline, at least 70% of the biologically active material is crystalline, at least 75% of the biologically active material is crystalline, at least 85% of the biologically active material is crystalline, at least 90% of the biologically active material is crystalline, at least 95% of the biologically active material is crystalline and at least 98% of the biologically active material is crystalline. Preferably, the crystallinity profile of the biologically active material is substantially equal to the crystallinity profile of the biologically active material before the material was subject to the method described herein. Preferably, the amorphous content of the biologically active material is selected from the group consisting of: less than 50% of the biologically active material is amorphous, less than 40% of the biologically active material is amorphous, less than 30% of the biologically active material is amorphous, less than 25% of the biologically active material is amorphous, less than 15% of the biologically active material is amorphous, less than 10% of the biologically active material is amorphous, less than 5% of the biologically active material is amorphous and less than 2% of the biologically active material is amorphous. Preferably, the biologically active material has had no significant increase in amorphous content following subjecting the material to the method as described herein. Preferably, the biologically active material comprised in the composition is selected from the group consisting of: fungicides, pesticides, herbicides, seed treatments, cosmeceuticals, cosmetics, complementary medicines, natural products, vitamins, nutrients, nutraceuticals, pharmaceutical actives, biologics, amino acids, proteins, peptides, nucleotides, nucleic acids, additives, foods and food ingredients and analogs, homologs and first order derivatives thereof. Preferably, where the biologically active material is a naturally occurring material or a derivate of a naturally occurring material, such as but not limited to, seeds, cocoa and cocoa solids, coffee, herbs, spices, other plant materials, minerals, animal products, shells and other skeletal material, the particles of the biologically active material have a median particle size, determined on a particle volume basis, equal or less than a size selected from the group 20,000, 15,000 nm, 10,000 nm, 8000 nm, 6000 nm, 5000 nm, 4000 nm and 3000 nm. Preferably, the biologically active material is selected from the group consisting of: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anti-coagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthenes. Preferably, the biologically active material is selected from the group consisting of: indomethacin, diclofenac, naproxen, meloxicam, metaxalone, cyclosporin A, progesterone celecoxib, cilostazol, ciprofloxacin, 2,4-dichlorophenoxyacetic acid, anthraquinone, creatine monohydrate, glyphosate, halusulfuron, mancozeb, metsulfuron, salbutamol, sulphur, tribenuran and estradiol or any salt or derivative thereof.

Preferably, the biologically active material is selected from the group consisting of: anti-obesity drugs, central nervous system stimulants, carotenoids, corticosteroids, elastase inhibitors, anti-fungals, oncology therapies, antiemetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics.

Preferably cosmeceuticals, cosmetics, complementary medicines, natural products, vitamins, nutrients and nutraceuticals are selected from the group consisting of: Glycolic acids, Lactic acids, Carrageenan, Almonds, Mahogany wood, *Andrographis Paniculata*, Aniseed, *Anthemis nobilis* (chamomile), Apricot kernel, leaves of bearberry, leaves of cranberry, leaves of blueberry, leaves of pear trees, betacarotene, black elderberry, black raspberry, black walnut shell, blackberry, bladderwrack, *Bletilla striata*, borage seed, boysenberry, brazil nut, burdock root, butcher's broom extract, calamine, calcium gluconate, calendula, carnosic acid, *Cantella asiatica*, charcoal, chaste tree fruit, Chicory root extract, chitosan, choline, *Cichorium intybus, Clematis vitalba, Coffea Arabica*, coumarin, *Crithmum maritimum*, curcumin, coffee, cocoa, cocoa powder, cocoa nibs, cocoa mass, cocoa liquor, cocoa products, dogwood, *Echinacea, Echium lycopsis*, anise, atragalus, bilberry, bitter orange, black cohosh, cat's claw, chamomile, chasteberry, cranberry, dandelion, *Echinacea*, ephedra, European elder *Epilobium angustifolium*, horse chestnut, cloves, evening primrose, fennel seed, fenugreek, feverfew, flaxseed, *Fumaria officinalis*, garlic, geranium, ginger, ginkgo, ginseng, goldenseal, grape seed, green tea, guava, hawthorn, hayflower, hazelnut, helichrysum, hoodia, horseradish, mulbe *italicum*, hibiscus, *Hierochloe odorata*, hops, horse chestnut, *Ilex paraguariensis*, indian gooseberry, irish moss, juniper berry, kudzu root, lady's thistle, lavender, lemongrass, lentius *edodes*, licorice, longifolene, loquat, lotus seed, *Luffa cylindrica*, lupine, maroinberry, marjoram, meadowsweet, milk vetch root, *Mimosa tenuiflora*, mistletoe, mulberry, noni, kelp, oatmeal, oregano, papaya, parsley, peony root, pomegranate, *Pongamia glabra* seed, *Pongamia pinnata*, quinoa seed, red raspberry, rose hip, rosemary, sage, saw palmetto, soy bean, szechuan peppercorn, *Tephrosia purpurea, terminalia catappa, Terminalia sericea*, thunder god vine, thyme, turmeric, *Valeriana officinalis*, walnuts, white tea leaf, yam, witch hazel, wormwood, yarrow, valerian, yohimbe, mangosteen, sour sob, goji berry, spirulina and durian skin.

In one preferred embodiment, the invention comprises compositions comprising the biologically active ingredient together with a grinding matrix, a mixture of grinding matrix materials, milling aids, mixtures of milling aids, facilitating agents and/or mixtures of facilitating agents as described herein, in concentrations and ratios as described herein under the methods of the invention.

In a fourth aspect the invention comprises a pharmaceutical composition comprising a biologically active material produced by the method described herein and compositions described herein. Preferably, the invention comprises pharmaceutical compositions comprising the biologically active ingredient together with a grinding matrix, a mixture of grinding matrix materials, milling aids, mixtures of milling aids, facilitating agents and/or mixtures of facilitating agents as described herein, in concentrations and ratios as described herein under the methods of the invention. Preferably, the average particle size of the biologically active material, determined on a particle number basis, is equal to or less than a size selected from the group 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size of the biologically active material is equal to or greater than 25 nm. Preferably, the particles of the biologically active material have a median particle size, determined on a particle volume basis, equal or less than a size selected from the group 20,000 nm, 15,000 nm, 10,000 nm, 8000 nm, 6000 nm, 5000 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size of the biologically active material is equal to or greater than 25 nm. Preferably, the percentage of particles, on a particle volume basis, is selected from the group consisting of: 50%, 60%, 70%, 80%, 90%, 95% and 100% less than 20,000 nm (%<20,000 nm). Preferably, the percentage of particles, on a particle volume basis, is selected from the group consisting of: 50%, 60%, 70%, 80%, 90%, 95% and 100% less than 10,000 nm (%<10,000 nm). Preferably, the percentage of particles, on a particle volume basis, is selected from the group consisting of: 50%, 60%, 70%, 80%, 90%, 95% and 100% less than 5000 nm (%<5000 nm). Preferably, the percentage of particles, on a particle volume basis, is selected from the group consisting of: 50%, 60%, 70%, 80%, 90%, 95% and 100% less than 2000 nm (%<2000 nm). Preferably, the percentage of particles, on a particle volume basis, is selected from the group consisting of: 50%, 60%, 70%, 80%, 90%, 95% and 100% less than 1000 nm (%<1000 nm). Preferably, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). Preferably, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). Preferably, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). Preferably, the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to 90. Preferably, the biologically active material is selected from the group consisting of: fungicides, pesticides, herbicides, seed treatments, cosmeceuticals, cosmetics, complementary medicines, natural products, vitamins, nutrients, nutraceuticals, pharmaceutical actives, biologics, amino acids, proteins, peptides, nucleotides, nucleic acids, additives, foods and food ingredients and analogs, homologs and first order derivatives thereof. Preferably, the biologically active material is selected from the group consisting of: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthenes. Preferably, the biologically active material is selected from the group consisting of: indomethacin, diclofenac, naproxen, meloxicam, metaxalone, cyclosporin A, progesterone celecoxib, cilostazol, ciprofloxacin, 2,4-dichlorophenoxyacetic acid, anthraquinone, creatine monohydrate, glyphosate, halusulfuron, mancozeb, metsulfuron, salbutamol, sulphur, tribenuran and estradiol or any salt or derivative thereof. In a preferred embodiment, the composition is adapted for delivery by inhalation, intranasal delivery and/or pulmonary delivery.

In a fifth aspect the invention comprises a method of treating a human in need of such treatment comprising the step of administering to the human an effective amount of a pharmaceutical composition as described herein. In a preferred embodiment, the composition is administered by inhalation, intranasal delivery and/or pulmonary delivery.

In a sixth aspect, the invention comprises the use of a pharmaceutical composition as described herein in the manufacture of a medicament for the treatment of a human in need of such treatment. In a preferred embodiment, the medicament is adapted to be administered by inhalation, intranasal delivery and/or pulmonary delivery.

In a seventh aspect the invention comprises a method for manufacturing a pharmaceutical composition as described herein comprising the step of combining a therapeutically effective amount of a biologically active material prepared by a method described herein or a composition as described herein, together with a pharmaceutically acceptable carrier to produce a pharmaceutically acceptable dosage form.

In a eighth aspect the invention comprises a method for manufacturing a veterinary product comprising the step of combining a therapeutically effective amount of the biologically active material prepared by a method as described herein or a composition as described herein, together with an acceptable excipient to produce a dosage form acceptable for veterinary use.

In an nineth aspect the invention comprises a method for manufacturing an agricultural product comprising the step of combining an effective amount of the biologically active material prepared by a method described herein or a composition as described herein. Preferably the agricultural product is combined with an acceptable excipient to produce a formulation such as, but not limited to a water dispersible granule, wettable granule, dry flowable granule or soluble granule that is used to prepare a solution for use in agricultural applications. Preferably, the product is selected from the group consisting of: herbicides, pesticides, seed treatments, herbicide safeners, plant growth regulators and fungicides. The methods of the invention can be used to increase the dissolution of the biologically active material particles in water or other solvents, resulting in better, faster or more complete preparation and mixing. This will result in a more consistent product performance such as better weed, disease and pest control and other practical benefits such as faster machinery, tank and sprayer cleanout, less rinsate, and a reduced impact on the environment.

In another aspect of the method of invention, the invention provides methods to produce powders that have active particles with a high surface area. Such powders would provide better performance in areas such as seed treatment where dry powders are applied to seeds as fungicides, herbicide safeners, plant growth regulators and other treatments. The higher surface area would provide more activity per mass of active used.

In another preferred aspect, actives such as pesticides, fungicides and seed treatments subject to the method of invention are formulated to produce suspensions of the actives when added to water or other solvents. As these suspensions will have particles of very small size and high surface area they will possess at least three highly desirable traits. The first is that small particles with high surface area will adhere better to surfaces such as leafs and other foliage that the suspension is applied to. This will result in better rain fastness and a longer period of activity. The second aspect is that smaller particles with a higher surface area deliver superior coverage per unit mass of active applied. For example, if 100 particles are needed on a leaf and if the particle diameter is reduced to one third of the former diameter by the methods of this invention, then the dosage can be reduced to about 11% of the former dosage, resulting in lower cost, less residue on harvested crops, and mitigation of environmental impact. In the third aspect the smaller particles will deliver better bioavailability. With many low solubility actives, such as fungicides and pesticides the particles that adhere to plant material slowly dissolve over days and weeks providing continued protection from disease and pests. With this method of invention able to deliver better bioavailability in many circumstances it will be possible to reduce the amount of active that needs to be applied. As with the second aspect such an outcome would lower costs, minimize residues and mitigate environmental impact. In a highly preferred aspect of the invention the powder produced in the milling process would be subject to a process such as wet or dry granulation that makes the powder free flowing and low in dust content yet easily dispersible once in water or other solvent.

Preferably the biologically active material is a herbicide, pesticide, seed treatment, herbicide safener, plant growth regulator or fungicide selected from the group consisting of: 2-phenylphenol, 8-hydroxyquinoline sulfate, acibenzolar, allyl alcohol, azoxystrobin, basic benomyl, benzalkonium chloride, biphenyl, blasticidin-S, Bordeaux mixture, Boscalid, Burgundy mixture, butylamine, Cadendazim, calcium polysulfide, Captan, carbamate fungicides, carbendazim, carvone, chloropicrin, chlorothalonil, ciclopirox, clotrimazole, conazole fungicides, Copper hydroxide, copper oxychloride, copper sulfate, copper(II) carbonate, copper(II) sulfate, cresol, cryprodinil, cuprous oxide, cycloheximide, Cymoxanil, DBCP, dehydroacetic acid, dicarboximide fungicides, difenoconazole, dimethomorph, diphenylamine, disulfiram, ethoxyquin, famoxadone, fenamidone, Fludioxonil, formaldehyde, fosetyl, Fosetyl-aluminium, furfural, griseofulvin, hexachlorobenzene, hexachlorobutadiene, hexachlorophene, hexaconazole, imazalil, Imidacloprid, iodomethane, Iprodione, Lime sulfur, mancozeb, mercuric chloride, mercuric oxide, mercurous chloride, Metalaxyl, metam, methyl bromide, methyl isothiocyanate, metiram, natamycin, nystatin, organotin fungicides, oxythioquinox, pencycuron, pentachlorophenol, phenylmercury acetate, potassium thiocyanate, procymidone, propiconazole, propineb, pyraclostrobin, pyrazole fungicides, pyridine fungicides, pyrimethanil, pyrimidine fungicides, pyrrole fungicides, quinoline fungicides, quinone fungicides, sodium azide, streptomycin, sulfur, Tebucanazole, thiabendazole, thiomersal, tolnaftate, Tolylfluanid, triadimersol, tributyltin oxide, Trifloxystrobin, triflumuron, Undecylenic acid, urea fungicides, vinclozolin, Ziram,3-dihydro-3-methyl-1, 3-thiazol-2-ylidene-xylidene, 4-D esters, 4-DB esters, 4-parathion methyl, Acetamiprid, aclonifen, acrinathrin, alachlor, allethrin, alpha-cypermethrin, Aluminium phosphide, amitraz, anilophos, azaconazole, azinphos-ethyl, azinphos-methyl, benalaxyl, benfluralin, benfuracarb, benfuresate, bensulide, benzoximate, benzoylprop-ethyl, betacyfluthrin, beta-cypermethrin, bifenox, bifenthrin, binapacryl, bioallethrin, bioallethrin S, bioresmethrin, biteranol, Brodifacoum, bromophos, bromopropylate, bromoxynil, bromoxynil esters, bupirimate, buprofezin, butacarboxim, butachlor, butamifos, butoxycarboxin, butralin, butylate, calcium sulfate, cambda-cyhalothrin, carbetamide, carboxin, chlordimeform, chlorfenvinphos, chlorflurazuron, chlormephos, chlornitrofen, chlorobenzilate, chlorophoxim, chloropropylate, chlorpropham, Chlorpyrifos, chlorpyrifosmethyl, cinmethylin, clethodim, clomazone, clopyralid esters, CMPP esters, cyanophos, cycloate, cycloprothrin, cycloxydim, cyfluthrin, cyhalothrin, cypermethrin, cyphenothrin, cyproconazole, deltamethrin, demeton-S-methyl, desmedipham, dichlorprop esters, dichlorvos, diclofop-methyldiethatyl, dicofol, difenoconazole, dimethachlor, dimethomoph, diniconazole, dinitramine, dinobuton, dioxabenzafos, dioxacarb, disulfoton, ditalimfos, dodemorph, dodine, edifenphos, emamectin, empenthrin, endosulfan, EPNethiofencarb, epoxyconazole, esfenvalerate, ethalfluralin, ethofumesate, ethoprophos, ethoxyethyl, etofenprox, etridiazole, etrimphos, Famoxadone, fenamiphos, fenarimol, fenazaquin, fenitrothion, fenobucarb, fenoxapropethyl, fenoxycarb, fenpropathrin, fenpropidin, fenpropimorph, fenthiocarb, fenthion, fenvalerate, fluazifop, fluazifop-P, fluchloralin, flucythrinate, flufenoxim, flufenoxuron, flumetralin, fluorodifen, fluoroglycofen ethyl, fluoroxypyr esters, flurecol butyl, flurochloralin, flusilazole, formothion, gamma-HCH, haloxyfop, haloxyfop-methyl, hexaflumuron, hydroprene, imibenconazole, indoxacarb, ioxynil esters, isofenphos, isoprocarb, isopropalin, isoxathion, malathion, maneb, MCPA esters, mecoprop-P esters, mephospholan, Metaldehyde, methidathion, Methomyl, methoprene, methoxychlor, metolachlor, mevinphos, monalide, myclobutanil, N-2, napropamide, nitrofen, nuarimol, oxadiazon, oxycarboxin, oxyfluorfen, penconazole, pendimethalin, permethrin, phenisopham, phenmedipham, phenothrin, phenthoate, phosalone, phosfolan, phosmet, picloram esters, pirimicarb, pirimiphos-ethyl, pirimiphos-methyl, pretilachlor, prochloraz, profenofos profluralin, promecarb, propachlor, propanil, propaphos, propaquizafop, propargite, propetamphos, pymetrozine, pyrachlofos, pyridate, pyrifenox, quinalphos, quizalofop-P, resmethrin, Spinetoram J, Spinetoram L, Spinosad A, Spinosad B, tau-fluvalinate, tebuconazole, Tebufenozide, tefluthrin, temephos, terbufos, tetrachlorinphos, tetraconazole, tetradifon, tetramethrin, Thiamethoxam, tolclofos-methyl, tralomethrin, triadimefon, triadimenol, triazophos, triclopyr esters, tridemorph, tridiphane, triflumizole, trifluralin, xylylcarb, 3-dihydro-3-methyl-1, 3-thiazol-2-ylidene-xylidene, 4-D esters, 4-DB esters, 4-parathion methyl, Acetamiprid, acetochlor, aclonifen, acrinathrin, alachlor, allethrin, alpha-cypermethrin, Aluminium phosphide, amitraz, anilophos, azaconazole, azinphos-ethyl, azinphos-methyl, benalaxyl, benfluralin, benfuracarb, benfuresate, bensulide, benzoximate, benzoylprop-ethyl, betacyfluthrin, beta-cypermethrin, bifenox, bifenthrin, binapacryl, bioallethrin, bioallethrin S, bioresmethrin, biteranol, Brodifacoum, bromophos, bromopropylate, bromoxynil, bromoxynil esters, bupirimate, buprofezin, Butacarboxim, butachlor, butamifos, butoxycarboxin, butralin, butylate, calcium sulfate, cambda-cyhalothrin, carbetamide, carboxin, chlordimeform, chlorfenvinphos, chlorflurazuron, chlormephos, chlornitrofen, chlorobenzilate, chlorophoxim, chloropropylate, chlorpropham, Chlorpyrifos, chlorpyrifos-methyl, cinmethylin, clethodim, clomazone, clopyralid esters, CMPP esters, cyanophos, cycloate, cycloprothrin, cycloxydim, cyfluthrin, cyhalothrin, cypermethrin, cyphenothrin, cyproconazole, deltamethrin, demeton-S-methyl, desmedipham, dichlorprop esters, dichlorvos, diclofop-methyldiethatyl, dicofol, dimethachlor, dimethomoph, diniconazole, dinitramine, dinobuton, dioxabenzafos, dioxacarb, disulfoton, ditalimfos, dodemorph, dodine, edifenphos, emamectin, empenthrin, endosulfan, EPNethiofencarb, epoxyconazole, esfenvalerate, ethalfluralin, ethofumesate, ethoprophos, ethoxyethyl, ethoxyquin, etofenprox, etridiazole, etrimphos, fenamiphos, fenarimol, fenazaquin, fenitrothion, fenobucarb, fenoxapropethyl, fenoxycarb, fenpropathrin, fenpropidin, fenpropimorph, fenthiocarb, fenthion, fenvalerate, fluazifop, fluazifop-P, fluchloralin, flucythrinate, flufenoxim, flufenoxuron, flumetralin, fluorodifen, fluoroglycofen ethyl, fluoroxypyr esters, flurecol butyl, flurochloralin, flusilazole, formothion, gamma-HCH, haloxyfop, haloxyfop-methyl, hexaflumuron, hydroprene, imibenconazole, indoxacarb, ioxynil esters, isofenphos, isoprocarb, isopropalin, isoxathion, malathion, maneb, MCPA esters, mecoprop-P esters, mephospholan, Metaldehyde, methidathion, Methomyl, methoprene, methoxychlor, mevinphos, monalide, myclobutanil, myclobutanil, N-2, napropamide, nitrofen, nuarimol, oxadiazon, oxycarboxin, oxyfluorfen, penconazole, permethrin, phenisopham, phenmedipham, phenothrin, phenthoate, phosalone, phosfolan, phosmet, picloram esters, pirimicarb, pirimiphos-ethyl, pirimiphos-methyl, pretilachlor, prochloraz, profenofos, profluralin, promecarb, propachlor, propanil, propaphos, propaquizafop, propargite, propetamphos, pymetrozine, pyridate, pyrifenox, quinalphos, quizalofop-P, resmethrin, Spinetoram J, Spinetoram L, Spinosad A, Spinosad B, tau-fluvalinate, Tebufenozide, tefluthrin, temephos, terbufos, tetrachlorinphos, tetraconazole, tetradifon, tetramethrin, Thiamethoxam, tolclofos-methyl, tralomethrin, triadimenol, triazophos, triclopyr esters, tridemorph, tridiphane, triflumizole, trifluralin, xylylcarb and any combination thereof.

In an ninth aspect the invention comprises a method for manufacturing of a pharmaceutical formulation comprising the step of combining an effective amount of the biologically active material prepared by a method described herein together with acceptable excipients to produce a formulation that can deliver a therapeutically effective amount of active to the pulmonary or nasal area. Such a formulation could be, but is not limited to a dry powder formulation for oral inhalation to the lungs or a formulation for nasal inhalation. Preferably the method for manufacturing such a formulation uses lactose, mannitol, sucrose, sorbitol, xylitol or other sugars or polyols as the co-grinding matrix together with surfactant such as, but not limited to lecithin, DPPC (dipalmitoyl phosphatidylcholine), PG (phosphatidylglycerol), dipalmitoyl phosphatidyl ethanolamine (DPPE), dipalmitoyl phosphatidylinositol (DPPI) or other phospholipid. The particle size of the material produced by the invention disclosed herein results in the materials being readily aerosolized and suitable for methods of delivery to a subject in need thereof, including pulmonary and nasal delivery methods. In a tenth aspect, the invention comprises a method for the manufacture of a composition for industrial application, such as, but not limited to paints, polymers or other functional coatings, comprising the step of combining an effective amount of the active material prepared by a method described herein together with an acceptable excipient to produce a composition that can deliver an active particle such as, but not limited to, a fungicide in solid form to a coating resistant to attack by biologically agents such as, but not limited to, a fungus or algae. Because small particles provide a greater surface coverage of active agent per unit mass than conventionally sized particles less active is required in the composition. The particles generated by the invention would also provide ascetic advantages as they can be incorporated into a coating formulation without the appearance of having particulate matter in the coating. Preferably the method for manufacturing such a composition uses titanium dioxide, silica, sodium chloride or other inorganic salts with a suitable surfactant or polymer. Preferably the active is a fungicide selected from the list of herbicides, pesticides, seed treatments, herbicide safeners, plant growth regulators and fungicides described above.

In an eleventh aspect, the invention comprises a method for the manufacture of a radio-contrast agent for use in radiological examinations. A common example of such an agent would be barium sulfate which is commonly used in examinations of the gastrointestinal tract. Agents such as barium sulfate are essentially insoluble in water and function as discrete particles dispersed throughout the area of examination. Formulations of active material used as radio-contrast agents as prepared by a method described herein with other acceptable excipients could be used to provide enhanced sensitivity and lower toxicity due to the increased surface area provided by the particle size reduction. The increased surface area will provide greater coverage of the tissue to be measured providing better contrast. If the agent has toxic side effects greater contrast per unit mass would allow for less contrast agent to be used compared with conventional formulations. Another advantage of preparing such a formulation using the method described herein is the ability to administer that contrast agent as a dry formulation thus eliminating undesirable aspects of drinking a liquid formulation.

In a twelfth aspect, the invention comprises a method for the manufacture of a composition for use as a food product where the production of small particles has other functional advantages in addition to a faster dissolution of the active. One example would be where the active agent is cocoa or cocoa derived solids. When cocoa is processed in the manufacture of chocolate the particle size must be reduced below a size threshold such that the chocolate has a smooth feel when eaten. In the same way better flavour is thought to come from small cocoa particles. Premium chocolate is known to have a small particle size distribution. By combining an appropriate amount of the active material, such as cocoa, cocoa powder, cocoa nibs, cocoa mass or cocoa liquor prepared by a method described herein together with other food ingredients a food product such as chocolate can be prepared. This can be done to both enhance existing food products such as chocolate or provide a more efficient and less costly process for some aspects of the food product manufacture. Another aspect of this invention is the preparation of a food product for drinking by combining an appropriate amount of the active material, such as cocoa, cocoa powder, cocoa nibs, cocoa mass, cocoa liquor or coffee, prepared by the method described herein together with other food ingredients. Materials produced using this invention, having very small particles, could be directly used in drink products without leaving residue in the products due to large particle size. An example of this would be a drinking cocoa or drinking chocolate were a cocoa material could be milled with a matrix such as but not limited to sugar, glucose or lactose. Apart from greater release of flavours, such a product could directly use the natural product where conventional food products only use water soluble extracts. A clear example of this is coffee products. Instant coffee provides a convenient form of the product but is made by extracting flavor from coffee beans and then processing it into a soluble powder. In doing so some of the complex flavor of coffee is lost. In comparison, coffee made from ground coffee beans provides an enhanced flavor rich drink but requires greater preparation and often uses expensive apparatuses. Some coffee styles used ground coffee beans directly in a cup but this method leaves a thick sludge in the bottom of the cup. Material produced by the method described herein would overcome these limitations of the prior art. By preparing the composition from coffee beans the full flavor can be accessed and the small particle size produced by this invention produces a drink where the particles are suspended in the liquid which do not form a thick sludge. A further advantage of this invention is that the material produced is a dry powder which can then be easily packaged or processed further to provide a saleable product. A further advantage of of this invention is that natural products such as coffee are encapsulated into the carrier matrix and thus have superior powder handling properties compared to natural products milled on there own. Materials such as coffee can be milled in high energy mills to produce particles with small size but the material is sticky and hard to handle. Other technologies, such as wet milling would be more costly as further processing, like spray drying, would be required to produce a powder. Preferred matrices used for milling in this aspect include, but are not limited to, lactose, sucrose, fructose, mannitol, glucose, xylitol, milk powders, other milk solids and lethicin. In one embodiment, the particles of biologically active material of the invention are a size equal to or less than 20,000 nm. In one embodiment, the particles of biologically active material of the invention are a size equal to or less than 10,000 nm. In one embodiment, the particles of biologically active material of the invention are a size equal to or less than 5,000 nm.

While the method of the present invention has particular application in the preparation of poorly water-soluble biologically active materials, the scope of the invention is not limited thereto. For example, the method of the present invention enables production of highly water-soluble biologically active materials. Such materials may exhibit advantages over conventional materials by way of, for example, more rapid therapeutic action or lower dose. In contrast, wet grinding techniques utilizing water (or other comparably polar solvents) are incapable of being applied to such materials, as the particles dissolve appreciably in the solvent.

Other aspects and advantages of the invention will become apparent to those skilled in the art from a review of the ensuing description.

BRIEF DESCRIPTION OF THE DRAWINGS

FIG. 1A. Powder charge composition and particle size distribution of material milled in SPEX mill, examples A to S.

FIG. 1B. Powder charge composition and particle size distribution of material milled in SPEX mill, examples T to AL.

FIG. 1C. Powder charge composition and particle size distribution of material milled in SPEX mill, examples AM to BE.

FIG. 1D. Powder charge composition and particle size distribution of material milled in SPEX mill, examples BF to BX.

FIG. 1E. Powder charge composition and particle size distribution of material milled in SPEX mill, examples BY to CQ.

FIG. 1F. Powder charge composition and particle size distribution of material milled in SPEX mill, examples CR to DJ.

FIG. 1G. Powder charge composition and particle size distribution of material milled in SPEX mill, examples DK to EC.

FIG. 2A. Powder charge composition and particle size distribution of material milled in 110 mL HD01 Attritor mill, examples A to F.

FIG. 3A. Powder charge composition and particle size distribution of material containing a mixture of 2 matrices, milled in SPEX mill, examples A to E.

FIG. 4A. Powder charge composition and particle size distribution of material milled in 1 L HD01 Attritor mill, examples A to G.

FIG. 5A. Powder charge composition and particle size distribution of material milled in 750 mL 1S Attritor mill, examples A to F.

FIG. 6A. Powder charge composition and particle size distribution of material milled in ⅞ Gallon 1S Attritor mill, examples A to R.

FIG. 6B. Powder charge composition and particle size distribution of material milled in ⅞ Gallon 1S Attritor mill, examples S to AK.

FIG. 6C. Powder charge composition and particle size distribution of material milled in ⅞ Gallon 1S Attritor mill, examples AL to AU.

FIG. 7A. Powder charge composition and particle size distribution of Metaxalone milled in a variety of mills, examples A to O.

FIG. 8A. Powder charge composition and particle size distribution of material milled in HICOM mill, examples A to P.

FIG. 9A. Powder charge composition and particle size distribution of material milled in 1% Gallon 1S Attritor mill, examples A to S.

FIG. 9B. Powder charge composition and particle size distribution of material milled in 1% Gallon 1S Attritor mill, examples T to AL.

FIG. 10A. Powder charge composition and particle size distribution of material milled in a variety of large scale mills, examples A to F.

FIG. 11A. Powder charge composition and particle size distribution of food grade material milled in SPEX mill, examples A to S.

FIG. 11B. Powder charge composition and particle size distribution of food grade material milled in SPEX mill, examples T to AC.

FIG. 11C. Powder charge composition and particle size distribution of food grade material milled in SPEX mill, examples AD to AV.

FIG. 12A. Powder charge composition and particle size distribution of food grade material milled in ⅞ Gallon 1S Attritor mill, examples A to F.

FIG. 12B: Photos at the end of the milling in example 12 sample B.

FIG. 13A. Powder charge composition and particle size distribution of Naproxen Acid milled in Mannitol in a ⅞ Gallon 1S Attritor mill, examples A to M.

FIG. 14A. Powder charge composition and particle size distribution of Naproxen Acid milled in SPEX mill and particle size distribution after filtration, examples A to L.

FIG. 15: Table describing the milling of various actives and some matrices without active and the particle size of these actives as well as the particle size of actives in a variety of other blends made for powder handling characteristic testing.

FIG. 16: Powder adherence, angle of repose and particle size as measured by dry powder laser diffraction of various actives/blends from example 16

DETAILED DESCRIPTION OF THE INVENTION

General

Figure 1H:
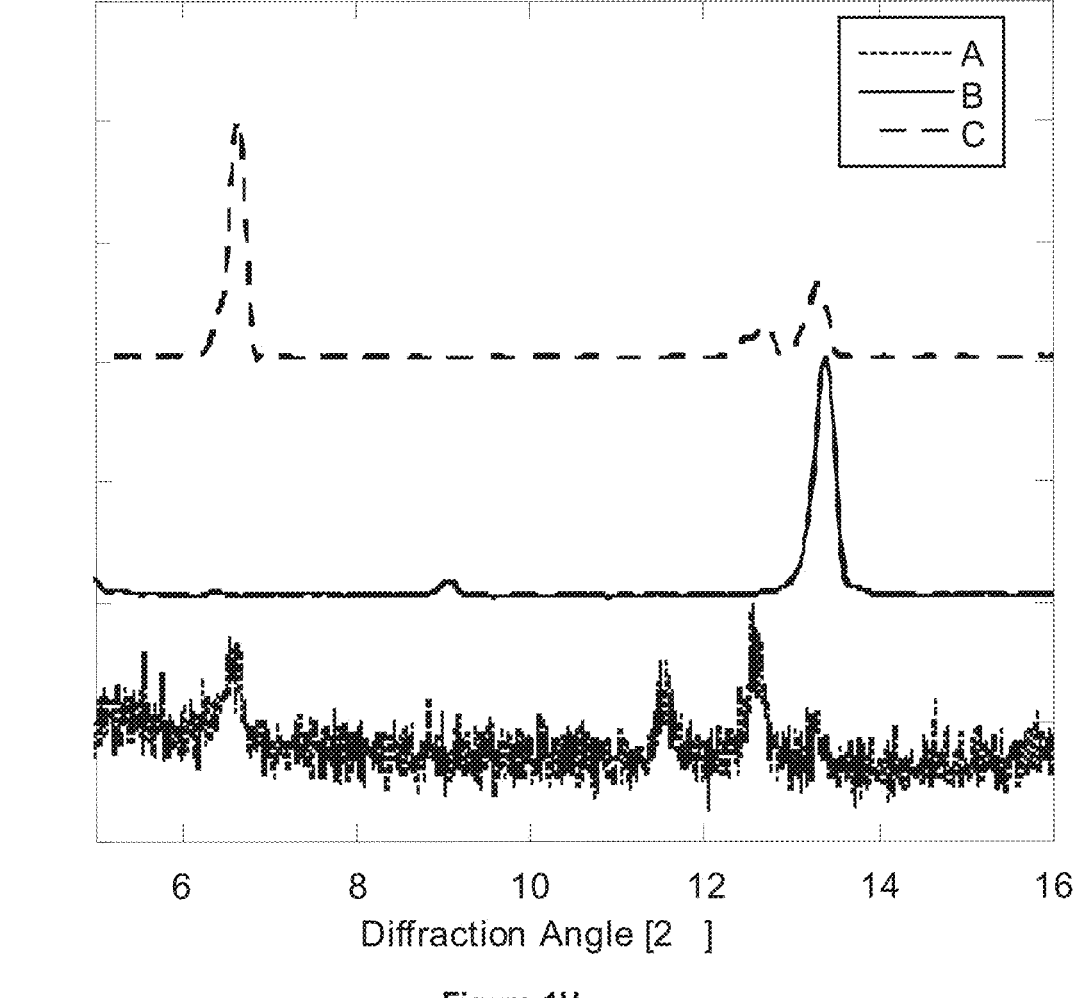
FIG. 1H. The figure shows the X-Ray diffraction patterns: (A) after milling of Naproxen sodium in tartaric acid; (B) unmilled Naproxen sodium and (C) unmilled Naproxen acid.

Those skilled in the art will appreciate that the invention described herein is susceptible to variations and modifications other than those specifically described. It is to be understood that the invention includes all such variations and modifications. The invention also includes all of the steps, features, compositions and materials referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this invention relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "biologically active material" is defined to mean a biologically active compound or a substance which comprises a biologically active compound. In this definition, a compound is generally taken to mean a distinct chemical entity where a chemical formula or formulas can be used to describe the substance. Such compounds would generally, but not necessarily be identified in the literature by a unique classification system such as a CAS number. Some compounds may be more complex and have a mixed chemical structure. For such compounds they may only have an empirical formula or be qualitatively identified. A compound would generally be a pure material, although it would be expected that up to 10%, 20%, 30%, 40%, 50%, 60%, 70%, 80%, 90% of the substance could be other impurities and the like. Examples of biologically active compounds are, but not limited to, fungicides, pesticides, herbicides, seed treatments, cosmeceuticals, cosmetics, complementary medicines, natural products, vitamins, nutrients, nutraceuticals, pharmaceutical actives, biologics, amino acids, proteins, peptides, nucleotides, nucleic acids, additives, foods and food ingredients and analogs, homologs and first order derivatives thereof. A substance that contains a biologically active compound is any substance which has as one of its components a biologically active compound. Examples of substances containing biologically active compounds are, but not limited to, pharmaceutical formulations and products, cosmetic formulations and products, industrial formulations and products, agricultural formulations and products, foods, seeds, cocoa and cocoa solids, coffee, herbs, spices, other plant materials, minerals, animal products, shells and other skeletal material.

Any of the terms, "biological(ly) active", "active", "active material" shall have the same meaning as biologically active material.

The term "grinding matrix" is defined as any inert substance that a biologically active material can or is combined with and milled. The terms "co-grinding matrix" and "matrix" are interchangeable with "grinding matrix".

The term "of the same, similar or larger particle size" is defined as where the median (by volume) particle size of an active material produced by a conventional manufacturing process is the same, with a median size+/−20%; similar, with a median size+/−5 micron; or larger, where the median size is greater than the particle size of an active material produced by the process described herein but is less than or equal to 20 micron.

The term "conventional process" is defined as another (different to the one described herein) dry manufacturing process where a biologically active material is subject to particle size reduction. Examples of such processes are, but are not limited to, conventional ball milling (where no matrix is present or the active material is greater than 80% w/w), pin mills, air jet mills or other fluid energy mills The term "nanoparticle" is defined as having a median diameter (by volume) of 1000 nm or less.

The term "microparticle" is defined as having a median diameter (by volume) of 1000 nm to 20,000 nm inclusive The term "composite particle" is defined as the combination of nanopaticle and/or microparticles of a biologically active material together with the particles of the grinding matrix (milled or partially milled) into a larger particle.

The term "blend" is defined as the resultant mixture of a biologically active material and excipient particles combined together in a process that has the effect or intended effect of distributing the active and excipient particles in a uniform distribution throughout the final powder blend. In this definition the term excipient and matrix are interchangeable. An ensemble of composite particles as produced by the invention described herein is one example of a blend. Preferably a blend is made using simple blending processes that do not involve granulation but may involve a milling step.

The term "content uniformity" is defined as the measure of how evenly an active material is distributed throughout a blend. A blend with superior content uniformity will have the same concentration of active in many samples taken from different places (eg: top middle and bottom) in a blend. Typically content uniformity is measured by assaying the sample by HPLC or similar technique to determine the concentration of active in a sample. Typically content uniformity is expressed as the % deviation of the many samples from the known concentration of the whole blend.

The term "segregation" is stratification of the particle size distribution of a powder or blend. It can be caused by any physical process, but typically it occurs when a powder or blend undergoes flow or other movement. Examples of processes that can introduce segregation are, but not limited to, transport, blending and flow in a hopper or other processing equipment. A powder or blend in an unsegregated state will have an even distribution of particle sizes throughout the whole powder or blend such that any sample taken from any part of the bag or container holding the powder (such as top, middle, bottom) will give the same particle size distribution. In a powder that has undergone segregation some parts of the powder will have more large particles that other parts and some parts will have more small particles than other parts of the powder. In a powder with segregation samples taken from a variety of positions in the bag or container holding the powder (such as top, middle, bottom) will typically show some difference in the particle size distribution.

Blends and Composite Particles

A conventional approach to reducing the size (in a dry process) of active particles is fluid energy milling. An example of this is airjet milling (also known as micronisation). This technique and other similar milling techniques typically reduced the particle size to between 2 and 10 micron. The powder that results from air milling typically has poor powder handling characteristics. This powder is often cohesive, has poor flow properties, has high static charge and low bulk density. In order to process this micronized active material into a product such as, but not limited to, a solid oral dose or inhaled powder, it must first be processed into a suitable blend with other excipients. The creation of a blend is not a trivial process with the poor handling properties of a micronized material making any process difficult. The creation of the blend has many benefits such as diluting the active to lower doses, bulking the active up to make dosage forms of a practical size and the creation of a powder with superior flow properties making it easier to handle in subsequent manufacturing processes, such as granulation or tabletting.

To create a blend with improved powder handling properties, excipients with a particle size significantly larger than the micronized active could be used. However, this approach has the disadvantage of potential segregation during the blending or subsequent process. If the segregation of such a blend occurs, the content uniformity will be poor which is highly undesirable in pharmaceutical manufacturing. If excipients with a particle size similar to the micronized active are used, then segregation is less likely but the powder handling properties of the material would be poor. In practice a compromise is usually undertaken whereby an intermediate sized excipient is used. In this case, careful blending and processing can maintain acceptable content uniformity and the powder handling properties are improved enough to facilitate further processing such as wet or dry granulation.

If a high level of content uniformity is required an alternative approach would be to process the excipient and active in an airjet mill together. This process would create a blend where the excipient and active have almost identical particle size thus preventing segregation. However this material would have poor powder handling properties and would require careful handling in subsequent processes. This material would likely need to be wet or dry granulated.

In a surprising and unexpected discovery, the invention described herein overcomes both of these problems. Even more surprising is that the invention overcomes these problems even when the active particles produced in the milling process are significantly smaller than active particles produced in conventional milling process such as air jet milling. One skilled in the art would expect that if 2 $\mu$m particles have poor powder handling properties then 200 nm particles would have significantly poorer powder handling properties.

It is thought that the process described herein overcomes both the issue of poor powder handling and poor content uniformity by the simultaneous production of active nanoparticles and/or microparticle, the blending of these with the grinding matrix (excipients) and the formation of composite particles of the active particles and matrix particles. In this way, powder with three clear benefits is produced in a "one pot" process. Firstly, active nanoparticles and/or microparticle are made, secondly, the particle size of the blend produced is large enough to give superior powder handling properties compared to conventional methods and, thirdly, the formation of the composite particles deliveries robust content uniformity.

It is thought that during the process described herein the active particles are uniformly distributed throughout the composite particles so that each composite particle contains the same proportion of active and excipient. This means that even if segregation were to occur, the blend would retain superior content uniformity. In contrast, a conventional blend made with active particles smaller than the excipient particles would have poor content uniformity if the blend were to segregate.

Those skilled in the art recognise that it is beneficial to measure the particle size distribution of a powder or blend of powders because this information can be used to predict the powder handling properties. Methods use to determine the particle size of powders are well known in the art. Some common methods include laser diffraction measurements of a stream of the powder dispersed in air. Laser diffraction measurements can also be made in solvents where the solvent does not dissolve any of the powder or particles in the powder. The same methods can be used to determine the size distribution of a powder blend or, in the case of the invention herein, the composite particles. In the case of this invention, the particle size distribution of the composite and the blend are the same thing. In the case where a solvent based measurement is used to characterise the composite particles, care must be taken to ensure that the solvent does not break up the composite as this will not give a true indication of the composite behaviour as a dry powder. For this reason it is preferable to measure the particle size distribution of the composites using a dry powder method such as air dispersion coupled with laser diffraction.

Preferably, the blend particles have a median particle size, determined on a particle volume basis, equal or greater than a size selected from the group consisting of: 2000 nm, 3000 nm, 4000 nm, 5000 nm, 6000 nm, 8000 nm, 10,000 nm, 15,000 nm, 20,000 nm. Preferably, the median particle size is equal to or less than 50 micron.

Preferably, the blend particles have a volume weighted mean (D4,3) equal or greater than a size selected from the group consisting of: 5000 nm, 10,000 nm, 15,000 nm, 20,000 nm, 25,000 nm, 35,000 nm, 40,000 nm Preferably, the median particle size is equal to or less than 70 micron.

Preferably, the percentage of particles in the blend, on a particle volume basis, is selected from the group consisting of: greater than 2 micron (%>2 micron) is selected from the group 50%, 60%, 70%, 80%, 85%, 90% and 95%; greater than 10 micron (%>10 micron) is selected from the group 10%, 20%, 30%, 40%, 50%, 60%, 70%, 80%, 85%, 90% and 95%; equal to or less than 20 micron (%<20 micron) is selected from the group 10%, 20%, 30%, 40%, 50%, 60%, 70%, 80%, 90%, 95% and 100%

Powder Handling Characteristics

The expression "powder handling characteristics" refers to, but is not limited to, at least one of the product's flow properties; static charge, aggregation properties, cohesive properties, uniformity properties, content uniformity, content uniformity after segregation, dust levels, powder rheology, segregation properties, bulk density, powder flow, compressibility, permeability and/or ignition properties. The process described herein to mill biologically active material and generate reduced particle size wherein the powders and/or blends made by the process of the present invention have powder handling properties that are superior to those of powders made by a conventional process delivering the same, similar or larger particle size of the biologically active material when the product: is stored in vials, bags, containers or other closures; is dispensed; is blended; is granulated (wet or dry); is packaged or filled and processed and/or transported during other manufacturing steps.

In one preferred embodiment, the powder handling characteristics of the biologically active material subject to this invention is an improvement over the powder handling characteristics of a biologically active material of the same, similar or larger particle size manufactured using a conventional process. Preferably, the biologically active material subject to this invention has superior powder flow properties compared to the powder flow properties of a biologically active material with the same, similar or larger particle size manufactured using a conventional process. This is a particular advantage during processing of the material. Preferably, the biologically active material subject to this invention has a lower static charge compared to the static charge of a biologically active material with the same, similar or larger particle size manufactured using a conventional process. Preferably the static charge of the product is selected from the group consisting of: less than 10 nC/g, less than 5 nC/g, less than 3 nC/g, less than 2 nC/g, less than 1.5 nC/g, less than 1.25 nC/g, less than 1 nC/g less than 0.75 nC/g, less than 0.5 nC/g, less than 0.25 nC/g or less than 0.1 nC/g. Preferably, the biologically active material subject to this invention has a lower cohesiveness profile compared to the cohesiveness profile of a biologically active material with the same, similar or larger particle size manufactured using a conventional process. Preferably the specific energy (were a lower value indicates less cohesiveness), as measured by powder rheology, of the product is selected from the group consisting of: less than 12 mJ/g, less than 10 mJ/g, less than 9 mJ/g, less than 8 mJ/g, less than 7 mJ/g, less than 6 mJ/g, less than 5 mJ/g less than 4 mJ/g or less than 3 mJ/g. Preferably, the biologically active material subject to this invention has a lower propensity for aggregation compared to the propensity for aggregation of a biologically active material with the same, similar or larger particle size manufactured using a conventional process. Preferably, the biologically active material subject to this invention has a lower propensity for adherence to other materials such as but not limited to stainless steel, glass, plastic, polyethylene and polypropylene compared to the propensity for adherence of a biologically active material with the same, similar or larger particle size manufactured using a conventional process.

Preferably, the biologically active material subject to this invention has increased uniformity compared to a biologically active material with the same, similar or larger particle size manufactured using a conventional process. Preferably the biological active material maintains its superior uniformity despite numerous process steps and modifications to the material. Preferably, the biological active material maintains its superior uniformity despite some level of segregation. For example, even if the biological material particles of varying size segregate, a uniform amount of active is maintained in the particles. Preferably the content uniformity of the biologically active material throughout the blend (even after segregation) varies from the average content by a percentage less than or equal to a percentage selected from the group consisting of: 0.1%, 0.2%, 0.3%, 0.4%, 0.5% 0.75%, 1.0%, 1.5%, 2.0%, 3.0%, 4.0% and 5.0%.

Preferably, the composite particles made by the methods of the invention comprises both biologically active material and matrix material and these composite particles have increased uniformity compared to matter made by conventional processes. This has advantages in the preparation of pharmaceuticals whereby the composite particles made by the methods of the invention is ready to use and does not require the addition of further excipients to bulk up the matter so that it can be formulated. In addition, the composite particles made by the methods of the invention comprises both biologically active material and matrix material and these composite particles have superior flow properties compared to those made by conventional processes.

This translates into significant advantages in the preparation of nanoparticle and/or microparticles. For example, during the formulation of micronized actives by a conventional process, the actives must be blended with bulking excipients and then further processed (dry or wet granulation to improve product flow) carefully so as to avoid segregation of poor content uniformity. However, actives made by this invention (which can be made at sizes less than 1 μm, which the skilled addressee would expect to have significantly worse segregation problems) are in the same process made into composite particles with the matrix material thus having superior uniformity properties compared to actives made by conventional processes, and do not need further processing steps.

Preferably, the biologically active material subject to this invention has reduced levels of dust compared to a biologically active material with the same, similar or larger particle size manufactured using a conventional process. Preferably, the biologically active material subject to this invention has improved rheology compared to a biologically active material with the same, similar or larger particle size manufactured using a conventional process.

Preferably the sheer Stress of the product is selected from the group: less than 3 kPa, less than 2.75 kPa, less than 2.5 kPa, less than 2.35 kPa, less than 2.25 kPa, less than 2.1 kPa, less than 2.0 kPa, less than 1.85 kPa, less than 1.75 kPa, less than 1.50 kPa, less than 1.25 kPa or less than 1.0 kPa. Preferably the basic flow energy of the product is selected from the group: less than 500 mJ, less than 450 mJ, less than 400 mJ, less than 375 mJ, less than 350 mJ, less than 325 mJ, less than 300 mJ, or less than 250. Preferably, the biologically active material subject to this invention has reduced segregation compared to a biologically active material with the same, similar or larger particle size manufactured using a conventional process. Preferably, the biologically active material subject to this invention has increased bulk density or tapped bulk density compared to a biologically active material with the same, similar or larger particle size manufactured using a conventional process. Preferably the bulk density of the product is selected from the group consisting of: greater than 0.3 g/ml, greater than 0.4 g/ml, greater than 0.45 g/ml, greater than 0.5 g/ml, greater than 0.55 g/ml, greater than 0.60 g/ml, greater than 0.65 g/ml, greater than 0.7 g/ml, greater than 0.75 g/ml, greater than 0.80 g/ml, greater than 0.85 g/ml. greater than 0.90 g/ml or greater than 1.0 g/ml. Preferably the tapped bulk density of the product is selected from the group consisting of: greater than 0.3 g/ml, greater than 0.4 g/ml, greater than 0.45 g/ml, greater than 0.5 g/ml, greater than 0.55 g/ml, greater than 0.60 g/ml, greater than 0.65 g/ml, greater than 0.7 g/ml, greater than 0.75 g/ml, greater than 0.80 g/ml, greater than 0.85 g/ml. greater than 0.90 g/ml or greater than 1.0 g/ml. Preferably, the biologically active material subject to this invention has superior powder flow as defined by the Hausner ratio or Carr's index compared to a biologically active material with the same, similar or larger particle size manufactured using a conventional process. Preferably, the biologically active material subject to this invention has lower compressibility compared to a biologically active material with the same, similar or larger particle size manufactured using a conventional process. Preferably the % compressibility, as measured using a powder rheometer is less than the % selected for the group: 30, 25, 20, 17, 15, 13 and 10. Preferably, the biologically active material subject to this invention has increased permeability compared to a biologically active material with the same, similar or larger particle size manufactured using a conventional process. Preferably the pressure drop (where a low pressure drop indicates superior permeability), as measured as the pressure drop across a bed of powder in a powder rheometer, is selected for the group consisting of: less than 20 mBar, less than 15 mBar, less than 10 mBar, less than 7 mBar, less than 5 mBar, less than 4 mBar or less than 3 mBar. Preferably, the biologically active material subject to this invention has a higher minimum ignition energy compared to a biologically active material with the same, similar or larger particle size manufactured using a conventional process. Preferably, the biologically active material subject to this invention has higher hopper flow rates compared to a biologically active material with the same, similar or larger particle size manufactured using a conventional process. Preferably, the biologically active material subject to this invention has smaller critical orifice diameter compared to a biologically active material with the same, similar or larger particle size manufactured using a conventional process. Preferably, the biologically active material subject to this invention has smaller angle of repose compared to a biologically active material with the same, similar or larger particle size manufactured using a conventional process. Preferably, the biologically active material subject to this invention has smaller dynamic angle of repose compared to a biologically active material with the same, similar or larger particle size manufactured using a conventional process.

In one preferred embodiment, the powder handling characteristics of a blend made using this invention is an improvement over the powder handling characteristics of a blend (containing biologically active material of the same, similar or larger particle size) manufactured using a conventional process. Preferably, the blend made using this invention has superior powder flow properties compared to the powder flow properties of a blend (containing biologically active material of the same, similar or larger particle size) manufactured using a conventional process. This is a particular advantage during processing of the material. Preferably, the blend made using this invention has a lower static charge compared to the static charge of a blend (containing biologically active material of the same, similar or larger particle size) manufactured using a conventional process. Preferably the static charge of the product is selected from the group consisting of: less than 10 nC/g, less than 5 nC/g, less than 3 nC/g, less than 2 nC/g, less than 1.5 nC/g, less than 1.25 nC/g, less than 1 nC/g less than 0.75 nC/g, less than 0.5 nC/g, less than 0.25 nC/g or less than 0.1 nC/g. Preferably, the blend made using this invention has a lower cohesiveness profile compared to the cohesiveness profile of a blend (containing biologically active material of the same, similar or larger particle size) manufactured using a conventional process. Preferably the specific energy (were a lower value indicates less cohesiveness), as measured by powder rheology, of the product is selected from the group consisting of: less than 12 mJ/g, less than 10 mJ/g, less than 9 mJ/g, less than 8 mJ/g, less than 7 mJ/g, less than 6 mJ/g, less than 5 mJ/g less than 4 mJ/g or less than 3 mJ/g. Preferably, the blend made using this invention has a lower propensity for aggregation compared to the propensity for aggregation of a blend (containing biologically active material of the same, similar or larger particle size) manufactured using a conventional process. Preferably, the blend made using this invention has a lower propensity for adherence to other materials such as but not limited to stainless steel, glass, plastic, polyethylene and polypropylene compared to the propensity for adherence of a blend (containing biologically active material of the same, similar or larger particle size) manufactured using a conventional process.

Preferably, the blend made using this invention has increased uniformity compared to a blend (containing biologically active material of the same, similar or larger particle size) manufactured using a conventional process. Preferably the biological active material maintains its superior uniformity despite numerous process steps and modifications to the material. Preferably, the biological active material maintains its superior uniformity despite some level of segregation. For example, even if the biological material particles of varying size segregate, a uniform amount of active is maintained in the particles. Preferably the content uniformity of the biologically active material throughout the blend (even after segregation) varies from the average content by a percentage less than or equal to a percentage selected from the group consisting of: 0.1%, 0.2%, 0.3%, 0.4%, 0.5% 0.75%, 1.0%, 1.5%, 2.0%, 3.0%, 4.0% and 5.0%.

Preferably, the blend made using this invention has reduced levels of dust compared to a blend (containing biologically active material of the same, similar or larger particle size) manufactured using a conventional process. Preferably, the blend made using this invention has improved rheology compared to a blend (containing biologically active material of the same, similar or larger particle size) manufactured using a conventional process.

Preferably the sheer Stress of the product is selected from the group: less than 3 kPa, less than 2.75 kPa, less than 2.5 kPa, less than 2.35 kPa, less than 2.25 kPa, less than 2.1 kPa, less than 2.0 kPa, less than 1.85 kPa, less than 1.75 kPa, less than 1.50 kPa, less than 1.25 kPa or less than 1.0 kPa. Preferably the basic flow energy of the product is selected from the group: less than 500 mJ, less than 450 mJ, less than 400 mJ, less than 375 mJ, less than 350 mJ, less than 325 mJ, less than 300 mJ, or less than 250. Preferably, the blend made using this invention has reduced segregation compared to a blend (containing biologically active material of the same, similar or larger particle size) manufactured using a conventional process. Preferably, the blend made using this invention has increased bulk density or tapped bulk density compared to a blend (containing biologically active material of the same, similar or larger particle size) manufactured using a conventional process. Preferably the bulk density of the blend is selected from the group: greater than 0.3 g/ml, greater than 0.4 g/ml, greater than 0.45 g/ml, greater than 0.5 g/ml, greater than 0.55 g/ml, greater than 0.60 g/ml, greater than 0.65 g/ml, greater than 0.7 g/ml, greater than 0.75 g/ml, greater than 0.80 g/ml, greater than 0.85 g/ml. greater than 0.90 g/ml or greater than 1.0 g/ml. Preferably the tapped bulk density of the blend is selected from the group: greater than 0.3 g/ml, greater than 0.4 g/ml, greater than 0.45 g/ml, greater than 0.5 g/ml, greater than 0.55 g/ml, greater than 0.60 g/ml, greater than 0.65 g/ml, greater than 0.7 g/ml, greater than 0.75 g/ml, greater than 0.80 g/ml, greater than 0.85 g/ml. greater than 0.90 g/ml or greater than 1.0 g/ml. Preferably, the blend made using this invention has superior powder flow as defined by the Hausner ratio or Carr's index compared to a blend (containing biologically active material of the same, similar or larger particle size) manufactured using a conventional process. Preferably, the blend made using this invention has lower compressibility compared to a blend (containing biologically active material of the same, similar or larger particle size) manufactured using a conventional process. Preferably the % compressibility, as measured using a powder rheometer is less than the % selected for the group: 30, 25, 20, 17, 15, 13 and 10. Preferably, the blend made using this invention has increased permeability compared to a blend (containing biologically active material of the same, similar or larger particle size) manufactured using a conventional process. Preferably the the pressure drop (where a low pressure drop indicates superior permeability), as measured as the pressure drop across a bed of powder in a powder rheometer is selected for the group: less than 20 mBar, less than 15 mBar, less than 10 mBar, less than 7 mBar, less than 5 mBar, less than 4 mBar or less than 3 mBar. Preferably, the blend made using this invention has a higher minimum ignition energy compared to a blend (containing biologically active material of the same, similar or larger particle size) manufactured using a conventional process. Preferably, the blend made using this invention has higher hopper flow rates compared to a blend (containing biologically active material of the same, similar or larger particle size) manufactured using a conventional process. Preferably, the blend made using this invention has smaller critical orifice diameter compared to a blend (containing biologically active material of the same, similar or larger particle size) manufactured using a conventional process. Preferably, the blend made using this invention has smaller angle of repose compared to a blend (containing biologically active material of the same, similar or larger particle size) manufactured using a conventional process. Preferably, the blend made using this invention has smaller dynamic angle of repose compared to a blend (containing biologically active material of the same, similar or larger particle size) manufactured using a conventional process.

For example, the process improves powder handling characteristics relative to conventional powders of the same, similar or larger particle size when the biologically active material is manufactured, processed and formulated and finally stored in a capsule. The material is more easily poured into a capsule from a dispensing device. The material has improved flow properties so that it flows smoothly into the capsule and does not aggregate significantly when it pores, nor does it adhere significantly to any handling apparatuses or containers, and thus does not result in a significant loss of product. It's static parameters have improved such that the material does not adhere to the dispensing device or containers. The powder handling characteristics have improved such that it can be efficiently manufactured, processed and stored without significant loss of material from poor product flow, high aggregation, high adherence and high static properties. The powder handling characteristics have improved such that it can be manufactured to meet assay and content uniformity requirements as set out in the USP. The material has improved powder handling characteristics when dry. The material has improved powder handling characteristics when combined with extra functional excipients. For example the material has improved powder handling characteristics when combined with disintegrants, binders, wetting agents, fillers, disintegrants, binders, wetting agents and the like such that there are no issues with segregation or uniformity of the active through the blended material. The powder handling characteristics have improved such that it can be easily processed through standard processing equipment such as a roller compactor (dry granulator) or a wet granulator.

Particle Size

There are a wide range of techniques that can be utilized to characterize the particle size of a material. Those skilled in the art also understand that almost all these techniques do not physically measure the actually particle size, as one might measure something with a ruler, but measure a physical phenomena which is interpreted to indicate a particle size. As part of the interpretation process some assumptions need to be made to enable mathematical calculations to be made. These assumptions deliver results such as an equivalent spherical particle size, or a hydrodynamic radius.

Amongst these various methods, two types of measurements are most commonly used. Photon correlation spectroscopy (PCS), also known as 'dynamic light scattering' (DLS) is commonly used to measure particles with a size less than 10 micron. Typically this measurement yields an equivalent hydrodynamic radius often expressed as the average size of a number distribution. The other common particle size measurement is laser diffraction which is commonly used to measure particle size from 100 nm to 2000 micron. This technique calculates a volume distribution of equivalent spherical particles that can be expressed using descriptors such as the median particle size or the % of particles under a given size.

Those skilled in the art recognize that different characterization techniques such as photon correlation spectroscopy and laser diffraction measure different properties of a particle ensemble. As a result multiple techniques will give multiple answers to the question, "what is the particle size." In theory one could convert and compare the various parameters each technique measures, however, for real world particle systems this is not practical. As a result the particle size used to describe this invention will be given as two different sets of values that each relate to these two common measurement techniques, such that measurements could be made with either technique and then evaluated against the description of this invention.

For measurements made using a photo correlation spectroscopy instrument, or an equivalent method known in the art, the term "number average particle size" is defined as the average particle diameter as determined on a number basis.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50) or D[0.5] or similar. As used herein D50, D(0.50) or D[0.5] or similar shall be taken to mean 'median particle size'.

The term "Dx of the particle size distribution" refers to the xth percentile of the distribution; thus, D90 refers to the $90^{th}$ percentile, D95 refers to the $95^{th}$ percentile, and so forth. Taking D90 as an example this can often be written as, D(0.90) or D[0.9] or similar. With respect to the median particle size and Dx an upper case D or lowercase d are interchangeable and have the same meaning. Another way to quantitate a particle size distribution is the volume weighted mean (D4,3). D4,3 is defined as sum of the diameters to the power 4 divided by the sum of the diameters cubed.

Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

The particle size used to describe this invention should be taken to mean the particle size as measured at or shortly before the time of use. For example, the particle size is measured 2 months after the material is subject to the milling method of this invention. In a preferred form, the particle size is measured at a time selected from the group consisting of: 1 day after milling, 2 days after milling, 5 days after milling, 1 month after milling, 2 months after milling, 3 months after milling, 4 months after milling, 5 months after milling, 6 months after milling, 1 year after milling, 2 years after milling, 5 years after milling.

For many of the materials subject to the methods of this invention the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as PCS or laser diffraction.

Suitable methods to measure an accurate particle size where the active material has substantive aqueous solubility or the matrix has low solubility in a water based dispersant are outlined below.

1. In the circumstance where insoluble matrix such as microcrystalline cellulose prevents the measurement of the active material separation techniques such as filtration or centrifugation could be used to separate the insoluble matrix from the active material particles. Other ancillary techniques would also be required to determine if any active material was removed by the separation technique so that this could be taken into account.

2. In the case where the active material is too soluble in water other solvents could be evaluated for the measurement of particle size. Where a solvent could be found that active material is poorly soluble in but is a good solvent for the matrix a measurement would be relatively straight forward. If such a solvent is difficult to find another approach would be to measure the ensemble of matrix and active material in a solvent (such as iso-octane) which both are insoluble in. Then the powder would be measured in another solvent where the active material is soluble but the matrix is not. Thus with a measurement of the matrix particle size and a measurement of the size of the matrix and active material together an understanding of the active material particle size can be obtained.

3. In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, raman spectroscopy, FTIR spectroscopy or fluorescence spectroscopy.

Other Definitions

Throughout this specification, unless the context requires otherwise, the phrase "dry mill" or variations, such as "dry milling", should be understood to refer to milling in at least the substantial absence of liquids. If liquids are present, they are present in such amounts that the contents of the mill retain the characteristics of a dry powder.

"Flowable" means a powder having physical characteristics rendering it suitable for further processing using typical equipment used for the manufacture of pharmaceutical compositions and formulations.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The term "millable" means that the grinding matrix is capable of being physically degraded under the dry milling conditions of the method of the invention. In one embodiment of the invention, the milled grinding matrix is of a comparable particle size to the biologically active material. In another embodiment of the invention the particle size of the matrix is substantially reduced but not as small as the biologically active material Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Specific

In one embodiment, the present invention is directed to a method for producing a composition, comprising the steps of: dry milling a solid biologically active material and a millable grinding matrix in a mill comprising a plurality of milling bodies, for a time period sufficient to produce particles of the biologically active material dispersed in an at least partially milled grinding material.

The mixture of active material and matrix may then be separated from the milling bodies and removed from the mill.

In one aspect the mixture of active material and matrix is then further processed. In another aspect, the grinding matrix is separated from the particles of biologically active material. In a further aspect, at least a portion of the milled grinding matrix is separated from the particulate biologically active material.

The milling bodies are essentially resistant to fracture and erosion in the dry milling process. The quantity of the grinding matrix relative to the quantity of biologically active material in particulate form, and the extent of milling of the grinding matrix, is sufficient to inhibit re-agglomeration of the particles of the active material.

The present invention also relates to biologically active materials produced by said methods, to medicaments produced using said biologically active materials and to methods of treatment of an animal, including man, using a therapeutically effective amount of said biologically active materials administered by way of said medicaments.

Commercial Scale

The present invention is directed to the unexpected finding that particles of a biologically active material can be produced by dry milling processes as described herein at commercial scale. In one surprising aspect the particle size of the biologically active material produced by the process is equal to or less than 20,000 nm. In another surprising aspect the particle size of the biologically active material produced by the process is equal to or less than 10,000 nm. In another surprising aspect the particle size of the biologically active material produced by the process is equal to or less than 5,000 nm. In another surprising aspect the particle size of the biologically active material produced by the process is equal to or less than 2000 nm. In another surprising aspect the particle size of the biologically active material produced by the process is equal to or less than 1000 nm. This can result in a more efficient and cost effective process.

One of the key goals of reducing manufacturing costs is the encapsulation of the nanoparticles into materials that do not have to be removed. This enables a simple manufacturing process where conventional formulation technologies can be used to progress the matrix encapsulated nanoparticles directly to a final product. In order to do this the materials used within the matrix must be acceptable to industry regulators. In some cases materials may be acceptable for use but only in limited quantities. Another aspect of matrix choice is functionality. Some matrices that produce superior encapsulated nanoparticles may be acceptable from a safety perspective but these materials may make manufacture of a dosage form such as tablet limited.

Improving the Dissolution Profile

The process results in the biologically active material having an improved dissolution profile. An improved dissolution profile has significant advantages including the improvement of bioavailability of the biologically active material in vivo. Preferably, the improved dissolution profile is observed in vitro. Alternatively, the improved dissolution profile is observed in vivo by the observation of an improved bioavailability profile. Standard methods for determining the dissolution profile of a material in vitro are available in the art. A suitable method to determine an improved dissolution profile in vitro may include determining the concentration of the sample material in a solution over a period of time and comparing the results from the sample material to a control sample. An observation that peak solution concentration for the sample material was achieved in less time than the control sample would indicate (assuming it is statistically significant), that the sample material has an improved dissolution profile. The measurement sample is herein defined as the mixture of biologically active material with grinding matrix and/or other additives that has been subject to the processes of the invention described here. Herein a control sample is defined as a physical mixture (not subject to the processes described in this invention) of the components in the measurement sample with the same relative proportions of active, matrix and/or additive as the measurement sample. For the purposes of the dissolution testing a prototype formulation of the measurement sample could also be used. In this case the control sample would be formulated in the same way. Standard methods for determining the improved dissolution profile of a material in vivo are available in the art. A suitable method to determine an improved dissolution profile in a human may be after delivering the dose to measure the rate of active material absorption by measuring the plasma concentration of the sample compound over a period of time and comparing the results from the sample compound to a control. An observation that peak plasma concentration for the sample compound was achieved in less time than the control would indicate (assuming it is statistically significant) that the sample compound has improved bioavailability and an improved dissolution profile. Preferably, the improved dissolution profile is observed at a relevant gastrointestinal pH, when it is observed in vitro. Preferably, the improved dissolution profile is observed at a pH which is favourable at indicating improvements in dissolution when comparing the measurement sample to the control compound. Suitable methods for quantifying the concentration of a compound in an in vitro sample or an in vivo sample are widely available in the art. Suitable methods could include the use of spectroscopy or radioisotope labeling. In one preferred embodiment the method of quantification of dissolution is determined in a solution with a pH selected from the group consisting of: pH 1, pH 2, pH 3, pH 4, pH 5, pH 6, pH 7, pH 7.3, pH 7.4, pH 8, pH 9, pH 10, pH 11, pH 12, pH 13, pH 14 or a pH with 0.5 of a pH unit of any of this group.

Crystallization Profile

Methods for determining the crystallinity profile of the biologically active material are widely available in the art. Suitable methods may include X-ray diffraction, differential scanning calorimetry, raman or IR spectroscopy.

Amorphicity Profile

Methods for determining the amorphous content of the biologically active material are widely available in the art. Suitable methods may include X-ray diffraction, differential scanning calorimetry, raman or IR spectroscopy.

Grinding Matrix

As will be described subsequently, selection of an appropriate grinding matrix affords particular advantageous applications of the method of the present invention.

A highly advantageous application of the method of the invention is the use of a water-soluble grinding matrix in conjunction with a poorly water-soluble biologically active material. This affords at least two advantages. The first being when the powder containing the biologically active material is placed into water—such as the ingestion of the powder as part of an oral medication—the matrix dissolves, releasing the particulate active material such that there is maximum surface area exposed to solution, thereby allowing a rapid dissolution of the active compound. The second key advantage is the ability, if required, to remove or partially remove the matrix prior to further processing or formulation.

Another advantageous application of the method of the invention is the use of a water-insoluble grinding matrix, particularly in the area of agricultural use, when a biologically active material such as a fungicide is commonly delivered as part of a dry powder or a suspension. The presence of a water insoluble matrix will afford benefits such as increased rain fastness.

Without wishing to be bound by theory, it is believed that the physical degradation (including but not limited to particle size reduction) of the millable grinding matrix affords the advantage of the invention, by acting as a more effective diluent than grinding matrix of a larger particle size. Again, as will be described subsequently, a highly advantageous aspect of the present invention is that certain grinding matrixes appropriate for use in the method of the invention are also appropriate for use in a medicament. The present invention encompasses methods for the production of a medicament incorporating both the biologically active material and the grinding matrix or in some cases the biologically active material and a portion of the grinding matrix, medicaments so produced, and methods of treatment of an animal, including man, using a therapeutically effective amount of said biologically active materials by way of said medicaments.

Analogously, as will be described subsequently, a highly advantageous aspect of the present invention is that certain grinding matrixes appropriate for use in the method of the invention are also appropriate for use in a carrier for an agricultural chemical, such as a pesticide, fungicide, or herbicide. The present invention encompasses methods for the production of an agricultural chemical composition incorporating both the biologically active material in particulate form and the grinding matrix, or in some cases the biologically active material, and a portion of the grinding matrix, and agricultural chemical compositions so produced. The medicament may include only the biologically active material together with the milled grinding matrix or, more preferably, the biologically active material and milled grinding matrix may be combined with one or more pharmaceutically acceptable carriers, as well as any desired excipients or other like agents commonly used in the preparation of medicaments.

Analogously, the agricultural chemical composition may include only the biologically active material together with the milled grinding matrix or, more preferably, the biologically active materials and milled grinding matrix may be combined with one or more carriers, as well as any desired excipients or other like agents commonly used in the preparation of agricultural chemical compositions.

In one particular form of the invention, the grinding matrix is both appropriate for use in a medicament and readily separable from the biologically active material by methods not dependent on particle size. Such grinding matrixes are described in the following detailed description of the invention. Such grinding matrixes are highly advantageous in that they afford significant flexibility in the extent to which the grinding matrix may be incorporated with the biologically active material into a medicament.

In a highly preferred form, the grinding matrix is harder than the biologically active material, and is thus capable of reducing the particle size of the active material under the dry milling conditions of the invention. Again without wishing to be bound by theory, under these circumstances it is believed that the millable grinding matrix affords the advantage of the present invention through a second route, with the smaller particles of grinding matrix produced under the dry milling conditions enabling greater interaction with the biologically active material. The quantity of the grinding matrix relative to the quantity of biologically active material, and the extent of physical degradation of the grinding matrix, is sufficient to inhibit re-agglomeration of the particles of the active material Preferably, the quantity of the grinding matrix relative to the quantity of biologically active material, and the extent of physical degradation of the grinding matrix, is sufficient to inhibit re-agglomeration of the particles of the active material in nanoparticulate form. The grinding matrix is not generally selected to be chemically reactive with the biologically active material under the milling conditions of the invention, excepting for example, where the matrix is deliberately chosen to undergo a mechanico-chemical reaction. Such a reaction might be the conversion of a free base or acid to a salt or vice versa.

As stated above, the method of the present invention requires the grinding matrix to be milled with the biologically active material; that is, the grinding matrix will physically degrade under the dry milling conditions of the invention to facilitate the formation and retention of particulates of the biologically active material with reduced particle size. The precise extent of degradation required will depend on certain properties of the grinding matrix and the biologically active material, the ratio of biologically active material to grinding matrix, and the particle size distribution of the particles comprising the biologically active material.

The physical properties of the grinding matrix necessary to achieve the requisite degradation are dependent on the precise milling conditions. For example, a harder grinding matrix may degrade to a sufficient extent provided it is subjected to more vigorous dry milling conditions.

Physical properties of the grinding matrix relevant to the extent that the agent will degrade under dry milling conditions include hardness, friability, as measured by indicia such as hardness, fracture toughness and brittleness index.

A low hardness (typically a Mohs Hardness less than 7) of the biologically active material is desirable to ensure fracture of the particles during processing, so that composite microstructures develop during milling. Preferably, the hardness is less than 3 as determined using the Mohs Hardness scale.

Preferably, the grinding matrix is of low abrasivity. Low abrasivity is desirable to minimise contamination of the mixture of the biologically active material in the grinding matrix by the milling bodies and/or the milling chamber of the media mill. An indirect indication of the abrasivity can be obtained by measuring the level of milling-based contaminants.

Preferably, the grinding matrix has a low tendency to agglomerate during dry milling. While it is difficult to objectively quantify the tendency to agglomerate during milling, it is possible to obtain a subjective measure by observing the level of "caking" of the grinding matrix on the milling bodies and the milling chamber of the media mill as dry milling progresses.

The grinding matrix may be an inorganic or organic substance.

In one embodiment, the grinding matrix is selected from the following, either as a single substance or a combination of two or more substances: Polyols (sugar alcohols) for example (but not limited to) mannitol, sorbitol, isomalt, xylitol, maltitol, lactitol, erythritol, arabitol, ribitol, monosaccharides for example (but not limited to) glucose, fructose, mannose, galactose, disaccharides and trisaccharides for example (but not limited to) anhydrous lactose, lactose monohydrate, sucrose, maltose, trehalose, polysaccharides for example (but not limited to) maltodextrins, dextrin, Inulin, dextrates, polydextrose, other carbohyrates for example (but not limited to) starch, wheat flour, corn flour, rice flour, rice starch, tapioca flour, tapioca starch, potato flour, potato starch, other flours and starches, soy flour, soy meal or other soy products, cellulose, microcrystalline cellulose, microcrystalline cellulose based co blended excipients, chemically modified excipients such as pregelatinized (or partially) starch, modified celluloses such as HPMC, CMC, HPC, enteric polymer coatings such as hypromellose phthalate, cellulose acetate phthalate (Aquacoat®), polyvinyl acetate phthalate (Sureteric®), hypromellose acetate succinate (AQOAT®), and polmethacrylates (Eudragit® and Acryl-EZE®), Milk products for example (but not limited to) milk powder, skim milk powders, other milk solids and dreviatives, other functional Excipients, organic acids for example (but not limited to) citric acid, tartaric acid, malic acid, maleic acid fumaric acid, ascorbic acid, succinic acid, the conjugate salt of organic acids for example (but not limited to) sodium citrate, sodium tartrate, sodium malate, sodium ascorbate, potassium citrate, potassium tartrate, potassium malate, potassium ascorbate, inorganics such as sodium carbonate, potassium carbonate, magnesium carbonate, sodium bicarbonate, potassium bicarbonate and calcium carbonate. dibasic calcium phosphate, tribasic calcium phosphate, sodium sulfate, sodium chloride, sodium metabisulphite, sodium thiosulfate, ammonium chloride, Glauber's salt, ammonium carbonate, sodium bisulfate, magnesium sulfate, potash alum, potassium chloride, sodium hydrogen sulfate, sodium hydroxide, crystalline hydroxides, hydrogen carbonates, hydrogen carbonates of pharmaceutical acceptable alkali metals, such as but not limited by, sodium, potassium, lithium, calcium, and barium, ammonium salts (or salts of volatile amines), for example (but not limited to) ammonium chloride, methylamine hydrochloride, ammonium bromide, other inorganics for example (but not limited to), thermal silica, chalk, mica, silica, alumina, titanium dioxide, talc, kaolin, bentonite, hectorite, magnesium trisilicate, other clay or clay derivatives or aluminium silicates, a surfactant for example (but not limited to) sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 407, poloxamer 338, polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Sodium Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

In a preferred embodiment, the grinding matrix is a matrix that is considered GRAS (generally regarded as safe) by persons skilled in the pharmaceutical arts.

In another preferred aspect a combination of two or more suitable matrices, such as those listed above, can be used as the grinding matrix to provide improved properties such as the reduction of caking, and greater improvement of the dissolution profile. Combination matrices may also be advantageous when the matrices have different solubility's allowing the removal or partial removal of one matrix, while leaving the other or part of the other to provide encapsulation or partial encapsulation of the biologically active material.

Another highly preferred aspect of the method is the inclusion of a suitable milling aid in the matrix to improve milling performance. Improvements to milling performance would be things such as, but not limited to, a reduction in caking or higher recovery of powder from the mill. Examples of suitable milling aids include surfactants, polymers and inorganics such as silica (including colloidal silica), aluminium silicates and clays.

There are a wide range of surfactants that will make suitable milling aids. The highly preferred form is where the surfactant is a solid, or can be manufactured into a solid. Preferably, the surfactant is selected from the group consisting of: polyoxyethylene alkyl ethers, polyoxyethylene stearates, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, Sorbitan fatty acid esters, Sucrose fatty acid esters, alkyl glucopyranosides, alkyl maltopyranosides, glycerol fatty acid esters, Alkyl Benzene Sulphonic Acids, Alkyl Ether Carboxylic Acids, Alkyl and aryl Phosphate esters, Alkyl and aryl Sulphate esters, Alkyl and aryl Sulphonic acids, Alkyl Phenol Phosphates esters, Alkyl Phenol Sulphates esters, Alkyl and Aryl Phosphates, Alkyl Polysaccharides, Alkylamine Ethoxylates, Alkyl-Naphthalene Sulphonates formaldehyde condensates, Sulfosuccinates, lignosulfonates, Ceto-Oleyl Alcohol Ethoxylates, Condensed Naphthalene Sulphonates, Dialkyl and Alkyl Naphthalene Sulphonates, Di-alkyl Sulphosuccinates, Ethoxylated nonylphenols, Ethylene Glycol Esters, Fatty Alcohol Alkoxylates, Hydrogenated tallowalkylamines, Mono-alkyl Sulphosuccinamates, Nonyl Phenol Ethoxylates, Sodium Oleyl N-methyl Taurate, Tallowalkylamines, linear and branched dodecylbenzene sulfonic acids Preferably, the surfactant is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Sodium Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

Preferably the polymer is selected from the list of: polyvinylpyrrolidones (PVP), polyvinylalcohol, Acrylic acid based polymers and copolymers of acrylic acid Preferably, the milling aid has a concentration selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

Milling Bodies

In the method of the present invention, the milling bodies are preferably chemically inert and rigid. The term "chemically-inert", as used herein, means that the milling bodies do not react chemically with the biologically active material or the grinding matrix.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. Preferably, the milling bodies are provided in the form of one or more of beads, balls, spheres, rods, right cylinders, drums or radius-end right cylinders (i.e., right cylinders having hemispherical bases with the same radius as the cylinder).

Depending on the nature of the biologically active material and the grinding matrix, the milling media bodies desirably have an effective mean particle diameter (i.e. "particle size") between about 0.1 and 30 mm, more preferably between about 1 and about 15 mm, still more preferably between about 3 and 10 mm.

The milling bodies may comprise various substances such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 316 or 440C stainless steel or type 1065 high carbon steel.

Preferred ceramics, for example, can be selected from a wide array of ceramics desirably having sufficient hardness and resistance to fracture to enable them to avoid being chipped or crushed during milling and also having sufficiently high density. Suitable densities for milling media can range from about 1 to 15 g/cm$^3$, preferably from about 1 to 8 g/cm$^3$. Preferred ceramics can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Preferred glass milling media are spherical (e.g. beads), have a narrow size distribution, are durable, and include, for example, lead-free soda lime glass and borosilicate glass. Polymeric milling media are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Preferred polymeric resins, for example, can be selected from crosslinked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling media to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are preferred. Alternatively, the milling media can be composite particles comprising dense core particles having a polymeric resin adhered thereon. Core particles can be selected from substances known to be useful as milling media, for example, glass, alumina, zirconia silica, zirconium oxide, stainless steel, and the like. Preferred core substances have densities greater than about 2.5 g/cm$^3$.

In one embodiment of the invention, the milling media are formed from a ferromagnetic substance, thereby facilitating removal of contaminants arising from wear of the milling media by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other media and significantly more milling time is required. Finally, ceramics are advantageous from the standpoint of low wear and contamination, ease of cleaning, and high hardness.

Dry Milling

In the dry milling process of the present invention, the biologically active material and grinding matrix, in the form of crystals, powders, or the like, are combined in suitable proportions with the plurality of milling bodies in a milling chamber that is mechanically agitated (i.e. with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies can result in application of shearing forces as well as multiple impacts or collisions having significant intensity between milling bodies and particles of the biologically active material and grinding matrix. The nature and intensity of the forces applied by the milling bodies to the biologically active material and the grinding matrix is influenced by a wide variety of processing parameters including: the type of milling apparatus; the intensity of the forces generated, the kinematic aspects of the process; the size, density, shape, and composition of the milling bodies; the weight ratio of the biologically active material and grinding matrix mixture to the milling bodies; the duration of milling; the physical properties of both the biologically active material and the grinding matrix; the atmosphere present during activation; and others.

Advantageously, the media mill is capable of repeatedly or continuously applying mechanical compressive forces and shear stress to the biologically active material and the grinding matrix. Suitable media mills include but are not limited to the following: high-energy ball, sand, bead or pearl mills, basket mill, planetary mill, vibratory action ball mill, multi-axial shaker/mixer, stirred ball mill, horizontal small media mill, multi-ring pulverizing mill, and the like, including small milling media. The milling apparatus also can contain one or more rotating shafts.

In a preferred form of the invention, the dry milling is performed in a ball mill. Throughout the remainder of the specification reference will be made to dry milling being carried out by way of a ball mill. Examples of this type of mill are attritor mills, nutating mills, tower mills, planetary mills, vibratory mills and gravity-dependent-type ball mills. It will be appreciated that dry milling in accordance with the method of the invention may also be achieved by any suitable means other than ball milling. For example, dry milling may also be achieved using jet mills, rod mills, roller mills or crusher mills.

Biologically Active Material

The biologically active material includes active compounds, including compounds for veterinary and human use such as but not limited to, pharmaceutical actives, nutraceuticals, cosmeceuticals, cosmetics, complementary medicines, natural products, vitamins, nutrients, biologics, amino acids, proteins, peptides, nucleotides, nucleic acids. and agricultural compounds such as pesticides, herbicides and fungicides, germinating agents and the like. Other biologically active materials include, but are not limited to, foods, seeds, cocoa, cocoa powder, cocoa nibs, cocoa mass, cocoa liquor, cocoa solids, coffee, herbs, spices, other plant materials, minerals, animal products, shells and other skeletal material.

In a preferred form of the invention, the biologically active material is an organic compound. In a highly preferred form of the invention, the biologically active material is an organic, therapeutically active compound for veterinary or human use.

In a preferred form of the invention, the biologically active material is an inorganic compound. In a highly preferred form of the invention, the biologically active material is sulphur, copper hydroxide, an organometallic complex or copper oxychloride.

The biologically active material is ordinarily a material for which one of skill in the art desires improved dissolution properties. The biologically active material may be a conventional active agent or drug, although the process of the invention may be employed on formulations or agents that already have reduced particle size compared to their conventional form.

Biologically active materials suitable for use in the invention include actives, biologics, amino acids, proteins, peptides, nucleotides, nucleic acids, and analogs, homologs and first order derivatives thereof. The biologically active material can be selected from a variety of known classes of drugs, including, but not limited to: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-Parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's The Extra Pharmacopoeia, 31st Edition (The Pharmaceutical Press, London, 1996), specifically incorporated by reference. Another source of active agents is the Physicians Desk Reference (60$^{th}$ Ed., pub. 2005), familiar to those of skill in the art. The active agents are commercially available and/or can be prepared by techniques known in the art.

An exhaustive list of drugs for which the methods of the invention are suitable would be burdensomely long for this specification; however, reference to the general pharmacopoeia listed above would allow one of skill in the art to select virtually any drug to which the method of the invention may be applied.

In addition it is also expected that new chemical entities (NCE) and other actives for which the methods of the invention are suitable will be created or become commercially available in the future.

Notwithstanding the general applicability of the method of the invention, more specific examples of biologically active materials include, but are not limited to: haloperidol (dopamine antagonist), DL isoproterenol hydrochloride (β-adrenergic agonist), terfenadine (H1-antagonist), propranolol hydrochloride (β-adrenergic antagonist), desipramine hydrochloride (antidepressant), sildenafil citrate, tadalafil and vardenafil. Minor analgesics (cyclooxygenase inhibitors), fenamic acids, Piroxicam, Cox-2 inhibitors, and Naproxen, and others, may all benefit from being prepared.

As discussed in the context of the background to the invention, biologically active materials that are poorly water soluble at gastrointestinal pH will particularly benefit from being prepared, and the method of the present invention is particularly advantageously applied to materials that are poorly water soluble at gastrointestinal pH.

Such materials include, but are not limited to: albendazole, albendazole sulfoxide, alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocryptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, eproprostenol, estradiol, estramustine, etofibrate, etoposide, factor ix, factor viii, felbamate, fenbendazole, fenofibrate, fexofenedine, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, *lactobacillus* vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, olanzapine, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, raloxifene, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and x-ray contrast agents. Drugs can be neutral species or basic or acidic as well as salts of an acid or base. Specifically the chemical makeup and the functional groups, including an acid or base group, are generally not the determinant factor, excepting a possible chemical reaction with a specific matrix, for the successful creation of a biologically active substance with a reduced particle size. This invention is not limited to any drug specific class, application type, chemical type or function grouping. Rather the suitability of a biologically active material for use in this invention is primarily determined by the mechanical properties of the material. In addition, some biologically active materials may have the benefit of absorption through the skin if presented in a particle formulation. Such biologically active materials include, but are not limited to, Voltaren (diclofenac), rofecoxib, and ibuprofen.

Conveniently, the biologically active material is capable of withstanding temperatures that are typical in uncooled dry milling, which may exceed 80° C. Therefore, materials with a melting point about 80° C. or greater are highly suitable. For biologically active materials with lower melting points, the media mill may be cooled, thereby allowing materials with significantly lower melting temperatures to be processed according to the method of the invention. For instance, a simple water-cooled mill will keep temperatures below 50° C., or chilled water could be used to further lower the milling temperature. Those skilled in the art will understand that a high energy ball mill could be designed to run at any temperature between say −30 to 200° C. For some biologically active materials it may be advantageous to control the milling temperature to temperatures significantly below the melting points of the biologically active materials.

The biologically active material is obtained in a conventional form commercially and/or prepared by techniques known in the art.

It is preferred, but not essential, that the particle size of the biologically active material be less than about 1000 μm, as determined by sieve analysis. If the coarse particle size of the biologically active material is greater than about 1000 μm, then it is preferred that the particles of the biologically active material substrate be reduced in size to less than 1000 μm using another standard milling method.

Processed Biologically Active Material

Preferably, the biologically active materials, which have been subject to the methods of the invention, comprises particles of biologically active material of an average particle size, determined on a particle number basis, is equal to or less than a size selected from the group 10,000 nm, 5000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm.

Preferably, the biologically active materials, which have been subject to the methods of the invention, comprises particles of biologically active material of a median particle size, determined on a particle volume basis, equal or less than a size selected from the group 20,000 nm, 15,000 nm, 10,000 nm, 5000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm.

These sizes refer to particles either fully dispersed or partially agglomerated.

Agglomerates of Biologically Active Material after Processing

Agglomerates comprising particles of biologically active material, said particles having a particle size within the ranges specified above, should be understood to fall within the scope of the present invention, regardless of whether the agglomerates exceed the ranges specified above. Agglomerates comprising particles of biologically active material, said agglomerates having a total agglomerate size within the ranges specified above, should be understood to fall within the scope of the present invention.

Agglomerates comprising particles of biologically active material should be understood to fall within the scope of the present invention if at the time of use, or further processing, the particle size of the agglomerate is within the ranges specified above.

Agglomerates comprising particles of biologically active material, said particles having a particle size within the ranges specified above, at the time of use, or further processing, should be understood to fall within the scope of the present invention, regardless of whether the agglomerates exceed the ranges specified above.

Processing Time

Preferably, the biologically active material and the grinding matrix are dry milled for the shortest time necessary to form the mixture of the biologically active material in the grinding matrix such that the active material has improved dissolution to minimise any possible contamination from the media mill and/or the plurality of milling bodies. This time varies greatly, depending on the biologically active material and the grinding matrix, and may range from as short as 1 minute to several hours. Dry milling times in excess of 2 hours may lead to degradation of the biologically active material and an increased level of undesirable contaminants.

Suitable rates of agitation and total milling times are adjusted for the type and size of milling apparatus as well as the milling media, the weight ratio of the biologically active material and grinding matrix mixture to the plurality of milling bodies, the chemical and physical properties of the biologically active material and grinding matrix, and other parameters that may be optimized empirically.

Inclusion of the Grinding Matrix with the Biologically Active Material and Separation of The Grinding Matrix from the Biologically Active Material In a preferred aspect, the grinding matrix is not separated from the biologically active material but is maintained with the biologically active material in the final product. Preferably the grinding matrix is considered to be Generally Regarded as Safe (GRAS) for pharmaceutical products.

In an alternative aspect, the grinding matrix is separated from the biologically active material. In one aspect, where the grinding matrix is not fully milled, the unmilled grinding matrix is separated from the biologically active material. In a further aspect, at least a portion of the milled grinding matrix is separated from the biologically active material.

Any portion of the grinding matrix may be removed, including but not limited to 10%, 25%, 50%, 75%, or substantially all of the grinding matrix.

In some embodiments of the invention, a significant portion of the milled grinding matrix may comprise particles of a size similar to and/or smaller than the particles comprising the biologically active material. Where the portion of the milled grinding matrix to be separated from the particles comprising the biologically active material comprises particles of a size similar to and/or smaller than the particles comprising the biologically active material, separation techniques based on size distribution are inapplicable.

In these circumstances, the method of the present invention may involve separation of at least a portion of the milled grinding matrix from the biologically active material by techniques including but not limited to electrostatic separation, magnetic separation, centrifugation (density separation), hydrodynamic separation, froth flotation.

Advantageously, the step of removing at least a portion of the milled grinding matrix from the biologically active material may be performed through means such as selective dissolution, washing, or sublimation.

An advantageous aspect of the invention would be the use of grinding matrix that has two or more components where at least one component is water soluble and at least one component has low solubility in water. In this case washing can be used to remove the matrix component soluble in water leaving the biologically active material encapsulated in the remaining matrix components. In a highly advantageous aspect of the invention the matrix with low solubility is a functional excipient.

A highly advantageous aspect of the present invention is that certain grinding matrixes appropriate for use in the method of the invention (in that they physically degrade to the desired extent under dry milling conditions) are also pharmaceutically acceptable and thus appropriate for use in a medicament. Where the method of the present invention does not involve complete separation of the grinding matrix from the biologically active material, the present invention encompasses methods for the production of a medicament incorporating both the biologically active material and at least a portion of the milled grinding matrix, medicaments so produced and methods of treatment of an animal, including man, using a therapeutically effective amount of said biologically active materials by way of said medicaments.

The medicament may include only the biologically active material and the grinding matrix or, more preferably, the biologically active materials and grinding matrix may be combined with one or more pharmaceutically acceptable carriers, as well as any desired excipients or other like agents commonly used in the preparation of medicaments.

Analogously, a highly advantageous aspect of the present invention is that certain grinding matrixes appropriate for use in the method of the invention (in that they physically degrade to a desirable extent under dry milling conditions) are also appropriate for use in an agricultural chemical composition. Where the method of the present invention does not involve complete separation of the grinding matrix from the biologically active material, the present invention encompasses methods for the production of a agricultural chemical composition incorporating both the biologically active material and at least a portion of the milled grinding matrix, agricultural chemical composition so produced and methods of use of such compositions.

The agricultural chemical composition may include only the biologically active material and the grinding matrix or, more preferably, the biologically active materials and grinding matrix may be combined with one or more acceptable carriers, as well as any desired excipients or other like agents commonly used in the preparation of agricultural chemical compositions.

In one particular form of the invention, the grinding matrix is both appropriate for use in a medicament and readily separable from the biologically active material by methods not dependent on particle size. Such grinding matrixes are described in the following detailed description of the invention. Such grinding matrixes are highly advantageous in that they afford significant flexibility in the extent to which the grinding matrix may be incorporated with the biologically active material into a medicament.

The mixture of biologically active material and grinding matrix may then be separated from the milling bodies and removed from the mill.

In one embodiment, the grinding matrix is separated from the mixture of biologically active material and grinding matrix. Where the grinding matrix is not fully milled, the unmilled grinding matrix is separated from the biologically active material. In a further aspect, at least a portion of the milled grinding matrix is separated from the biologically active material.

The milling bodies are essentially resistant to fracture and erosion in the dry milling process.

The quantity of the grinding matrix relative to the quantity of biologically active material, and the extent of milling of the grinding matrix, is sufficient to provide reduced particle size of the biologically active material.

The grinding matrix is neither chemically nor mechanically reactive with the pharmaceutical material under the dry milling conditions of the method of the invention except, for example, where the matrix is deliberately chosen to undergo a mechanico-chemical reaction. Such a reaction might be the conversion of a free base or acid to a salt or vice versa.

Preferably, the medicament is a solid dosage form, however, other dosage forms may be prepared by those of ordinary skill in the art.

In one form, after the step of separating said mixture of biologically active material and grinding matrix from the plurality of milling bodies, and before the step of using said mixture of biologically active material and grinding matrix in the manufacture of a medicament, the method may comprise the step of:

removing a portion of the grinding matrix from said mixture of biologically active material and grinding matrix to provide a mixture enriched in the biologically active material;

and the step of using said mixture of biologically active material and grinding matrix in the manufacture of a medicament, more particularly comprises the step of using the mixture of biologically active material and grinding matrix enriched in the biologically active material form in the manufacture of a medicament.

The present invention includes medicaments manufactured by said methods, and methods for the treatment of an animal, including man, by the administration of a therapeutically effective amount of the biologically active materials by way of said medicaments.

In another embodiment of the invention, a facilitating agent or a combination of facilitating agents is also comprised in the mixture to be milled. Such facilitating agents appropriate for use in the invention include diluents, surfactants, polymers, binding agents, filling agents, lubricating agents, sweeteners, flavouring agents, preservatives, buffers, wetting agents, disintegrants, effervescent agents and agents that may form part of a medicament, including a solid dosage form, or other excipients required for other specific drug delivery, such as the agents and media listed below under the heading Medicinal and Pharmaceutical Compositions, or any combination thereof.

Biologically Active Materials and Compositions

The present invention encompasses pharmaceutically acceptable materials produced according to the methods of the present invention, compositions including such materials, including compositions comprising such materials together with the grinding matrix with or without milling aids, facilitating agents, with at least a portion of the grinding matrix or separated from the grinding matrix.

The pharmaceutically acceptable materials within the compositions of the invention are present at a concentration of between about 0.1% and about 99.0% by weight. Preferably, the concentration of pharmaceutically acceptable materials within the compositions will be about 5% to about 80% by weight, while concentrations of 10% to about 50% by weight are highly preferred. Desirably, the concentration will be in the range of about 10 to 15% by weight, 15 to 20% by weight, 20 to 25% by weight, 25 to 30% by weight, 30 to 35% by weight, 35 to 40% by weight, 40 to 45% by weight, 45 to 50% by weight, 50 to 55% by weight, 55 to 60% by weight, 60 to 65% by weight, 65 to 70% by weight, 70 to 75% by weight or 75 to 80% by weight for the composition prior to any later removal (if desired) of any portion of the grinding matrix. Where part or all of the grinding matrix has been removed, the relative concentration of pharmaceutically acceptable materials in the composition may be considerably higher depending on the amount of the grinding matrix that is removed. For example, if all of the grinding matrix is removed the concentration of particles in the preparation may approach 100% by weight (subject to the presence of facilitating agents).

Compositions produced according to the present invention are not limited to the inclusion of a single species of pharmaceutically acceptable materials. More than one species of pharmaceutically acceptable materials may therefore be present in the composition. Where more than one species of pharmaceutically acceptable materials is present, the composition so formed may either be prepared in a dry milling step, or the pharmaceutically acceptable materials may be prepared separately and then combined to form a single composition.

Medicaments

The medicaments of the present invention may include the pharmaceutically acceptable material, optionally together with the grinding matrix or at least a portion of the grinding matrix, with or without milling aids, facilitating agents, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration, intravenous, intraperitoneal, intramuscular, sublingual, pulmonary, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable material, use thereof in the manufacture of a pharmaceutical composition according to the invention is contemplated.

Pharmaceutical acceptable carriers according to the invention may include one or more of the following examples:

(1) surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate (2) binding agents such as various celluloses and crosslinked polyvinylpyrrolidone, microcrystalline cellulose; and or (3) filling agents such as lactose monohydrate, lactose anhydrous, microcrystalline cellulose and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and accsulfame K; and or (6) flavouring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quaternary compounds such as benzalkonium chloride; and or (8) buffers; and or (9) Diluents such as pharmaceutically acceptable inert fillers, such as microcrystalline cellulose, lactose, dibasic calcium phosphate, saccharides, and/or mixtures of any of the foregoing; and or

(10) wetting agents such as corn starch, potato starch, maize starch, and modified starches, croscarmellose sodium, crosspovidone, sodium starch glycolate, and mixtures thereof; and or

(11) disintegrants; and or

(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or

(13) other pharmaceutically acceptable excipients.

Medicaments of the invention suitable for use in animals and in particular in man typically must be stable under the conditions of manufacture and storage. The medicaments of the invention comprising the biologically active material can be formulated as a solid, a solution, a microemulsion, a liposome, or other ordered structures suitable to high drug concentration. Actual dosage levels of the biologically active material in the medicament of the invention may be varied in accordance with the nature of the biologically active material, as well as the potential increased efficacy due to the advantages of providing and administering the biologically active material (e.g., increased solubility, more rapid dissolution, increased surface area of the biologically active material, etc.). Thus as used herein "therapeutically effective amount" will refer to an amount of biologically active material required to effect a therapeutic response in an animal. Amounts effective for such a use will depend on: the desired therapeutic effect; the route of administration; the potency of the biologically active material; the desired duration of treatment; the stage and severity of the disease being treated; the weight and general state of health of the patient; and the judgment of the prescribing physician.

In another embodiment, the biologically active material, optionally together with the grinding matrix or at least a portion of the grinding matrix, of the invention may be combined into a medicament with another biologically active material, or even the same biologically active material. In the latter embodiment, a medicament may be achieved which provides for different release characteristics—early release from the biologically active material, and later release from a larger average size biologically active material.

Modes of Administration of Medicaments Comprising Biologically Active Materials

Medicaments of the invention can be administered to animals, including man, in any pharmaceutically acceptable manner, such as orally, rectally, pulmonary, intravaginally, locally (powders, ointments or drops), transdermal, parenteral administration, intravenous, intraperitoneal, intramuscular, sublingual or as a buccal or nasal spray Solid dosage forms for oral administration include capsules, tablets, pills, powders, pellets, and granules. Further, incorporating any of the normally employed excipients, such as those previously listed, and generally 5-95% of the biologically active agent, and more preferably at a concentration of 10%-75% will form a pharmaceutically acceptable non-toxic oral composition.

Medicaments of the invention may be parenterally administered as a solution of the biologically active agent suspended in an acceptable carrier, preferably an aqueous carrier. A variety of aqueous carriers may be used, e.g. water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

For aerosol administration, medicaments of the invention are preferably supplied along with a surfactant or polymer and propellant. The surfactant or polymer must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant or polymer may constitute 0.1%-20% by weight of the composition, preferably 0.25-5%. The balance of the composition is ordinarily propellant. A carrier can also be included, as desired, as with, e.g., lecithin for intranasal delivery.

Medicaments of the invention may also be administered via liposomes, which serve to target the active agent to a particular tissue, such as lymphoid tissue, or targeted selectively to cells. Liposomes include emulsions, foams, micelles, insoluble monolayers, liquid crystals, phospholipid dispersions, lamellar layers and the like. In these preparations the composite microstructure composition is incorporated as part of a liposome, alone or in conjunction with a molecule that binds to or with other therapeutic or immunogenic compositions.

As described above, the biologically active material can be formulated into a solid dosage form (e.g., for oral or suppository administration), together with the grinding matrix or at least a portion of it. In this case there may be little or no need to add stabilizing agents since the grinding matrix may effectively act as a solid-state stabilizer.

However, if the biologically active material is to be utilized in a liquid suspension, the particles comprising the biologically active material may require further stabilization once the solid carrier has been substantially removed to ensure the elimination, or at least minimisation of particle agglomeration.

Inhaled and Intranasal Delivery

Dry powder formulations of active pharmaceutical ingredients (including blends of active and excipients) for inhalation or nasal delivery are important tools for the delivery of medications. Common uses have been in the delivery of pharmaceutical agents that act locally. Examples of this are astma medications delivered to the lungs or decongestants delivered by an intranasal route. These delivery routes are also becoming more important for systemic delivery. Thus the pharmaceutical formulator will require more and improved techniques to manufacture formulations for these purposes.

Two of the critical parameters for inhaled or intranasal dry powder formulations are particle size and the flowability of the powder. The powder in the device used by the patient needs to flow well so that a full and consistent dose of the powder formulation leaves the device. If the powder flow is poor, powder may remain behind in the device or stick to the device as it is dispensed. The particle size of the powder is then critical to ensure that the powder (and active material) is (are) delivered to the required absorption zone.

One common measure of particle size used to characterize dry powder formulations is the Mass Median Aerodynamic Diameter (MMAD). This is defined as the aerodynamic diameter at which 50% of the particles by mass are larger and 50% are smaller. Aerodynamic particle size measurements are typically made using devices such as the Anderson Cascade Impactor or the New Generation Impactor which use a series of stages that have descending cut off diameters. Other particle size measures such as the median particle size measured by a laser diffraction dry powder analysis are also useful. However, MMAD is the preferred measurement for an inhaled formulation as it better approximates the aerodynamic properties of the lungs. For an inhaled formulation the MMAD is preferably less than 10 microns, more preferably less than 5 microns. Where dry powder sizing by laser diffraction is used, the median particle size is preferably less than 10 microns.

Powders suitable for intranasal delivery would preferably have an aerodynamic particle size equal to or greater than 10 micron. Thus where dry powder sizing by laser diffraction is used the median particle size is preferably equal to or greater than 10 microns. The area of deposition within the nasal cavity is also governed by the particle size of the powder. Generally powder that has an aerodynamic particle size greater than 20 micron will be deposited in the anterior portion of the nose where longer residence times occur. Generally powder that has an aerodynamic particle size equal to or greater than 10 micron but less than 20 microns will be deposited in the posterior portion of the nose where permeability is generally higher providing good systemic absorption.

In the aspect of this invention relating to intranasal formulations where dry powder sizing by laser diffraction is used, the median particle size is preferably equal to or greater than 10 microns. Preferably, the median particle size is equal to or greater than 10 microns and less than 20 micron for posterior delivery. Preferably, the median particle size is equal to or greater than 20 micron for anterior delivery.

Suitable methods for preparing formulations for intranasal delivery are widely known in the art. For example, WO2009/027337 (Applicant: Novartis AG, and hereby incorporated by reference), provides methods for making formulations for intranasl delivery using wet processes followed by spray drying steps. The methods described in the WO2009/027337 publication use complex recipes, equipment and multiple steps. In contrast, the invention which is the subject of this application is a simple one step dry milling process.

Therapeutic Uses

Therapeutic uses of the medicaments of the invention include pain relief, anti-inflammatory, migraine, asthma, and other disorders that require the active agent to be administered with a high bioavailability.

One of the main areas when rapid bioavailability of a biologically active material is required is in the relief of pain. The minor analgesics, such as cyclooxgenase inhibitors (aspirin related drugs) may be prepared as medicaments according to the present invention.

Medicaments of the invention may also be used for treatment of eye disorders. That is, the biologically active material may be formulated for administration on the eye as an aqueous suspension in physiological saline, or a gel. In addition, the biologically active material may be prepared in a powder form for administration via the nose for rapid central nervous system penetration.

Treatment of cardiovascular disease may also benefit from biologically active materials according to the invention, such as treatment of angina pectoris and, in particular, molsidomine may benefit from better bioavailability.

Other therapeutic uses of the medicaments of the present invention include treatment of hair loss, sexual dysfunction, or dermal treatment of psoriasis.

The present invention will now be described with reference to the following non-limiting Examples. The description of the Examples is in no way limiting on the preceding paragraphs of this specification, but is provided for exemplification of the methods and compositions of the invention.

EXAMPLES

It will be apparent to persons skilled in the milling and pharmaceutical arts that numerous enhancements and modifications can be made to the above described processes without departing from the basic inventive concepts. For example, in some applications the biologically active material may be pretreated and supplied to the process in the pretreated form. All such modifications and enhancements are considered to be within the scope of the present invention, the nature of which is to be determined from the foregoing description and the appended claims. Furthermore, the following Examples are provided for illustrative purposes only, and are not intended to limit the scope of the processes or compositions of the invention.

The Following Materials were Used in the Examples

Active pharmaceutical ingredients were sourced from commercial suppliers, excipients from either commercial suppliers such as Sigma-Aldrich or retailers, while food ingredients were sourced from retailers.

The following mills were used for the grinding experiments

Spex-Type Mill:

Small scale milling experiments were conducted using a vibratory Spex 8000D mixer/mill. Twelve ⅜" stainless steel balls were used as the grinding media. The powder charge and grinding media were loaded into a hardened steel vial with an internal volume of approximately 75 mL. Following milling, the milled material was discharged from the vial and sieved to remove grinding media.

Attritor-Type Mill:

Small scale attritor milling experiments were performed using a 1HD Union Process attritor mill with a 110 mL grinding chamber. The grinding media consisted of 330 g ⁵⁄₁₆" stainless steel balls. The mill was loaded through the loading port, with dry materials added initially, followed by the grinding media. The milling process was conducted with the jacket cooled at 10-20° C. and the shaft rotating at 500 rpm. Upon completion of milling, the milled material was discharged from the mill and sieved to remove the grinding media.

Medium scale attritor milling experiments were performed using a 1HD Union Process attritor mill with a 1 L grinding chamber or a 1S Union Process attritor mill with a 750 mL grinding chamber. The grinding media consisted of 3 kg of 5/16" stainless steel balls or 1.5 kg of 3/8" stainless steel balls for the 1S attritor. The 1HD mill was loaded through the loading port, with dry materials added initially, followed by the grinding media, while the grinding media was added initially, followed by the dry materials in the 1S attritor mill. The milling process was conducted with the jacket cooled at 10-20° C. with the shaft rotating at 350 rpm in the 1HD attritor or 550 rpm in the 1S attritor. Upon completion of milling, the milled material was discharged from the mill and sieved to remove the grinding media.

Medium to large scale attritor milling experiments were performed using a 1S Union Process attritor mill with a % gallon grinding chamber. The grinding media consisted of 7 kg of 3/8" stainless steel balls. The mill was loaded through the loading port, with the grinding media added initially, followed by the dry powders. The milling process was conducted with the jacket cooled at 18° C. and the shaft rotating at 550-555 rpm. Upon completion of milling, the milled powder was discharged from the mill through the bottom discharge port at 77 rpm for 5 min.

Large scale attritor milling experiments were performed using a 1S Union Process attritor mill with a 1½ gallon grinding chamber. The grinding media consisted of 20 kg of 3/8" stainless steel balls. The mill was loaded through the loading port, with the grinding media added initially, then followed by the dry powders. The milling process was conducted with the jacket cooled to ambient temperature and the shaft rotating at 300 rpm. Upon completion of milling, the milled powder was discharged from the mill through the bottom discharge port at 77 rpm for 5 min.

The largest scale attritor millings were done in a 30S Union Process mill with a 25 gallon grinding chamber (Union Process, Akron OH, USA). The grinding media consisted of 454 kg of 3/8" stainless steel balls. The mill was loaded through its split top lid, with the grinding media added initially, then followed by the dry powders (25 kg). The milling process was conducted with the jacket cooled to 10° C. and the shaft rotating at 130 rpm. Upon completion of milling, the milled powder was discharged from the mill through the bottom discharge port at 77 rpm for 5 min.

Siebtechnik Mill

Medium scale milling experiments were also performed in a Siebtechnik GSM06 (Siebtechnik, GmbH, Germany) with two 1 L milling chambers. Each chamber was filled with 2.7 kg stainless steel media with a diameter of 3/8". The media and powder were loaded with the lid off. The mill was operated at ambient temperature. The vibration speed was the standard mill settings. Upon completion of the milling the media was separated from the powder by sieving.

Simoloyer Mill

Medium scale milling experiments were performed in a Simoloyer CM01 (ZOZ GmbH, Germany) with a 2 L milling chamber. The grinding media consisted of 2.5 kg stainless steel 35 media with a diameter of 5 mm. the media was loaded though the loading port followed by the dry materials. The milling vessel was cooled using water at a temperature of about 18° C. The mill speed was operated in cycle mode: at 1300 rpm for two minutes and at 500 rpm for 0.5 min and so forth. Upon completion of the milling the media was discharged from the mill using a grated valve to retain the grinding media.

Large scale milling experiments were performed in a Simoloyer CM100 (ZOZ GmbH, Germany) with a 100 L milling chamber. The grinding media consisted of 100 kg stainless steel media with a diameter of 3/16". The powder charge (11 kg) was added to the milling chamber, which already contained the grinding media, through a loading port. The milling chamber was cooled to 18° C. and the powder was milled for a total of 20 minutes using a cycling mode equivalent to a tip speed at 1300/500 rpm for 2/0.5 min in the CM-01 type mill. Upon completion of the milling the mill was discharged by sucking the powder into a cyclone.

Hicom Mill

Millings performed in a nutating Hicom mill utilized 14 kg of stainless steel 0.25" grinding media together with a powder charge of 480 g. The mill was loaded by pre-mixing media and powder, then adding the mixture to the grinding chamber through the loading port at the top of the mill. The milling was done at 1000 rpm and the mill discharged by inverting the mill and emptying through the loading port. The recovered material was sieved to separate the grinding media from the powder.

Variations to the milling conditions set out above are indicated in the variations column in the data tables. The key to these variations is shown in Table A.

Particle Size Measurement:

The particle size distribution (PSD) was determined using a Malvern Mastersizer 2000 fitted with a Malvern Hydro 2000S pump unit. Measurement settings used: Measurement Time: 12 seconds, Measurement cycles: 3. Final result generated by averaging the 3 measurements. Samples were prepared by adding 200 mg of milled material to 5.0 mL of 1% PVP in 10 mM hydrochloric acid (HCl), vortexing for 1 min and then sonicating. From this suspension enough was added into the dispersant (10 mM HCl) to attain a desired obscuration level. If necessary an extra 1-2 minutes of sonication was applied using the internal sonication probe in the measurement cell. The refractive index of the active ingredient to be measured was in the range of 1.49-1.73. Any variations to this general method are summarized in Table B.

XRD Analysis:

Powder X-Ray diffraction (XRD) patterns were measured with a Diffractometer D 5000, Kristalloflex (Siemens). The measurement range was from 5-18 degrees 2-Theta. The slit width was set to 2 mm and the cathode ray tube was operated at 40 kV and 35 mA. Measurements were recorded at room temperature. The recorded traces were subsequently processed using Bruker EVA software to obtain the diffraction pattern.

TABLE A

| | | Variations to milling conditions. | | | |
|---|---|---|---|---|---|
| Variation # | Mill type | Milling Speed (rpm) | Media size (inch) | Media Mass (kg) | Offload spped (rpm) |
| A | 1HD 1 L | | 0.25 | | |
| B | 1S 0.5 gal | | | 5 | |
| C | 1S 0.5 gal | | | 4 | |
| D | 1S 0.5 gal | 500 | | | |
| E | 1S 0.5 gal | 550-555 | | | |
| F | 1S 1.5 gal | 316-318 | | 21 | |
| G | 1S 1.5 gal | 500 | | 21 | |
| H | 1S 1.5 gal | 355 | | 21 | |
| I | 1S 1.5 gal | 355 | | 18 | |
| J | 1S 1.5 gal | | | 21 | |
| K | 1S 1.5 gal | | | 18.4 | |
| L | 1S 1.5 gal | 400 | | | |
| M | 1S 1.5 gal | | | 21 | 57 |
| N | 1S 1.5 gal | | | | 57 |
| O | 1S 0.5 gal | 400 | | | 400 |

TABLE A-continued

Variations to milling conditions.

| Variation # | Mill type | Milling Speed (rpm) | Media size (inch) | Media Mass (kg) | Offload spped (rpm) |
|---|---|---|---|---|---|
| P | 1S 0.5 gal | 500 | | | 350 |
| Q | HICOM | | ⅛ | | |
| R | HICOM | | | 11.7 | |

Only conditions reported in the table have changed as compared to conditions reported above.

TABLE B

Variations to particle size measurement conditions.

| Variation # | Sample Dispersant | Measurement Dispersant | Addition Method |
|---|---|---|---|
| 1 | | 0.1% PVP in DI water | Powder addition |
| 2 | 0.2% Pluronic L81 in DI water | DI water | |
| 3 | | Saturated glyphosate in DI water | Powder addition |
| 4 | | Saturated glyphosate in DI water | Powder addition |
| 5 | 1% PVP in DI water | DI water | Powder addition |
| 6 | | DI water | |
| 7 | 1% PVP in DI water | Saturated creatine in DI water | |
| 8 | 1% PVP in DI water | 10 mM HCl | |
| 9 | 0.2% Pluronic L81 in DI water | Acidified with 1M HCl | |
| 10 | 1% PVP in DI water | 0.1% PVP in DI water | |
| 11 | 1% PVP in DI water | 1% PVP in DI water | |
| 12 | | | Filtered before PSD measurement |

Abbreviations:
HCl: Hydrochloric acid
Nap: Naproxen acid
PSD: Particles size distribution
PVP: Polyvinyl pyrrolidone
RI: Refractive index
Rpm: Revolutions per minute
SLS: Sodium lauryl sulphate
SSB: Stainless Steel Balls
XRD: X-Ray Diffraction Other abbreviations used in the data tables are listed below in Table C (for actives), Table D (for matrices) and Table E (for surfactants). In the data tables single letter with example number abbreviations have been used to identify specific sample numbers within the table. The data tables shown in the figures the use of surfactant, matrix are interchangeable and do not necessarily define the nature of that material.

TABLE C

Abbreviations used for active pharmaceutical ingredients.

| API Name | Abbreviation |
|---|---|
| 2,4-Dichlorophenoxyacetic acid | 2,4D |
| Anthraquinone | ANT |
| Celecoxib | CEL |
| Cilostazol | CIL |
| Ciprofloxacin | CIP |
| Creatine Monohydrate | CRM |

TABLE C-continued

Abbreviations used for active pharmaceutical ingredients.

| API Name | Abbreviation |
|---|---|
| Cyclosporin A | CYA |
| Diclofenac Acid | DIC |
| Glyphosate | GLY |
| Halusulfuron | HAL |
| Indomethacin | IND |
| Mancozeb | MAN |
| Meloxicam | MEL |
| Metaxalone | MTX |
| Metsulfuron | MET |
| Naproxen Acid | NAA |
| Naproxen Sodium | NAS |
| Progesterone | PRO |
| Salbutamol | SAL |
| Sulfur | SUL |
| Tribenuran | TRI |
| FOOD | |
| Apricot kernel | APR |
| Cinnamon Ground | CNG |
| Cinnamon Quills | CNQ |
| Cocoa Nibs | CON |
| Cocoa Powder | COP |
| Coffee Beans | COF |
| Cloves | CLO |
| Dehydrated Peas | PEA |
| Dehydrated Beans | BEA |
| Fenegreek | FEN |
| Goji Berry | GOJ |
| Green Tea | GTE |
| Ground Ginger | GIN |
| Lavender | LAV |
| Linseed | LIN |
| Mangosteen | MST |
| Raspberry Leaf | RAS |
| Turmeric | TUR |

TABLE D

Abbreviations used for excipients.

| Matrix Name | Abbreviation |
|---|---|
| Calcium Carbonate | CAC |
| Full Cream Milk Powder | FCM |
| Glucose | GLU |
| Lactose Anhydrous | LAA |
| Lactose Monohydrate | LAC |
| Lactose Monohydrate Food Grade | LFG |
| Malic Acid | MAA |
| Maltitol | MAL |
| Mannitol | MAN |
| Skimmed Milk Powder | SMP |
| Sodium Bicarbonate | SB |
| Sodium Chloride | SC |
| Sorbitol | SOR |
| Sucrose | SUC |
| Tartaric Acid | TA |
| TriSodium Citrate Dihydrate | TCD |
| Whey Powder | WP |
| Xylitol | XYL |

TABLE E

Abbreviations used for surfactants

| Surfactant Name | Abbreviation |
|---|---|
| Aerosil R972 Silica | AS |
| Benzalkonium Chloride | BC |

TABLE E-continued

| Abbreviations used for surfactants | |
| --- | --- |
| Surfactant Name | Abbreviation |
| Brij700 | B700 |
| Brij76 | B76 |
| Cremophor EL | CEL |
| Cremophor RH-40 | C40 |
| Dehscofix 920 | D920 |
| Docusate Sodium | DS |
| Kollidon 25 | K25 |
| Kraftsperse 1251 | K1251 |
| Lecithin | LEC |
| Poloxamer 188 | P188 |
| Microcrystalline Cellulose | MCC |
| Poloxamer 407 | P407 |
| Polyethylene Glycol 3000 | P3000 |
| Polyethylene Glycol 8000 | P8000 |
| Polyoxyethylene 40 Stearate | P40S |
| Polyvinyl Pyrrolidone (Kollidon 30) | PVP |
| Primellose | PML |
| Primojel | PRI |
| Sodium Deoxycholate | SDC |
| Sodium Dodecyl Sulphate | SDS |
| Sodium Dodecylbenzenesulphonic Acid | SDA |
| Sodium N-Lauroyl Sarcosine | SNS |
| Sodium Octadecyl Sulphate | SOS |
| Sodium Pentane Sulphonate | SPS |
| Soluplus HS15 | SOL |
| Teric 305 | T305 |
| Tersperse 2700 | T2700 |
| Terwet 1221 | T1221 |
| Terwet 3785 | T3785 |
| Tween 80 | T80 |

Example 1: Spex Milling

A range of actives, matrices and surfactants in a variety of combinations were milled using the Spex mill. The details of these millings are shown in FIGS. 1A-1G together with the particle size distributions of actives that were milled.

These millings demonstrate that the addition of a small amount of surfactant to the milling matrix delivers a smaller particle size compared to millings of just an active and a single matrix. Some examples of this are samples Z and AA compared to sample Y; Sample AB compared to sample AC; sample AE compared to sample AD; sample AG compared to sample AF; sample AP compared to sample AO; sample AR compared to sample AQ, sample AT compared to sample AS; Samples AX, AY and AZ compared to sample AW; sample BC compared to sample BD; sample BI compared to BH; samples BL-BR compared to sample BK; samples CS-DB compared to sample DC. This last example is particularly noteworthy as these millings were undertaken at 45% v/v. This demonstrates the broad applicability of this invention. Some other examples of surfactant addition being beneficial for size reduction are samples DD-DG and DI-DK compared to sample DH; sample DM compared to sample DL. Other samples such as samples DY-EC compared to sample DX; sample AV compared to sample AU; samples B-H compared to sample A and samples K-M compared to sample J show this ti be also true when particle size statistics such the %<1 micron as used.

Note that this applies to mechanochemcial matrix milling as well. This is demonstrated by sample BI where naproxen sodium is milled with tartaric acid and converted to naproxen acid. FIG. 1H shows XRD data that demonstrates the transformation.

Other samples such as CB-CR show examples were surfactants suitable for use with IV formulations can be used to manufacture very small particles.

It is also noteworthy that samples DS and DT could be sized using a saturated solution of the active (salbutamol) demonstrating that actives with high water solubility can be measured as long as care is taken when measuring the size.

Two sets of data, samples N-Q and samples R-U, also demonstrate that the invention described herein is unique. In these samples the active milled with a matrix and surfactant produces small particles. When milled with matrix alone the particles sizes are larger, in the case of sample Q they are not even nanoparticles. When the active is milled with just 1% surfactant the resultant particle size is very large. Even when 80% surfactant is used the size is large.

Example 2: 110 mL Attritor

A range of actives, matrices and surfactants in a variety of combinations were milled using the 110 ml stirred attritor mill. The details of these millings are shown in FIG. 2A together with the particle size distributions of actives that were milled.

These millings also demonstrate that the addition of a small amount of surfactant to the milling matrix delivers a smaller particle size compared to millings of just an active and a single matrix in a small scale stirred mill as well as the vibratory Spex mill. Sample F also demonstrates that small particles can be achieved at high % actives when a surfactant is present. Sample D and E also show that the addition of the surfactant also increased the yield of powder from the mill.

Example 3: Second Matrix

In this example naproxen was milled with a mixture of two matrices using the Spex mill. The details of these millings are shown in FIG. 3A together with the particle size distributions of actives that were milled. Samples A and B were milled in a primary matrix of lactose monohydrate and 20% of second matrix. The particle size of these millings is smaller than the same milling with just lactose monohydrate (See example 1 sample No AH, FIG. 1B). The particle size is also smaller than naproxen milled in the secondary matrices (See example 1 sample No AI and AJ, FIG. 1B). This shows the mixed matrices have synergy together.

Samples C-E were milled in anhydrous lactose with 20% of a second matrix. All these samples had a particle size much smaller than naproxen milled in anhydrous lactose alone (See example 1 sample No AK, FIG. 1B).

These millings demonstrate that the addition of a second matrix to the primary milling matrix delivers a smaller particle size compared to millings with just a single matrix.

Example 4: 1 L Attritor

Two actives with various combinations of lactose monohydrate and SDS were milled using the 1 L stirred attritor mill. The details of these millings are shown in FIG. 4A together with the particle size distributions of actives that were milled.

Sample A and B are millings of meloxicam at 20%. While sample B has a slightly smaller particle size than sample A there is a dramatic difference in the amount of material recovered from the milling. Sample A, milled with 3% SDS has a high yield of 90% whereas sample B with no surfactant has practically no yield with all the powder caked in the mill.

In samples C-F the milling of 13% indomethacin shows that the use of a second matrix (tartaric acid) in combination with 1% SDS delivers the best outcome of a good particle size and high yield. Sample D which has just the mixed matrix has very good particle size but poor yield.

These results show that the addition of a small amount of surfactant improves milling performance.

Example 5: 750 mL Attritor

Two actives with various combinations surfactants were milled using the 750 ml stirred attritor mill. The details of these millings are shown in FIG. 5A together with the particle size distributions of actives that were milled.

In samples A-C three millings of naproxen are shown. Sample A has just 1% SDS as a surfactant. Samples B and C have a second surfactant present and these samples have a smaller particle size as measured by the %<500 nm, %<1000 nm and %<2000 nm.

In samples D-F three millings of indomethacin are shown. Sample D has just 1% SDS as a surfactant. Samples E and F have a second surfactant present and these samples have a smaller particle size compared to sample D.

These examples demonstrate that the use of combination of surfactants can be useful to achieve better reduction in particle size.

Example 6: ½Gallon 1S

A range of actives, matrices and surfactants in a variety of combinations were milled using the % gallon 1S mill. The details of these millings are shown in FIGS. 6A-C together with the particle size distributions of actives that were milled.

The following examples demonstrate the increased yield obtained when milling an active in a ½gallon 1S attritor mill with a surfactant as compared to no surfactant, with all other factors being identical. Sample C and D (FIG. 6A) shows Naproxen acid milled in Mannitol with yields of 92% and 23%, with and without surfactant. Sample S and AL (FIGS. 6B and C) show the same for glyphosate with yields of 95% and 26%, respectively. Sample AI and AJ (FIG. 6B) show Ciprofloxacin yields of 94% and 37% with and without surfactant while sample AM an AN (FIG. 6C) show Celecoxib yields of 86% and 57% with and without surfactants. Finally, samples AP and AQ (FIG. 6C) shows milling Mancozeb with or without surfactants results in yields of 90% and 56%, respectively.

The following examples illustrates that milling an active in a ½gallon 1S attritor mill with a surfactant as compared to without surfactant and all other factors identical, leads to smaller particle size after milling. Sample C and D (FIG. 6A) shows a D(0.5) of 0.181 and 0.319 with or without surfactant, while sample AM and AN (FIG. 6C) shows D(0.5) of 0.205 and 4.775 with and without surfactants.

The series of samples Q-S are timepoints taken from a single glyphosate milling. The data demonstrates that the size of the actives decreases with milling time.

Other samples such as V-AA show examples were surfactants suitable for use with IV formulations can be used to manufacture very small particles.

Some of the particle size data in FIGS. 6A-C was converted to a number average particle size and is shown in the tables. This number was calculated in the following way. The Volume distribution was transformed to the number distribution using the Malvern Mastersizer software. For each size bin the size of the bin was multiplied by the % of particles in the bin. This numbers were added together and divided by 100 to give the number average particle size.

Example 7: Metaxalone

Metaxalone was milled with various combinations of matrices and surfactants using a variety of mills. The details of these millings are shown in FIG. 7A together with the particle size distributions of actives that were milled. Samples A, B, E, G, H and I were milled in a Spex mill. Samples C, D and F were milled in the 750 ml atrittor. The remaining samples were milled in the ½ gallon 1S mill.

Samples A compared to sample B and sample H compared to sample G demonstrate that the addition of one or more surfactants enables the production of smaller active particles. Other millings such as samples C-F show that metaxalone can be milled small at very high active loadings. Sample I shows that disintegrant can be added during milling and not effect the production of small active particles. Note that the particle size in sample I is after filtration through a 10 micron filter. Sample N shows an alternative way to manufacture a formulation with small particles and disintegrants. In this example the powder from sample M was left in the mill and a wetting agent (PVP) and disintegrant were added. The powder was milled for a further 2 minutes and then unloaded with a very high yield of 97%.

The series of samples J-M are timepoints taken from a single milling. The data demonstrates that the size of the actives decreases with milling time.

Example 8: Hicom

A range of actives, matrices and surfactants in a variety of combinations were milled using the Hicom mill. The details of these millings are shown in FIG. 8A together with the particle size distributions of actives that were milled.

The data shows that the invention described herein can be used with the Hicom mill with its nutating action. The data in FIG. 8A shows that a variety of actives can be milled small in very short times and give very good yields at 500 gram scale.

Sample N and O show that cocoa powder can be reduced to very fine sizes in short times using the invention describes here in in combination with the Hicom nutating mill. Likewise Sample P shows that this is also the case for cocoa nibs.

Example 9: 1.5 Gallon 1S

A range of actives, matrices and surfactants in a variety of combinations were milled using the 1.5 Gallon 1S mill. The details of these millings are shown in FIGS. 9A-B together with the particle size distributions of actives that were milled.

The following examples demonstrate the increased yield obtained when milling an active in a 1.5 gallon 1S attritor mill with a surfactant as compared to no surfactant, with all other factors being identical. Sample J and N (FIG. 9A) shows yields of 51% and 80%, without and with surfactant. Sample K and P (FIG. 9A) show yields of 27% and 80%, without and with surfactant, while sample L (FIG. 9A) show a yield of 94% with surfactant and the control without surfactant (sample M, FIG. 9A) resulted in no yield due to caking within the mill.

The following examples illustrates that milling an active in a 1.5 gallon 1S attritor mill with a surfactant as compared to without surfactant and all other factors identical, leads to smaller particle size after milling. Sample F and G (FIG. 9A) shows a D(0.5) of 0.137 and 4.94 with or without surfactant, while sample K and P (FIG. 9A) shows D(0.5) of 0.242 and 0.152 without and with surfactants.

The series of samples AI-AL are timepoints taken from a single meloxicam milling. The data demonstrates that the size of the actives decreases with milling time.

Other samples such as A-E show examples were surfactants suitable for use with IV formulations can be used to manufacture very small particles.

Sample M was a milling of meloxicam in lactose monohydrate without surfactant. 3 minutes into the milling the mill refused to turn. The milling was stopped and started again but only ran for another 3 minutes before stopping again. At this point the mill was taken apart and no evidence of caking was found. However the powder had a gritty feeling to it and was locking the medium and shaft such that it was not possible to turn. The media was weighed and it as found that 150 grams of powder was on the media indicating that it was sticking to the media and making it hard to move. At this point the mill was re-assembled and the powder and media put back in. 30.4 grams of SDS was included in the milling making it similar to milling L. After the addition of the surfactant the mill was run for another 14 minutes (giving a total of 20 mins) without incident. After offloading the powder the media was weighed and the weigh of powder on the media was only 40.5 grams. This indicates the addition of surfactant has improved the milling performance and ability to mill the powder.

Some of the particle size data in FIGS. 9A-B was converted to a number average particle size and is shown in the tables. This number was calculated in the following way. The Volume distribution was transformed to the number distribution using the Malvern Mastersizer software. For each size bin the size of the bin was multiplied by the % of particles in the bin. This numbers were added together and divided by 100 to give the number average particle size.

Example 10: Large Scale 25/11 kg

Sample A (FIG. 10A) was milled in the Siebtechnik mill for 15 minutes. After this time the powder was completely caked onto the walls of the mill and the media. No powder could be removed to measure the particle size. At this point 0.25 g (1 w/w %) SLS was added to mill chamber and milling was then undertaken for a further 15 minutes. After the second period of milling in the presence of SLS powder was no longer caked onto the media and some free powder was also present. The observations made before and after the addition of the SLS demonstrate that the addition of the surfactant lessens the problem of caking. With the addition of surfactant the caked material could be recovered to become free powder again with small particle size.

Sample B-E was milled in horizontal Simoloyer mills. The details of these millings are shown in FIG. 10A together with the particle size distributions of actives that were milled.

The data shows that the invention described herein can be used with Simoloyer mills with their horizontal attritor action. Of particular note is example E which was milled at 11 kg scale. This demonstrates the invention described herein is suitable for commercial scale milling.

Sample F was milled in a vertical attritor mill (Union Process S-30). The details of this milling is shown in FIG. 10A together with the particle size distribution of the active milled.

The data shows that the invention described herein can be used with a S-30 mills with its vertical attritor action. Of particular note is that this milling was at 25 kg scale. This demonstrates the invention described herein is suitable for commercial scale milling.

Example 11: Food SPEX

A range of actives, matrices and surfactants in a variety of combinations were milled using the spex. The details of these millings are shown in FIGS. 11A-C together with the particle size distributions of actives that were milled.

This millings show that the invention disclosed herein is useful for milling food such as cocoa powder and cocoa nibs and other natural products such as seeds, flowers and berries to a small size.

The milling of dried berries (with some residual moisture) was successfully undertaken in sample AG. In contrast milling the berries on there own sample AQ resulted is sticky mass that incorporated the milling media. This shows that the invention described herein is useful for milling materials with residual water content and achieving a small particle size.

Example 12: Food ½Gallon 1S

A range of actives, matrices and surfactants in a variety of combinations were milled using the ½ gallon 1S mill. The details of these millings are shown in FIG. 12A together with the particle size distributions of actives that were milled.

This millings show that the invention disclosed herein is useful for milling food and natural products such as coffee, cocoa powder and cocoa nibs.

The milling of coffee (a material with a natural oil content) was successfully undertaken in sample A. In contrast milling the coffee with 1% lecithin (sample B) resulted is sticky mass that was caked at the top of the mill (see FIG. 12B). This shows that the invention described herein is useful for milling materials with natural oil content and achieving a small particle size as well as giving a good yield.

Example 13: Naproxen

Naproxen was milled in mannitol with a range of surfactants using the ½ Gallon 1S mill. The details of these millings are shown in FIG. 13A together with the particle size distributions of actives that were milled.

Naproxen acid milled in Mannitol with a surfactant (Sample A, D-J in FIG. 13A) leads to higher yields, as compared to Naproxen acid milled in Mannitol without surfactant (Sample K, FIG. 13A). Naproxen acid milled in Mannitol and either microcrystalline cellulose or the disintegrant primellose (sample L or M, FIG. 13A) leads to small particle size with D(0.5) around 0.25 in both cases.

Example 14: Filtration

Some matrices, milling aids or facilitating agents that are used by this invention are not water soluble. Examples of these are microcrystalline cellulose and disintegrants such as croscarmellose and sodium starch glycolate. In order to more easily characterise the particle size of the active after milling with these materials filtration methods can be used to remove them allowing a characterisation of the active. In the following examples naproxen was milled with lactose monohydrate and microcrystalline cellulose (MCC). The particle size was characterised before and after filtration and the ability of the filters to let through the naproxen was demonstrated using HPLC assays. The milling details and the particle size are shown in FIG. 14a. Note in this table the particle size with milling details is un-filtered. The particle size in the rows with no milling details is after filtration. The sample that was filtered is indicated in the Active material section. The HPLC assays were performed by taking samples before and after filtration through 10 micron poroplast filters. The samples taken were diluted to give a nominal concentration of 100 µg/ml. The HPLC assay data is shown in Table 14

Sample A was milled with 5% MCC. Before filtration the D50 was 2.5 µm, after filtration (sample B) the D50 was 183 nm. When sample B was assayed the concentration was 94 µg/ml indicating that filtration process retained little naproxen. A second milling (sample C) was undertaken without MCC. The D50 was 160 nm as would be expected. After filtration (sample D) the particle size was unchanged indicating that if the filtration process did remove any naproxen then it was removed in an even way. Some of sample C was then milled with MCC for 1 minute. This is long enough to incorporate the MCC into the powder but not long enough to affect the particle size distribution. Two millings were undertaken. Sample E incorporated 5% w/w MCC into the powder and Sample F 9% w/w. After incorporation of the MCC the particle size increased dramatically. These samples where then filtered (Sample E and F) and the size remeasured. After filtration the particle size is the same as Sample C which was the starting material. The assay of samples E-H indicates that filtration did not remove any naproxen of any significance. The combination of particle size and assay data clearly shows that material such as MCC can easily and successfully be removed allowing the true particle size of the active to be measured.

Samples I and J were millings conducted with 10 and 20% w/w MCC. The particle size post filtration is show as sample K and L. Again the filtration has delivered a reduction in particle size due to the removal of the MCC component. And again the HPLC assay of sample I-L shows little naproxen was lost during filtration.

This data also demonstrates that MCC can successfully be used as co matrix in the invention disclosed herein.

TABLE 14

The HPLC assay of naproxen before and after filtration of samples.

| Sample No. | HPLC Assay (µg/ml) |
|---|---|
| B | 94 |
| D | 93 |
| E | 99 |
| F | 96 |
| G | 98 |
| H | 97 |
| I | 94 |
| J | 89 |
| K | 91 |
| L | 84 |

Example 15: Dissolution of Nanoformulation Capsules

Example 15(a) Manufacture of Naproxen (200 mg) Nanoformulation Capsules

Nine sublots of naproxen nanoformulation milled powder were combined (Example 9, Sample Z-AH), roller compacted, processed in a Quadro® Comil®, and encapsulated.

For each milling sublot, 334 g of naproxen, 599 g of mannitol, 9.55 g of povidone K30, and 9.55 g of sodium lauryl sulfate were charged into an 8-qt V blender and mixed for 10 minutes, yielding a powder of approximate composition 35% naproxen, 63% mannitol, 1% povidone K30, and 1% sodium lauryl sulfate.

The blends were then milled individually and during the milling processes, unmilled material and samples were periodically discharged and their amounts recorded. After completion of each of the individual millings, an amount of croscarmellose sodium was added to each milling. The amount of croscarmellose sodium added was based on the theoretical amount of milled powder remaining in the mill, such that the final concentration of croscarmellose sodium in the powder would be 5.38% w/w upon addition of the calculated amount. After adding the croscarmellose sodium to the attritor mill, the mill was run for 2 minutes. The milled powder of approximate final composition 33.11% naproxen, 59.61% mannitol, 0.95% sodium lauryl sulfate, 0.95% povidone K30, and 5.38% croscarmellose sodium was then discharged from the mill.

Materials obtained from Example 9, Samples Z-AH were combined in a 1 cu. ft V-blender and mixed for 20 min. The mixed powder was processed in a Freund Model TF-156 roller compactor (screw speed=13.4, roll speed=4.1, pressure=55 kg/cm²). The powder was processed for approximately 55 min, yielding ribbons of 2.3 to 2.7 mm thickness.

The roller compacted ribbons were manually crushed and fed into the hopper of a Quadro® Comil® 197 equipped with an 1143 micron screen and 0.225 inch spacer, operating at 2000 rpm. The net yield of milled granular material was 4.183 kg.

The milled roller compacted granules were encapsulated into size 00 white opaque hard gelatin capsules using a MiniCap 100 Capsule Filling Machine equipped with size 00 change parts. The capsules were filled manually with a scraper and periodically checked for gross weight, closure integrity, and appearance. The target fill weight was 604 mg, and the average weight of an empty capsule shell was 117 mg. The filled capsules were then polished in a capsule polishing machine. The net yield of filled, polished capsules was 4,183 g (approximately 6,925 capsules).

Example 15(b): Manufacture of Indomethacin (20 mg) Nanoformulation Capsules

Indomethacin milled powder (750.0 g, Example 9, Sample T) was charged into the bowl of a KG-5 high shear granulator. Separately, a 30% solution of povidone K30 in purified water was prepared by dissolving 47.8 g of povidone in 111.6 g of purified water.

The high shear granulator was operated with an impeller speed of 250 rpm and a chopper speed of 2500 rpm. A portion of the povidone solution (80.3 g) was introduced into the granulator over a period of approximately 8 minutes using a peristaltic pump. An additional 30 g of purified water was then added to the granulation.

After the additions of povidone solution and water were completed, the wet granules were spread on to paper-lined trays to a thickness of approximately ½", and were dried in an oven at 70° C. for approximately 1 hour. The granules were then manually screened through a 10 mesh hand screen, and spread on to paper-lined trays for additional drying. The granules were dried for a second hour, and then tested for loss on drying; the LOD value was 1.987%.

The dried granules were processed in a Quadro CoMill (20 mesh screen, 0.225 inch spacer) at 2500 rpm, yielding 689.9 g of milled granules having the final composition of 12.60% indomethacin, 62.50% lactose monohydrate, 20.86% tartaric acid, 0.95% sodium lauryl sulfate, 3.09% povidone K30.

The granules were manually filled into size 4 white opaque hard gelatin capsules using a MiniCap 100 Capsule Filling Machine set up with size 4 capsule change parts. The target fill weight of each capsule was 158.7 mg and the average empty capsule shell weight was 38 mg. Capsules were filled manually using a scraper and periodically tested for gross weight. Tamping and vibration were adjusted as necessary to achieve the target fill weight.

The filled capsules were polished in a Capsule Polishing Machine, yielding a net weight of 803 g of filled capsules (approximately 4,056 capsules).

Example 15(c): Manufacture of Indomethacin (40 mg) Nanoformulation Capsules

Two separate granulation sublots were manufactured and combined to produce Indomethacin Nanoformulation capsules 40 mg.

Granulation sublot A was prepared by charging indomethacin milled powder (750.0 g, Example 9, Sample U) into the bowl of a KG-5 high shear granulator. Separately, a 30% solution of povidone K30 in purified water was prepared by dissolving 47.8 g of povidone in 111.5 g of purified water. The granulator was operated with an impeller speed of 250 rpm and a chopper speed of 2500 rpm. A portion of the povidone solution (80.3 g) was introduced into the granulator over a period of approximately 9 minutes, using a peristaltic pump. An additional 20 g of purified water was then added to the granulation.

After the additions of povidone solution and water were completed, the wet granules were spread on to paper-lined trays to a thickness of approximately ½".

Granulation sublot B was prepared by charging indomethacin milled powder (731.6 g, Example 9, Sample V and 18.4 g, Example 9, Sample U) into the bowl of a KG-5 high shear granulator. Separately, a 30% solution of povidone K30 in purified water was prepared by dissolving 47.8 g of povidone in 111.5 g of purified water. The granulator was operated with an impeller speed of 250 rpm and a chopper speed of 2500 rpm. A portion of the povidone solution (80.3 g) was introduced into the granulator over a period of approximately 10 minutes, using a peristaltic pump. An additional 20 g of purified water was then added to the granulation. After the additions of povidone solution and water were completed, the wet granules were spread on to paper-lined trays to a thickness of approximately ½". The wet granules from both sublots were dried in an oven at 70° C. for approximately 2.5 hours. The granules were then manually screened through a 10 mesh hand screen, and spread on to paper-lined trays for additional drying. The granules were dried for another 1.5 hours, until the LOD value was 1.699%.

The dried granules were processed in a Quadro CoMill (20 mesh screen, 0.225 inch spacer) at 2500 rpm. The milled granules were then added to an 8 qt V-blender and mixed for 5 minutes, yielding 1390.7 g of granules with a final composition of 12.60% indomethacin, 62.50% lactose monohydrate, 20.86% tartaric acid, 0.95% sodium lauryl sulfate, 3.09% povidone K30.

An IN-CAP® automated capsule filling machine (Dott. Bonapace & C., Milano, Italy) was set up with size (2) 16 mm dosing disc and size (2) tamping pins. Milled granules were charged into the encapsulator, along with size 1 white opaque hard gelatin capsule shells. The target capsule fill weight was 317.7 mg, and the average empty capsule shell weight was 75 mg. Tamping pins 1-4 were all set to 9 mm, and the encapsulator was run at speed 2. Weight checks, closure checks, and appearance checks were performed every 15 minutes. Filled capsules were polished in a capsule polishing machine. The net weight of filled, polished capsules was 1225.5 g (approximately 3,183 capsules).

Example 15(d): Manufacture of Meloxicam (7.5 mg) Nanoformulation Capsules

Milled powder (Example 9, Sample Q) was manually encapsulated using a capsule filling device (Cooper plate and capsule loader) into size "4" white-opaque hard-gelatin capsules. Upon encapsulation, each capsule contains 7.5 mg active ingredient with a total fill weight of 105 mg. The finished capsules were packaged in 40 cc HDPE bottles (50 counts per bottle) with the bottles being enclosed using an induction seal.

Example 15(e): Manufacture of Diclofenac (18 mg) Nanoformulation Capsules

Diclofenac milled powder (666.2 g, from Example 9, Sample W) was charged into the bowl of a KG-5 high shear granulator. Separately, a 30% w/w solution of povidone K30 was prepared by dissolving 60.0 g of povidone K30 in 140.0 g of purified water. The granulator was operated at a chopper speed of 250 rpm and impeller speed of 2500 rpm. A portion of the povidone solution (88.6 g) was introduced into the granulation over a period of approximately 9 minutes with a peristaltic pump. An additional 30 g of water was then added to the granulation.

The wet granules were spread on to paper-lined trays and dried in an oven at 70° C. for 2 hours.

They were then manually screened through a 10 mesh hand screen. After approximately 2.25 hours of drying time, the loss on drying was determined to be 0.559%.

The dried granules were processed in a Quadro CoMill fitted with a 200 mesh screen and 0.225 inch spacer, run at 1265 rpm. The process yielded 539.0 g of milled, dried granules.

The granules were filled into size 4 white opaque hard gelatin capsules using an IN-CAP® automated capsule filling machine (Dott. Bonapace & C., Milano, Italy). The machine was set up with size 4 change parts and a 10 mm dosing disc. The target fill weight was 124.8 mg, and the average weight of an empty capsule shell was 38 mg. The machine was run at speed setting #2. Tamping pin #4 was set to 21 mm; all other tamping pin settings were N/A.

The filled capsules were polished in a capsule polishing machine, and the net yield of filled capsules was 480.2 g (approximately 2,910 capsules).

Example 15(f): Manufacture of Diclofenac (35 mg) Nanoformulation Capsules

Two separate granulation sublots were used for the manufacture of Diclofenac Nanoformulation Capsules 35 mg. Granulation sublot A: 642.7 g of milled diclofenac powder (Example 9, Sample X) was charged into the bowl of a KG-5 high shear granulator. Separately, a 30% w/w solution of povidone K30 was prepared by dissolving 60.0 g of povidone K30 in 140.0 g of purified water. The granulator was operated at an impeller speed of 250 rpm and a chopper speed of 2500 rpm. A portion of the binder solution (85.5 g)

was introduced into the granulation over a period of approximately 8.5 minutes via a peristaltic pump. An additional 30 g of purified water was then added to the granulation at the same rate. The wet granules were spread on to paper-lined trays to a thickness of approximately ½".

Granulation sublot B: 519.6 g of milled diclofenac powder (Example 9, Sample Y) was charged into the bowl of a KG-5 high shear granulator. Separately, a 30% povidone solution was prepared by dissolving 60.0 g of povidone K30 in 140.0 g of purified water. The granulator was operated at an impeller speed of 250 rpm and a chopper speed of 2500 rpm. A portion of the povidone solution (69.1 g) was added to the granulation over a period of approximately 6.5 minutes. An additional 30 g of water was then added at the same rate. The wet granules were spread on to paper-lined trays to a thickness of approximately ½".

The wet granules from sublots A and B were dried in an oven at 70° C. for approximately 2 hours. They were then manually screened through a 10 mesh hand screen and tested for loss on drying. The LOD result was 0.316%.

The dried granules were milled in a Quadro CoMill fitted with a 200 mesh screen and 0.225 inch spacer, operated at 2500 rpm. The milled granules were charged into an 8 qt V-blender and mixed for 5 minutes, yielding 1020.2 g of granules.

The granules were filled into size 3 white opaque hard gelatin capsules using a MiniCap Capsule Filling Machine equipped with size 3 change parts. The target fill weight was 242.7 mg and the average weight of an empty capsule shell was 47 mg. The granules were filled into the capsule shells manually using a scraper. Vibration and tamping were adjusted to achieve the target fill weight. The filled capsules were polished on a capsule polishing machine, yielding 1149.2 g of filled capsules (approximately 3,922 capsules).

Example 15(g) Manufacture of Metaxalone (100 mg) Nanoformulation Capsules

Milled powder (Example 7, Sample N) was manually encapsulated using a capsule filling device (Profil) into hard-gelatin capsules.

Example 15(h) Dissolution Rate of Milled Naproxen

The Dissolution of milled naproxen (200 mg) capsules (see example 15a), and commercial Naprosyn® 250 mg (naproxen) tablets (Roche Pharmaceuticals®, Inc., USA) were determined using dissolution equipment set up as USP Apparatus II (paddles) with a stirrer speed of 50 rpm. The dissolution media was 900 ml of 0.3% SLS in 0.1 M sodium phosphate buffer at pH 5. The vessel temperature was 37° C. The capsules where weighted down with a wire sinker. Six test articles were tested and the data average for each time point. At each time point a 1 ml sample was taken from each dissolution vessel, filtered through a 0.45 μm filter and analyzed by HPLC. The data in Table 15a below reports the percent dissolved of the amount of active in each test article, for the specified time points.

TABLE 15a

Dissolution Profiles of Naprosyn ® Tablets 250 mg and Naproxen Nanoformulation Capsules 200 mg

| | Percent of Label Claim Dissolved (%) | |
| Time | Naprosyn Tablets 250 mg | Naproxen Nanoformulation Capsules 200 mg |
| --- | --- | --- |
| 0 | 0 | 0 |
| 5 | 24 | 19 |
| 10 | 40 | 53 |
| 15 | 49 | 77 |
| 20 | 55 | 90 |
| 45 | 73 | 98 |
| 60 | 79 | 99 |

The results demonstrate that the milled naproxen capsules dissolve more quickly and more completely than the commercial reference naproxen. Those of skill in the art will readily appreciate the advantages conferred by more rapid dissolution—more active agent is available at any given time point. Put another way, an equal quantity of dissolved naproxen may be obtained with an initially smaller dosage amount of milled naproxen, as opposed to the larger initial dose required for the reference naproxen to reach to the same quantity of dissolved naproxen. Additionally, as the results make clear, the reference naproxen does not achieve complete dissolution even by the final time point, while the milled naproxen achieves greater than 90% dissolution within 20 minutes, and substantially complete dissolution by the 45 minute time point. Again, a smaller dose of milled naproxen yields a quantity of dissolved naproxen for which a larger dose of reference naproxen would be required to equal.

Example 15(i): Dissolution Rate of Milled Indomethacin

In this example, dissolution rate is compared between 20 mg and 40 mg nanoformulations of the invention (Example 15(b) and 15(c)), and commercial reference indomethacin USP 25 mg capsules (Mylan Pharmaceuticals Inc). The dissolution was performed using Apparatus I (baskets) according to USP <711>. The dissolution medium (900 ml at 37° C.) was 100 mM citric acid buffer (pH 5.5±0.05); The apparatus was stirred at 100 rpm. Sampling times were 5, 10, 20, 30, 45, and 60 min plus an additional time point at 75 min (250 rpm). Sample of 8 mL were taken and filtered through a 0.45 μm PVDF filter. The samples were assay by UV-visible spectroscopy with a detection wavelength=319 nm. The data in Table 15b below reports the percent dissolved of the amount of active in each test article, for the specified time points.

TABLE 15b

Dissolution Profiles of Indomethacin Capsules USP (25 mg) and Indomethacin Nanoformulation Capsules (20 mg and 40 mg)

| | Percent of Label Claim Dissolved (%) | | |
| Time (min) | Indomethacin capsules USP, 25 mg | Indomethacin Nanoformulation Capsules 20 mg | Indomethacin Nanoformulation Capsules 40 mg |
| --- | --- | --- | --- |
| 0 | 0 | 0 | 0 |
| 5 | 20 | 47 | 31 |
| 10 | 28 | 83 | 66 |

TABLE 15b-continued

Dissolution Profiles of Indomethacin Capsules USP (25 mg) and
Indomethacin Nanoformulation Capsules (20 mg and 40 mg)

| | Percent of Label Claim Dissolved (%) | | |
|---|---|---|---|
| Time (min) | Indomethacin capsules USP, 25 mg | Indomethacin Nanoformulation Capsules 20 mg | Indomethacin Nanoformulation Capsules 40 mg |
| 20 | 36 | 99 | 93 |
| 30 | 40 | 100 | 96 |
| 45 | 43 | 100 | 96 |
| 60 | 46 | 101 | 97 |
| 75 | 63 | 101 | 97 |

The results demonstrate that the milled indomethacin capsules dissolve more quickly and more completely than the commercial reference indomethacin. Those of skill in the art will readily appreciate the advantages conferred by more rapid dissolution—more active agent is available at any given time point. Put another way, an equal quantity of dissolved indomethacin may be obtained with an initially smaller dosage amount of milled indomethacin, as opposed to the larger initial dose required for the reference indomethacin to reach to the same quantity of dissolved indomethacin. Additionally, as the results make clear, the reference indomethacin does not achieve complete dissolution even by the final time point, while the milled indomethacin, in both dosage forms, achieves greater than 90% dissolution within 20 minutes. Again, a smaller dose of milled indomethacin yields a quantity of dissolved indomethacin for which a larger dose of reference indomethacin would be required to equal.

Example 15(J): Dissolution Rate of Milled Meloxicam

In this example, dissolution rate is compared between a 7.5 mg nanoformulation of this invention (Example 15(d)), and two commercial reference products Mobicox® 7.5 mg Tablets and Mobic® 7.5 mg Capsules (Both Boehringer Ingelheim). Dissolution was performed using Apparatus II (paddles) according to USP <711>. The dissolution medium was 10 mM phosphate buffer (pH 6.1) with 0.1% w/w sodium lauryl sulfate (500 ml at 37° C.). The apparatus was stirred at 50 rpm. Samples were taken at various time points from 5 to 60 minutes. For each sample 1 mL was taken, filtered through a 0.45 μm filter and assayed by HPLC using a detection wavelength of 362 nm. The data in Table 15c below report the percent dissolved of the amount of active in each test article, for the specified time points.

TABLE 15C

Dissolution profiles of Commercial Meloxicam Tablets and
Capsules and Meloxicam Nanoformulation Capsules

| | Percent of Label Claim Dissolved (%) | | |
|---|---|---|---|
| Time (min) | Mobicox® Tablets 7.5 mg | Mobic® Capsules 7.5 mg | Meloxicam Nanoformulation Capsules 7.5 mg |
| 0 | 0 | 0 | 0 |
| 5 | 39 | 19 | 44 |
| 10 | 50 | 43 | 68 |
| 15 | 57 | 52 | |
| 20 | | | 82 |
| 30 | 66 | 64 | 86 |

TABLE 15C-continued

Dissolution profiles of Commercial Meloxicam Tablets and
Capsules and Meloxicam Nanoformulation Capsules

| | Percent of Label Claim Dissolved (%) | | |
|---|---|---|---|
| Time (min) | Mobicox® Tablets 7.5 mg | Mobic® Capsules 7.5 mg | Meloxicam Nanoformulation Capsules 7.5 mg |
| 45 | | | 89 |
| 60 | 73 | 72 | 93 |

The results demonstrate that the milled meloxicam capsules dissolve more quickly and more completely than the commercial reference meloxicam. Those of skill in the art will readily appreciate the advantages conferred by more rapid dissolution—more active agent is available at any given time point. Put another way, an equal quantity of dissolved meloxicam may be obtained with an initially smaller dosage amount of milled meloxicam, as opposed to the larger initial dose required for the reference meloxicam to reach to the same quantity of dissolved meloxicam. Additionally, as the results make clear, the reference meloxicam does not achieve complete dissolution even by the final time point, while the milled meloxicam achieves about 82% dissolution within 20 minutes, and reaches over 90% by the 60 minute time point. Again, a smaller dose of milled meloxicam yields a quantity of dissolved meloxicam for which a larger dose of reference meloxicam would be required to equal.

Example 15(K): Dissolution Rate of Milled Diclofenac

In this example, dissolution rate is compared between 18 mg and 35 mg nanoformulations of the invention (Example 15(e) and 15(f)), and commercial reference diclofenac Voltarol Dispersible Tablets 50 mg (Novartis, U.K) which contain 46.5 mg of diclofenac free acid, equivalent to 50 mg of diclofenac sodium. The dissolution method used was Apparatus I (baskets) according to USP <711> with a stirring speed of 100 rpm. The dissolution media was 0.05% sodium lauryl sulfate and citric acid solution buffered to pH 5.75. The dissolution volume was 900 mL and dissolution medium temperature was 37° C. Samples were tested at 15, 30, 45, and 60 minutes and at infinity. Infinity was defined as an additional 15 minutes at a higher rotation speed. A sample of 1 ml was taken at each time point, filtered and assayed by HPLC with the detection wavelength set at 290 nm. The data in Table 15d below report the percent dissolved of the amount of active in each test article, for the specified time points.

TABLE 15d

Dissolution Profiles for Voltarol® Dispersible Tablets
50 mg, Diclofenac
Nanoformulation Capsules 18 mg, and Diclofenac
Nanoformulation Capsules 35 mg

| | Percent Label Claim Dissolved (%) | | |
|---|---|---|---|
| Time | Voltarol Dispersible Tablets 50 mg | Diclofenac Nanoformulation Capsules 18 mg | Diclofenac Nanoformulation Capsules 35 mg |
| 0 | 0 | 0 | 0 |
| 15 | 52 | 91 | 82 |
| 30 | 59 | 94.0 | 95 |
| 45 | 63 | 94 | 95 |

TABLE 15d-continued

| | Dissolution Profiles for Voltarol ® Dispersible Tablets 50 mg, Diclofenac Nanoformulation Capsules 18 mg, and Diclofenac Nanoformulation Capsules 35 mg | | |
|---|---|---|---|
| | Percent Label Claim Dissolved (%) | | |
| Time | Voltarol Dispersible Tablets 50 mg | Diclofenac Nanoformulation Capsules 18 mg | Diclofenac Nanoformulation Capsules 35 mg |
| 60 | 65 | 94 | 95 |
| 75 | 87 | 94 | 95 |

The results demonstrate that the milled diclofenac capsules dissolve more quickly and more completely than the commercial reference diclofenac. Those of skill in the art will readily appreciate the advantages conferred by more rapid dissolution—more active agent is available at any given time point. Put another way, an equal quantity of dissolved diclofenac may be obtained with an initially smaller dosage amount of milled diclofenac, as opposed to the larger initial dose required for the reference diclofenac to reach to the same quantity of dissolved diclofenac. Additionally, as the results make clear, the reference diclofenac does not achieve complete dissolution even by the final time point, while the milled diclofenac achieves about 90% dissolution within 15 minutes. Again, a smaller dose of milled diclofenac yields a quantity of dissolved diclofenac for which a larger dose of reference diclofenac would be required to equal.

Example 15(l): Dissolution Rate of Milled Metaxalone

The dissolution of milled metaxalone (100 mg) capsules (Example 15(g)), and a portion (equivalent to 100 mg metaxalone) of commercial Skelaxin® 800 mg (metaxalone) tablets (King Pharmaceuticals®, Inc., USA) were determined using dissolution equipment set up as USP Apparatus II (paddles) with a stirrer speed of 100 rpm. The dissolution media was 1000 ml of 0.01 M HCL (pH 2). The vessel temperature was 37° C. The capsules were weighted down with a wire sinker. Three to six test articles were tested and the data averaged for each time point. At each time point each dissolution vessel was automatically sampled through a 1 μm filter and analyzed in flow through UV/Vis cells. The data in Table 15e below report the percent dissolved of the amount of active in each test article, for the specified time points.

TABLE 15e

| | Dissolution profiles of Skelaxin Tablets (100 mg portion) and Metaxalone Nanoformulation Capsules 100 mg. | |
|---|---|---|
| | Percent of Label Claim Dissolved (%) | |
| Time (min) | Metaxalone Nanoformulation Capsules 100 mg | Skelaxin (100 mg portion) |
| 0 | 0 | 0 |
| 5 | 4 | 0 |
| 9 | 43 | 1 |
| 13 | 75 | 1 |
| 20 | 88 | 2 |
| 30 | 93 | 5 |
| 40 | 93 | 7 |

TABLE 15e-continued

| | Dissolution profiles of Skelaxin Tablets (100 mg portion) and Metaxalone Nanoformulation Capsules 100 mg. | |
|---|---|---|
| | Percent of Label Claim Dissolved (%) | |
| Time (min) | Metaxalone Nanoformulation Capsules 100 mg | Skelaxin (100 mg portion) |
| 50 | 94 | 9 |
| 60 | 94 | 11 |

The results demonstrate that the milled metaxalone capsules dissolve more quickly and more completely than the commercial reference metaxalone. Those of skill in the art will readily appreciate the advantages conferred by more rapid dissolution—more active agent is available at any given time point. Put another way, an equal quantity of dissolved metaxalone may be obtained with an initially smaller dosage amount of milled metaxalone, as opposed to the larger initial dose required for the reference metaxalone to reach to the same quantity of dissolved metaxalone. Additionally, as the results make clear, the reference metaxalone does not achieve complete dissolution even by the final time point, while the milled metaxalone achieves about 87% dissolution within 20 minutes. Again, a smaller dose of milled metaxalone yields a quantity of dissolved metaxalone for which a larger dose of reference metaxalone would be required to equal.

Example 16: Materials for Powder Handling Characteristic Testing

Blends of powders with a range of actives were prepared using a variety of mills for a range of powder handling characteristic testing. These are detailed in FIG. 15 along with the particle size of the actives as determined by laser diffraction measurement in water based solvents.

Four samples of micronized active were also obtained from commercial API manufacturers. Two sample of meloxicam (G and H and two samples of indomethacin (M and N) were also tested. The particle size of these actives as determined by laser diffraction measurement in water based solvents is also shown in FIG. 15.

Three samples were prepared by blending micronized material into lactose/SDS mixture that had been previously been milled in an attritor mill. E is a blend of 6.8% w/w micronized meloxicam (G) and 93.2% w/w D for a total of 10.0 g. F is a blend of 6.8% w/w micronized meloxicam (H) and 93.2 w/w % D for a total of 10.0 g. These blends were prepared by mixing the respective ingredients. in a SPEX mill for 10 min, without the use of any media. (J) is a blend of powder size milled lactose (I) and 13% micronized indomethacin (N) prepared by combining I and N in a polyethylene bag and tumbling the bag end over end for a minimum of 10 times. The particle size of active in this blend is shown in FIG. 15.

A blend of 13% w/w indomethacin, 1% w/w SDS and 86% w/w lactose monohydrate was jetmilled (L) in a 10" Spiral Jet Mill (Powdersize Inc). The particle size of active in this blend is shown in FIG. 15.

The particle size of the blend as a dry powder was measured for a selection of the blends. The measurements were performed on a Malvern Mastersizer 2000 with a Scirocco 2000 measurement cell. All measurements were performed at a pressure of 3 Bar excepting O, P and Q which were measured at 4 Bar. Note also that example S and T were passed through a 100 micron sieve prior to measurement. The particle size of blends measured in this way is shown in FIG. 16.

Example 17: Content Uniformity of Meloxicam Milled with Lactose Monohydrate

Capsules containing the milled material were obtained using the Profill capsule filling system, specifically the system using size 4 capsules (100 units). Natural (clear) size 4 capsules (Capsuline) were used in the process. The empty capsules were loaded onto the equipment and the lids removed as per instructions. The milled material was added to the capsules by moving powder across the plate with a scraper until the surface was level. After the capsules were filled in this manner the plate supporting the capsules was tapped lightly (tapped on the side of the plate with the plastic scraper), resulting in settling of the powder in the capsules. Powder was then scraped across the capsules anew until surface was level. This procedure was repeated a total of three times. The lids of the capsules were repositioned and the capsules closed and removed from the Profill system.

Content uniformity of the capsules was analyzed using High Performance Liquid Chromatography (HPLC). Each sample was run according to the Meloxicam USP method and results obtained using the following formula;

$$\left[\frac{Ru}{Rs} \times C \times Dil \times \frac{100}{LC}\right] = \% \; LC$$

Where:
Ru=Peak Response (Area) of Meloxicam in Test Solution
Rs=Average Peak Response (Area) of Meloxicam obtained from all Standard Solution injections
C=Concentration of Meloxicam in Standard (mg/mL)
Dil=Dilution factor (mL)
LC=Label Claim (7.5 mg, desired level in final product)

Example 17(a)

Powder of A (Example 16) was capsulated on Profill size 4 equipment (A total of 100 capsules produced). Content uniformity (by HPLC) measured and the results summarized in Table 16.

TABLE 16

| | Assay of 10 individual Meloxicam capsules. | | | | | | | | | |
|---|---|---|---|---|---|---|---|---|---|---|
| | Sample # | | | | | | | | | |
| | 1 | 2 | 3 | 4 | 5 | 6 | 7 | 8 | 9 | 10 |
| Weight (mg) | 148.3 | 150.8 | 142.6 | 152.1 | 146.2 | 146.4 | 151.6 | 147.1 | 152.0 | 143.9 |
| Assay (% LC) | 98.9 | 100.3 | 94.0 | 102.9 | 98.8 | 99.6 | 106.1 | 99.5 | 105.6 | 98.1 |
| Weight Corrected (% LC) | 98.2 | 97.9 | 97.0 | 99.6 | 99.5 | 100.1 | 103.0 | 99.6 | 102.3 | 100.3 |

Note:
Weight includes gelatin capsule.

A test of fill weight consistency was performed on 100 capsules by weighing each capsule individually and subtracting the gelatin capsule weight. The data is shown in Table 17.

TABLE 17

| Weight distribution of 100 size 4 capsules filled on Profill system. | |
|---|---|
| Weight distribution | No. of Capsules |
| 110 mg ± 5 mg | 78 capsules |
| 110 mg ± 5-10 mg | 21 capsules |
| 110 mg ± >10 mg | 1 capsule |

Example 17(b)

Sample B (Example 16) powder was capsulated on Profill size 4 equipment (A total of 600 capsules produced). Content uniformity (by HPLC) was measured and the results summarized in Table 18.

TABLE 18

| | Assay of 10 individual Meloxicam capsules. | | | | | | | | | |
|---|---|---|---|---|---|---|---|---|---|---|
| | Sample # | | | | | | | | | |
| | 1 | 2 | 3 | 4 | 5 | 6 | 7 | 8 | 9 | 10 |
| Weight (mg) | 138.1 | 143.3 | 139.0 | 141.9 | 144.1 | 143.4 | 133.7 | 137.5 | 147.9 | 142.7 |
| Assay (% LC) | 93.6 | 96.8 | 92.2 | 91.5 | 98.6 | 96.7 | 88.1 | 90.7 | 102.1 | 94.7 |

TABLE 18-continued

| Assay of 10 individual Meloxicam capsules. | | | | | | | | | |
|---|---|---|---|---|---|---|---|---|---|
| Sample # | | | | | | | | | |
| 1 | 2 | 3 | 4 | 5 | 6 | 7 | 8 | 9 | 10 |
| Weight Corrected (% LC) 99.4 | 99.0 | 97.2 | 94.5 | 100.3 | 98.9 | 96.6 | 97.1 | 101.2 | 97.3 |

Note:

Weight includes gelatin capsule.

A test of fill weight consistency was performed on 100 capsules by weighing each capsule individually. This data is shown in Table 19.

TABLE 19

| Weight distribution of 100 size 4 capsules filled on Profill system. | |
|---|---|
| Weight distribution | No. of Capsules |
| 140 mg ± 5 mg | 84 capsules |
| 140 mg ± 5-10 mg | 16 capsules |
| 140 mg ± >10 mg | 0 capsule |

Note:
Weight includes gelatin capsule.

Subtracting the capsule weight the following weight distributions were found:

Average fill weight of powder=104.1 mg
Average fill weight of Meloxicam=7.10 mg
Average % Label Claim of Meloxicam=94.6%

Example 17(c)

Sample C (Example 16) powder was capsulated on Profill size 4 equipment (A total of 600 capsules produced) Content uniformity (by HPLC) measured and the results summarized in Table 20.

TABLE 20

| Assay of 10 individual Meloxicam capsules. | | | | | | | | | |
|---|---|---|---|---|---|---|---|---|---|
| Sample # | | | | | | | | | |
| 1 | 2 | 3 | 4 | 5 | 6 | 7 | 8 | 9 | 10 |
| Weight (mg) 144.3 | 144.4 | 154.2 | 143.5 | 136.5 | 149.4 | 138.2 | 137.3 | 144.5 | 133.0 |
| Assay (% LC) 97.6 | 96.7 | 106.6 | 97.7 | 91.2 | 102.8 | 90.8 | 91.6 | 96.0 | 87.3 |
| Weight Corrected (% LC) 99.2 | 98.2 | 101.3 | 99.8 | 97.9 | 100.9 | 96.3 | 97.8 | 97.4 | 96.2 |

Note:

Weight includes gelatin capsule.

A test of fill weight consistency was performed on 52 capsules by weighing each capsule individually. The data is shown in Table 21.

TABLE 21

| Weight distribution of 52 size 4 capsules filled on Profill system. | |
|---|---|
| Weight distribution | No. of Capsules |
| 140 mg ± 5 mg | 44 capsules |
| 140 mg ± 5-10 mg | 6 capsules |
| 140 mg ± >10 mg | 2 capsule |

Note:
Weight includes gelatin capsule.

Subtracting the capsule weight the following weight distributions were found:

Average fill weight of powder=105.1 mg

Average fill weight of Meloxicam=7.15 mg

Average % Label Claim of Meloxicam=95.3%

The above example illustrates that milling Meloxicam in lactose monohydrate results in a homogenous mixture upon completion, as indicated by the content uniformity results. Furthermore, the simple hand-filling of size 4 capsules on Profill equipment, using standard hard gelatine capsules, results in a narrow weight distribution range of the filled capsules, indicating excellent flow properties of the milled powder obtained in this process. This indicates that nanoparticles of meloxicam have been made by the process outlined herein with improved powder handling characteristics. Such improved powder handling characteristics will be highly beneficial in a commercial scale formulation process.

Example 18: Content Uniformity after Segregation

Seven materials from example 16 were subjected to a segregation study. The blends were placed into 15 ml narrow plastic tubes and placed on a roller table for 16 hours. The roller table was placed on a gentle incline in order to promote segregation. After doing this the powders were visibly segregated into coarse and fine particles. The tubes were prepared with three holes drilled at fixed levels and samples were taken from these and assayed by HPLC. Samples were taken at the top, middle and bottom positions. An assay was also taken of the blend prior to segregation. Each assay was the average of three injections. The % that each sample deviated from the assay of material before segregation is shown in Table 22. Blends that have superior content uniformity after segregation will have small % deviations, while blends that have large % deviations that vary with sample position indicate stratification of the active across the levels of the tube, that is bad content uniformity. The data shows that all blends produced by this invention (B, C, K) retain uniformity after segregation. The blends of micronized active and attritor milled lactose (D, E, J) all show very poor content uniformity after segregation. The blend of active and excipients (L) that was jet milled also have superior content uniformity. This is because the particle size of the active and excipients are very similar meaning that little or no segregation has occurred. However as the following examples show this blend has many other power handling characteristics that are very poor.

TABLE 22

Shows the deviation of the assay (from before segregation) of active present in various blends at three positions in a tube that the blends have segregated in.

| Sample # | % Deviation of assay from unsegregated blend | | |
| | Top | Middle | Bottom |
| --- | --- | --- | --- |
| B | 1.4 | 0.8 | 0.8 |
| C | 0.4 | 0.4 | 0.6 |
| E | 10.4 | 7.0 | 1.7 |
| F | 8.5 | 5.4 | 11.5 |
| J | 10.3 | 36.3 | 1.4 |
| K | 0.5 | 0.4 | 1.5 |
| L | 0.5 | 0.8 | 0.5 |

Example 19: Powder Adherence Measurements

Powder Adherence to material surfaces was measured using three different media; Stainless steel, Polypropylene and Glass as detailed below. Samples B, C, D, E, G, H, J, K, L and M from Example 16 were tested.

Figure 17:
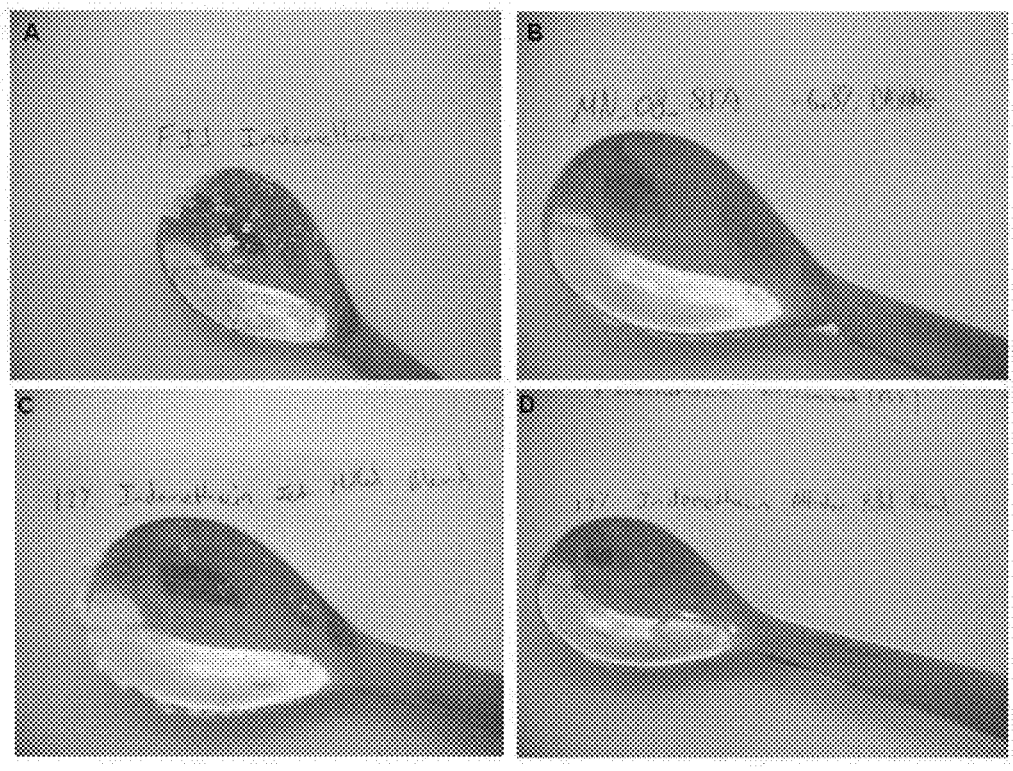
FIG. 17: Powder adherence measurements for stainless steel; A: Example 16, M; B: Example 16, E; C Example 16, L; D: Example 16, K.

Stainless steel: A tared stainless steel spatula was used to scoop a portion of each blend and deposit the sample back into the container by a consistent action of inverting the spatula through 360°. The residual mass of the powder remaining of the spatula was recorded. Three measurements were performed for each sample. The average of the mass measured and the % RSD between the three measurements are shown in FIG. 16. In FIG. 17 some images of the residual powder on the spatula are shown. Images A (sample M), B (sample E) and C (Sample L), conventional active/blends, clearly show more residual powder than D (sample K) which is a blend made by this invention.

Figure 18:
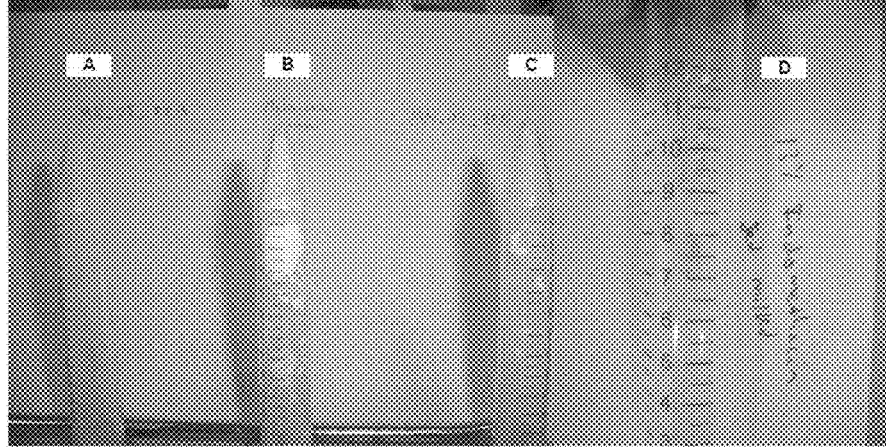
FIG. 18: Powder adherence measurements for Polypropylene; A: Example 16, B; B: Example 16, G; C Example 16, F; D: Example 16, L.

Polypropylene: The sample was loaded into a preweighed polypropylene centrifuge tube, which was rolled on a roller table for 5 minutes and subsequently inverted by a consistent action. The residual mass on the tube was recorded The average of the mass measured and the % RSD between the three measurements are shown in FIG. 16. In FIG. 18 some images of the residual powder on the plastic tubes are shown. Images B (sample E), C (sample G) and D (Sample L) are conventional active/blends and show varying degrees of powder clumped onto the tube. Image A (sample B), a blend made by this invention has only a fine coating of residual powder.

Figures 19, 20:
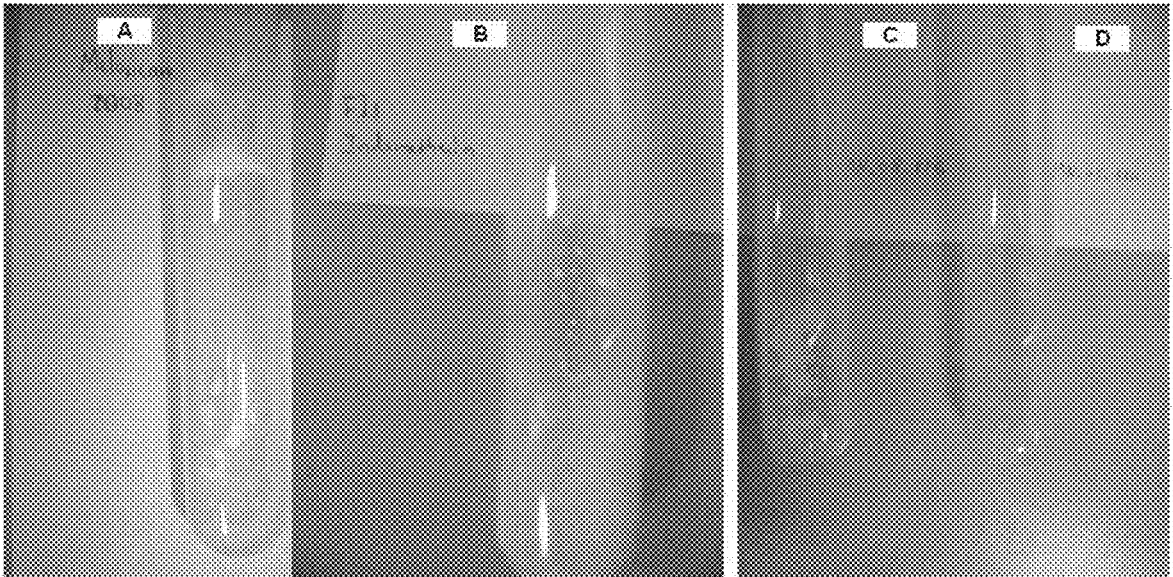
FIG. 19: Powder adherence measurements for Glass; A: Example 16, G; B: Example 16, M; C Example 16, F; D: Example 16, B.
FIG. 20: Bulk and Tap bulk density data and data from powder rheology measurements of various actives/blends from example 16
Figure 21:
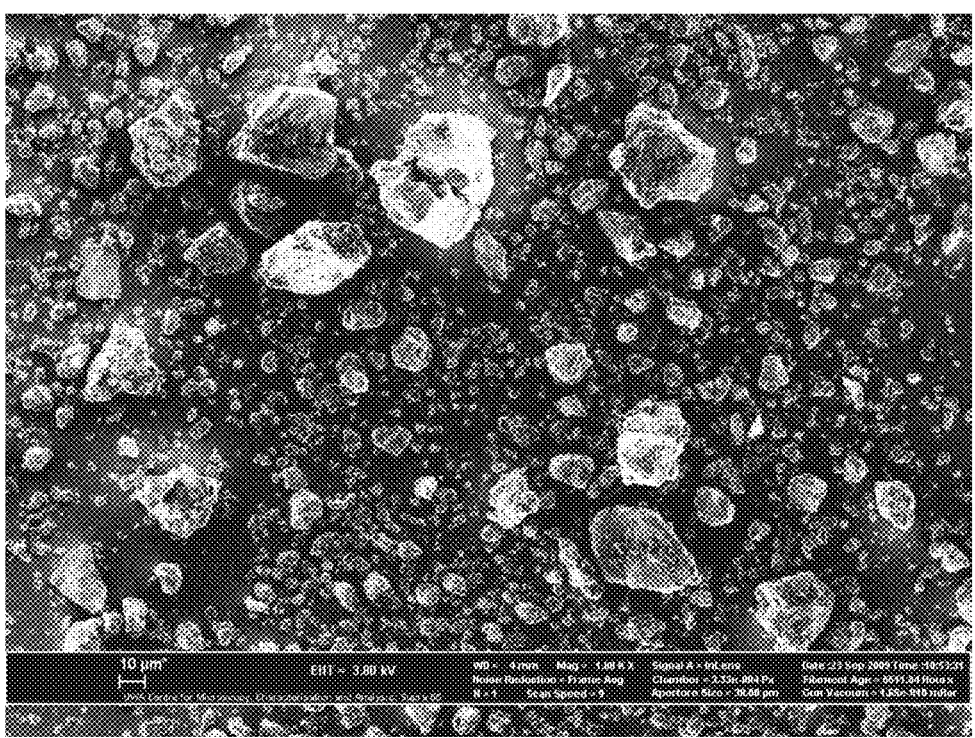
FIG. 21: SEM of Example 16 Sample S after 20 minutes milling 1,000×
Figure 22:
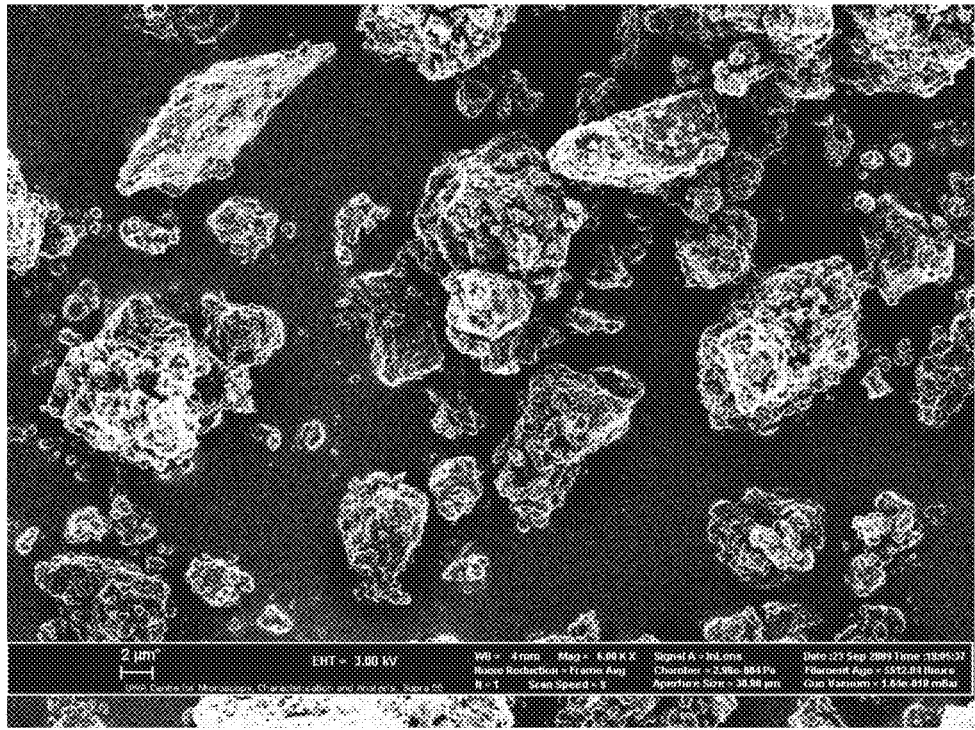
FIG. 22 SEM of Example 16 Sample S after 20 minutes milling 6,000×
Figure 23:
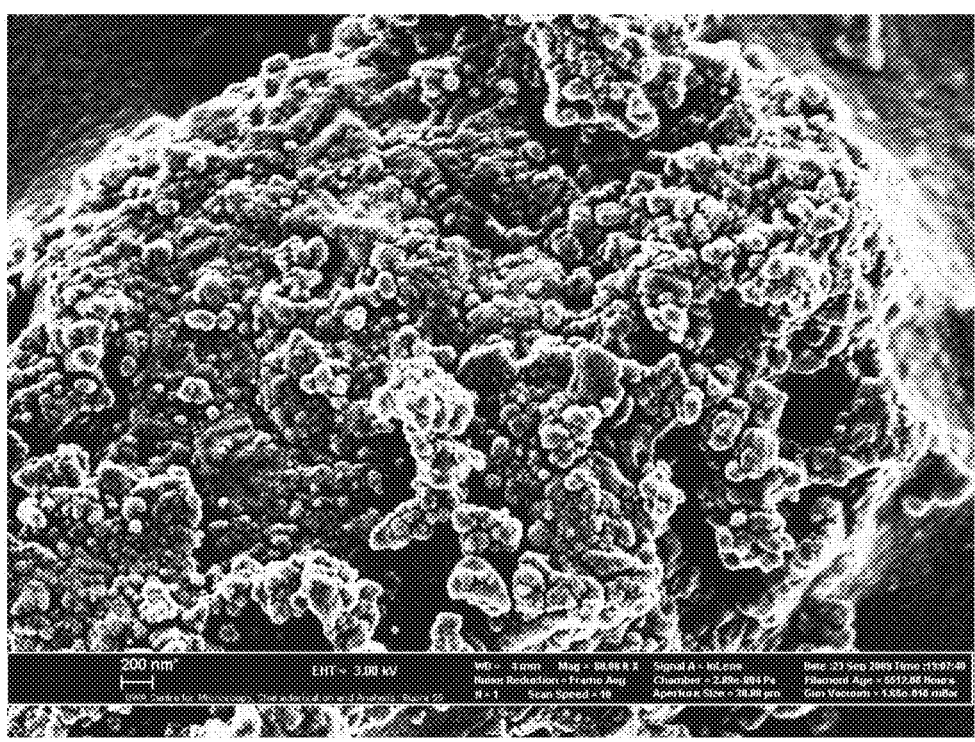
FIG. 23: SEM of Example 16 Sample S after 20 minutes milling 60,000×
Figure 24:
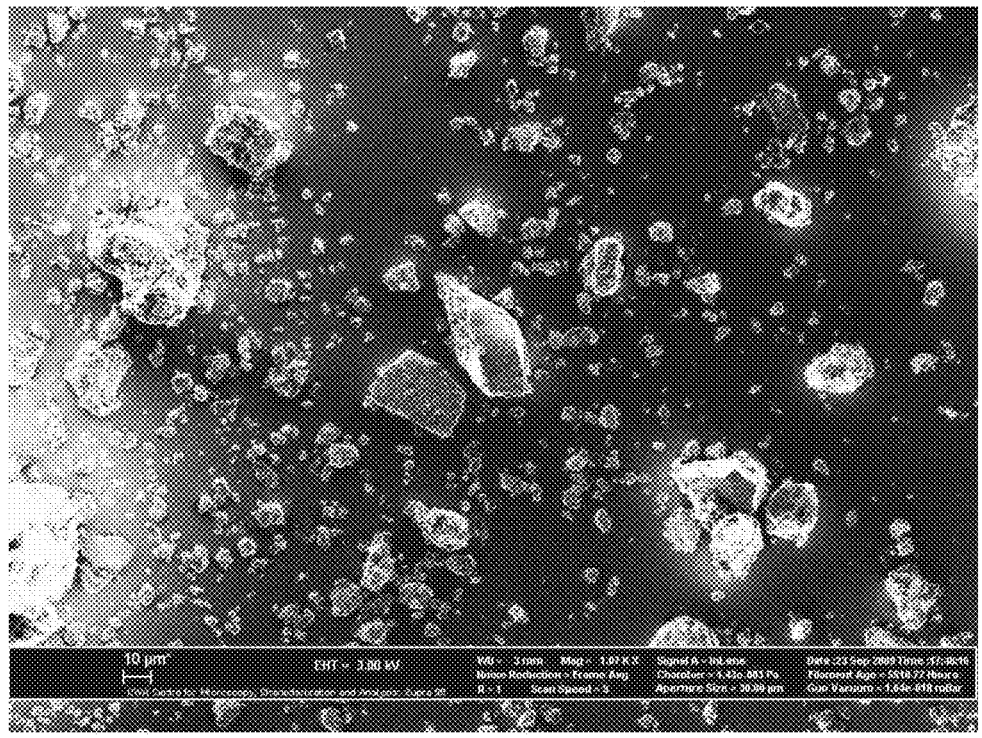
FIG. 24 SEM of Example 16 Sample S after 30 minutes milling 1,000×
Figure 25:
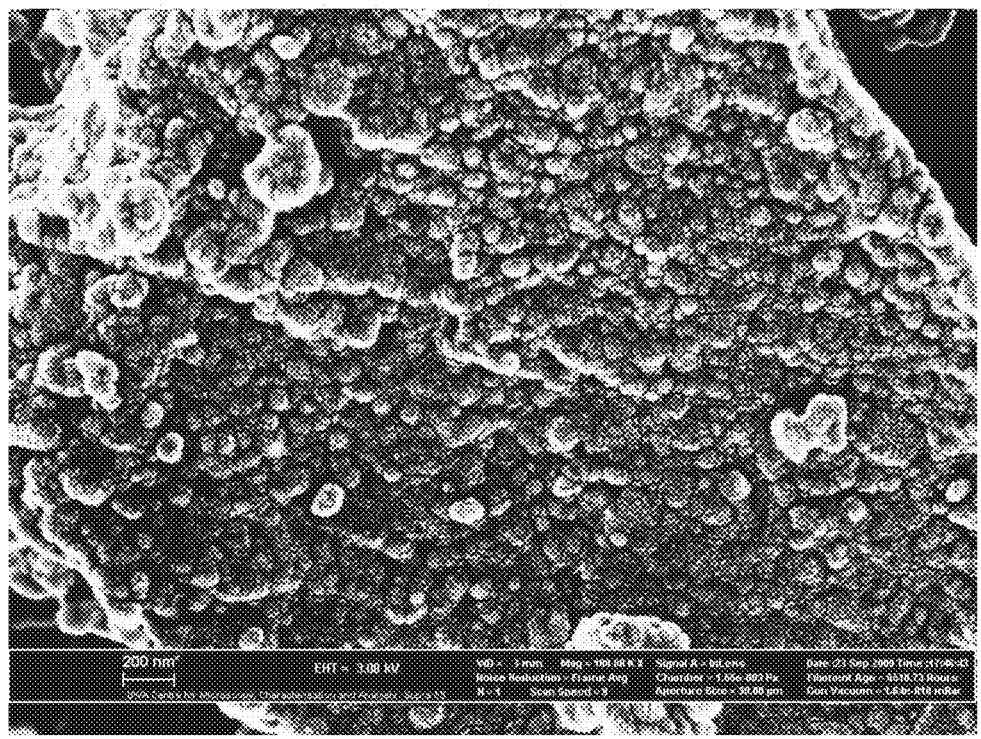
FIG. 25: SEM of Example 16 Sample S after 30 minutes milling 100,000×
Figure 26:
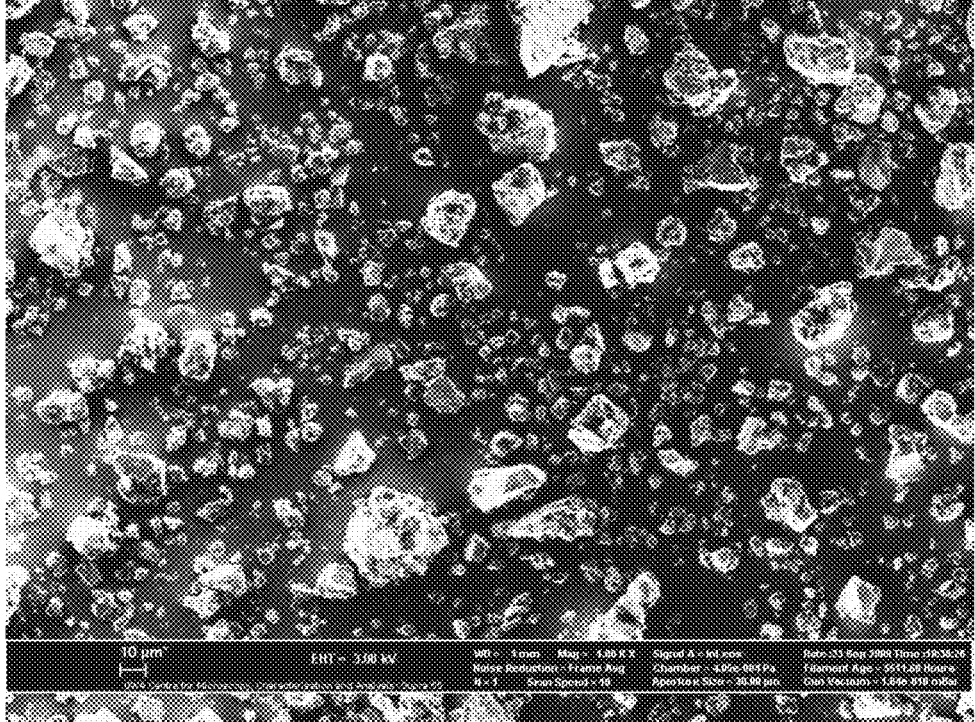
FIG. 26: SEM of Example 16 Sample R after 20 minutes milling 1,000×
Figure 27:
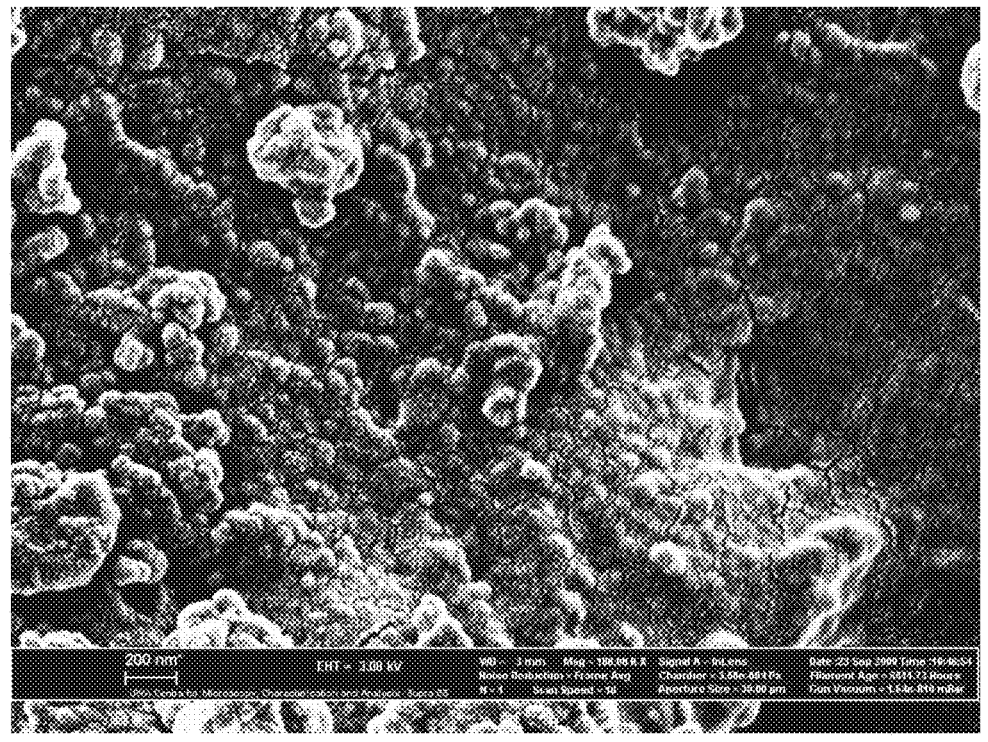
FIG. 27: SEM of Example 16 Sample R after 20 minutes milling 100,000×
Figure 28:
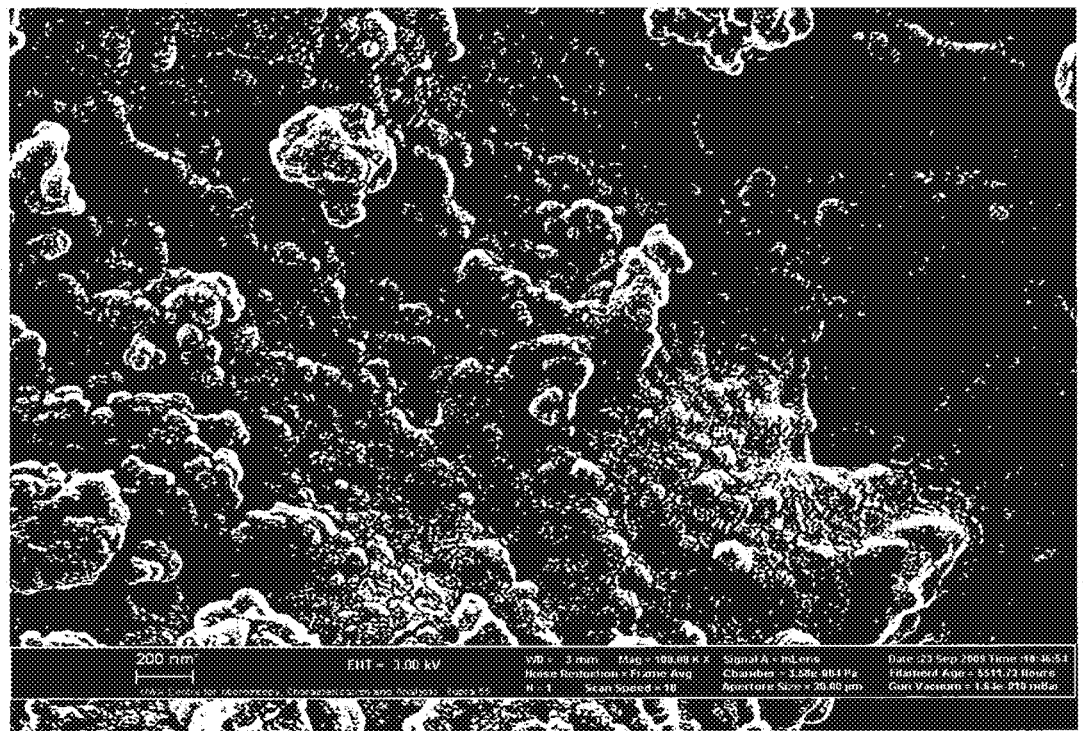
FIG. 28: SEM of Example 16 Sample R after 20 minutes milling 100,000×

Glass: Each sample was loaded into a preweighed glass tube, rolled on a roller table for 5 minutes and subsequently inverted by a consistent action. The residual mass on the glass tube was recorded. Only one measurement was performed for each sample. The data is shown in FIG. 16. In FIG. 19 some images of the residual powder on the glass tubes are shown. Images A (sample G), B (sample M) and C (sample F) are conventional active/blends and show varying degrees of powder clumped onto the tube. Image D (Sample B), a blend made by this invention has very little residual powder.

Overall the data of residual masses shown in FIG. 16 indicates that blends made by this invention show less adherence to these three materials compared to actives and blends made by conventional techniques.

Example 20: Angle of Repose Measurements

Angle of repose measurements were made on three indomethacin blends and one micronized active from Example 16. Measurements were made using a plastic column (diameter 23 mm) supported on paper. The column was loaded with the powder sample (15-20 g). The powder was deposited from the column by a consistent slow upward raising of the column. The angle of repose was calculated from the measurement of the height and the average radius of the powder deposit. The measurement was repeated 4-7 times for each sample. The angle of repose and % RSD across the measurements are shown in FIG. 16. The data shows that the blend produced with this invention (sample K) has a lower angle of repose compared to the blend of active with attritor milled lactose (Sample J) and the micronized indomethacin (Sample M) indicating powder with superior flow. The blend that was jetmilled (Sample L) had a low angle of repose but this was because the powder had agglomerated to form large balls of powder. This is not a desirable power handling characteristic.

Example 21: Bulk and Tap Bulk Density

Bulk and tap bulk density measurements were made on a number of the actives/blends from example 16. The measurements were performed according to USP <616>. The data from these measurements is shown in FIG. 20.

Example 22: Powder Rheology

Powder Rheology measurements were made on three indomethacin blends and one micronized active from Example 16. The measurements were conducted on Freeman Technology FT4 powder rheometer. The analysis was conducted according to the standard operating procedures of the instrument. The data from these measurements, Basic Flow Energy (FBE), Specific Energy (SE), Pressure Drop (PD15) and Compressibility (CPS18) are shown in FIG. 20. BFE is the energy (mJ) needed to displace a conditioned and stabilized powder at a given flow pattern (−5° helix) and flow rate (100 mm/s). The BFE was taken at the seventh test. The lower the BFE the more superior the powder rheology. The data shows that the blend made by this invention (Sample K) is superior to the active (Sample N) and two other blends (Sample J, L) made using conventional approaches. The SE is a measure of the energy per unit mass (mJ/g) needed to displace a conditioned powder where the rheometer blade is used in an upward lifting mode of displacement. The SE is a measure of cohesivity. The higher the SE the more cohesive a powder is. The data shows that the blend made by this invention (Sample K) is less cohesive than the active (Sample N) and two other blends (Sample J, L) made using conventional approaches. PD15 is the pressure drop (mBar) across the powder bed with a normal stress of 15 kPa applied. The air velocity across the bed was 2.0 mm/s. A highly permeable powder has a low pressure drop and is a desirable powder handling characteristic. The data shows that the blend made by this invention (sample K) has a lower pressure drop than the active (sample N) and two other blends (Sample J, L) made using conventional approaches. CPS18 measures the percentage (%) by which the bulk density has increased with a normal stress of 18 kPa applied. A lower compressibility is an indication of superior powder flow properties. The data shows that the blend made by this invention (sample K) has a lower compressibility than the active (Sample N) and two other blends (Sample J, L) made using conventional approaches.

Example 23: Aerodynamic Particle Size

Two blends of 1% salbutamol (albuterol) where prepared according to Example 16 sample S and T. These two blends where then passed through a 100 micron sieve prior to measurement. The two blends were then tested for aerodynamic particle size.

Example 23(a): Aerosizer Measurements

The two samples were measured on a TSI Aerosizer with a Aerodisperser set to a medium shear force and feed rate. Deagglomeration was set to normal and pin vibration was on. The particle size statistics (volume distribution) for these measurements are shown in Table 23.

TABLE 23

| Volume distribution particle size data from Aerosizer measurements. | | | |
|---|---|---|---|
| Sample name | Mean (μm) | D[50] (μm) | D[4.3] (μm) |
| Example 16 S | 16.8 | 18.9 | 19.0 |
| Example 16 T | 19.7 | 21.9 | 21.9 |

Example 23(b): Next Generation Impactor Measurements

The two blends of 1% salbutamol (Example 16 S, T) as well as a commercial blend (Ventolin Rotocaps (200 μg), Allen and Hanburys) were all tested in triplicate on a Next Generation Impactor (NGI). Approximately 20 mg of two 1% salbutamol blends were filled into gelatine capsules to give a similar nominal dose of 200 μg. The data from these measurements is shown in Table 24. The mean of the three measurements and RSD (%) are shown. One key finding is that the powder flow properties of the two blends made using this invention (S, T) are superior to the commercial blend. In the table the amount of material left in the capsule and device after testing (Residual in Capsule+Device) was high in the commercial sample compared to the other two blends. Another way of expressing this result was the percent delivered. This is the % of the total recovered dose that was delivered to the testing device. For the two blends made with this invention the percentage delivered was about 97% while the commercial blend only delivered 82%. All three blends delivered active into the Fine Particle Fraction (FPF) size range. This is the range needed for a blend to be useful as an inhaled formulation. The fact that the two blends made with this invention could deliver active into the FPF range and that the MMAD of the active was 5 micron or less indicates that the invention herein is useful for formulating inhaled pharmaceutical medicaments.

TABLE 24

| Data from the NGI measurements on the two blends from Example 16 and the commercial blend. | | | | | |
|---|---|---|---|---|---|
| | Ventolin | | Example 16 S | | Example 16 T | |
| Sample | Mass (μg) | RSD | Mass (μg) | RSD | Mass (μg) | RSD |
| Induction Port | 33.7 | 13.5 | 32.6 | 6.1 | 29.8 | 0.0 |
| Pre-separator | 86.0 | 4.7 | 104.3 | 2.7 | 111.6 | 1.5 |
| Stage 1 | 14.7 | 9.0 | 18.1 | 9.9 | 14.2 | 4.3 |
| Stage 2 (6.1 μm) | 18.2 | 12.5 | 11.2 | 7.6 | 10.6 | 35.5 |
| Stage 3 (3.4 μm) | 21.8 | 8.9 | 6.0 | 3.8 | 5.7 | 10.0 |
| Stage 4 (2.2 μm) | 23.3 | 10.3 | 3.8 | 5.3 | 3.9 | 8.3 |
| Stage 5 (1.3 μm) | 12.3 | 11.7 | 1.7 | 6.9 | 2.8 | 22.3 |
| Stage 6 (0.7 μm) | 3.0 | 24.0 | 1.0 | 6.0 | 1.1 | 23.6 |
| Stage 7 (0.4 μm) | 1.4 | 27.7 | 0.4 | 25.0 | 0.4 | 0.0 |
| MOF (0.2 μm) | 0.3 | 45.8 | 0.1 | 0.0 | 0.2 | 34.6 |
| Residual in Capsule + Device | 45.7 | 10.4 | 5.5 | 3.8 | 3.3 | 4.7 |
| Total recovered dose | 260.5 | 1.7 | 184.7 | 2.0 | 183.4 | 2.2 |
| Delivered dose (DD) | 214.7 | 3.4 | 179.1 | 2.1 | 180.1 | 2.3 |
| Percent delivered | 82.4 | 2.3 | 97.0 | 0.2 | 98.2 | 0.1 |
| FPD (μg < 5 μm) | 74.6 | 6.7 | 20.2 | 3.7 | 20.9 | 17.4 |
| FPF (% < 5 μm relative to DD) | 34.7 | 5.2 | 11.3 | 1.6 | 11.6 | 15.1 |
| MMAD (μm) | 2.6 | 6.0 | 5.2 | 2.2 | 4.6 | 2.5 |

Example 23(c) 2 Content Uniformity

One of the blends measured S (Example 16) was also tested for content uniformity before NGI testing. Ten samples were taken from the blend and each was assayed. The data from those 10 assays is shown in Table 25. The data shows that the blend has excellent uniformity even at this low active loading. It should be noted that the blend was manufactured in Australia and transported to the USA for testing and the fact that the content uniformity has been retained is strong testament to the excellent properties of material made with this invention.

TABLE 25

| Content uniformity data for sample S (Example 16). | | | | | | | | | | | | |
|---|---|---|---|---|---|---|---|---|---|---|---|---|
| | Sample No. | | | | | | | | | | | |
| | 1 | 2 | 3 | 4 | 5 | 6 | 7 | 8 | 9 | 10 | Ave | RSD (%) |
| w/w % Salbutamol | 0.92 | 0.91 | 0.90 | 0.90 | 0.91 | 0.91 | 0.90 | 0.90 | 0.90 | 0.90 | 0.91 | 0.54 |

Example 24: SEM

For two of the blends in Example 16 S and R SEM images were taken and are shown in FIGS. 21-27. For sample S images are shown for a sample taken at the 20 minute time point of this milling and at the end of the milling at 30 mins. For sample R the images are taken for the sample taken at 20 minutes. The images at low magnification show the composite particles which are or order 5-30 micron. The images at high magnification show that the composite particles are made up of particles of order 200 nm or less.

The invention claimed is:

1. A method for producing a blend containing nanoparticles and microparticles of biologically active material characterised by content uniformity, as measured by concentration of active material, after size segregation, varies from the average content by less than 4.0%, wherein the said method comprises the steps of: dry milling a solid biologically active material, sodium lauryl sulfate and a millable grinding matrix selected from the group consisting of lactose and mannitol in a mill comprising a plurality of milling bodies, for a time period sufficient to produce a blend characterised by content uniformity after size segregation, varies from the average content by less than 4.0% and comprising particles of the biologically active material having a median particle size, determined on a particle volume basis less than 1,000 nm dispersed in an at least partially milled grinding material.

* * * * *